(12) United States Patent
Owen et al.

(10) Patent No.: US 6,458,830 B1
(45) Date of Patent: Oct. 1, 2002

(54) TETRAHYDROPYRAN DERIVATIVES AND THEIR USE AS THERAPEUTIC AGENTS

(75) Inventors: Simon Neil Owen, London; Eileen Mary Seward, Bishop's Stortford; Christopher John Swain, Duxford; Brian John Williams, Great Dunmow, all of (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 09/936,343

(22) PCT Filed: Mar. 16, 2000

(86) PCT No.: PCT/GB00/00974

§ 371 (c)(1),
(2), (4) Date: Sep. 10, 2001

(87) PCT Pub. No.: WO00/56727

PCT Pub. Date: Sep. 28, 2000

(30) Foreign Application Priority Data

Mar. 19, 1999 (GB) ................................................. 9906480
Oct. 18, 1999 (GB) ................................................. 9924616

(51) Int. Cl.[7] ........................ A61K 31/35; A61K 31/41; A61K 31/415

(52) U.S. Cl. ........................ 514/460; 514/459; 514/422; 514/397; 514/359; 514/326; 514/231.5; 549/416; 549/417; 549/419; 544/149; 548/266.2; 548/311; 548/255; 548/517; 546/207

(58) Field of Search ................................ 549/416, 417, 549/419; 544/149; 546/207; 548/255, 266.2, 311.1, 517; 514/231.5, 326, 359, 397, 422, 459, 460

(56) References Cited

FOREIGN PATENT DOCUMENTS

EP          0 610 059 A     8/1994

OTHER PUBLICATIONS

A. Yamashita: Tetrahedron Letters., vol. 29, No. 28, 1988, pp. 3403–3406.

*Primary Examiner*—Amelia Owens
(74) *Attorney, Agent, or Firm*—J. Eric Thies; Mel Winokur

(57) ABSTRACT

The present invention relates to compounds of the formula (I):

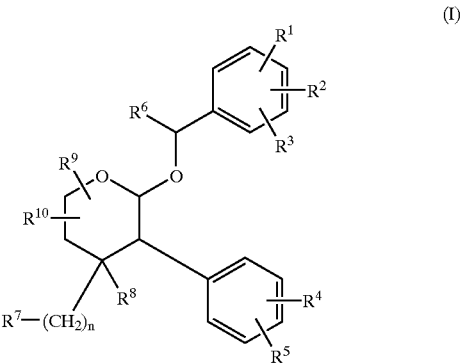

wherein $R^1$, $R^2$, $R^3$, $R^4$, $R^5$, $R^6$, $R^7$, $R^8$, $R^9$, $R^{10}$ and n are defined herein. The compounds are of particular use in the treatment or prevention of depression, anxiety, pain, inflammation, migraine, emesis and postherpetic neuralgia.

22 Claims, No Drawings

TETRAHYDROPYRAN DERIVATIVES AND THEIR USE AS THERAPEUTIC AGENTS

CROSS REFERENCE TO RELATED APPLICATIONS

This application is a U.S. National Phase application under 35 U.S.C. § 371 of PCT Application No. PCT/GB00/00974, filed Mar. 16, 2000, which claims priority under 35 U.S.C. § 119 from GB Application No. 9906480.0, filed Mar. 19, 1999 and GB Application No. 9924616.7 filed Oct. 18, 1999.

This invention relates to a class of tetrahydropyran compounds which are useful as tachykinin antagonists. More particularly, the compounds of the invention are useful as neurokinin 1(NK-1) receptor antagonists.

The present invention provides compounds of the formula (I):

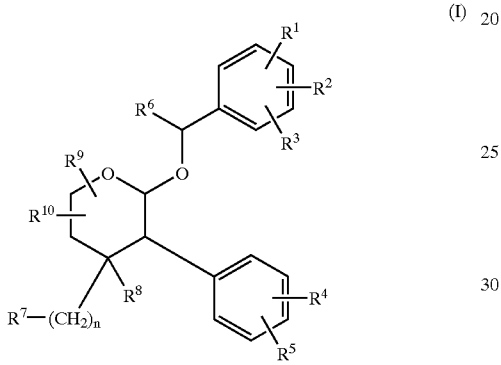

wherein
- $R^1$ is hydrogen, halogen, $C_{1-6}$alkyl, $C_{1-6}$alkoxy, fluoro$C_{1-6}$alkyl, fluoro$C_{1-6}$alkoxy, $C_{3-7}$cycloalkyl, $C_{3-7}$cycloalkyl$C_{1-4}$alkyl, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;
- $R^2$ is hydrogen, halogen, $C_{1-6}$alkyl, fluoro$C_{1-6}$alkyl or $C_{1-6}$alkoxy substituted by $C_{1-4}$alkoxy;
- $R^3$ is hydrogen, halogen or fluoro$C_{1-6}$alkyl;
- $R^4$ is hydrogen, halogen, $C_{1-6}$alkyl, $C_{1-6}$alkoxy, fluoro$C_{1-6}$alkyl, fluoro$C_{1-6}$alkoxy, hydroxy, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;
- $R^5$ is hydrogen, halogen, $C_{1-6}$alkyl, fluoro$C_{1-6}$alkyl or $C_{1-6}$alkoxy substituted by $C_{1-4}$alkoxy;
- $R^6$ represents hydrogen or a $C_{1-4}$alkyl group optionally substituted by a hydroxy group;
- $R^7$ represents halogen, hydroxy, $C_{2-4}$alkenyl, $C_{2-4}$alkynyl, $N_3$, $-NR^{11}R^{12}$, $-NR^aCOR^b$, $-OSO_2R^a$, $-(CH_2)_pNR^a(CH_2)_qCOOR^b$, $COR^a$, $COOR^a$, $-N=C=O$, or a five membered or six membered nitrogen-containing heteroaromatic ring optionally containing 1, 2 or 3 additional heteroatoms selected from N, O and S which heteroaromatic ring is optionally substituted at any substitutable position by a substituent selected from =O, =S, halogen, hydroxy, -SH, $COR^a$, $CO_2R^a$, $-ZNR^{11}R^{12}$, $C_{1-4}$alkyl, hydroxy$C_{1-4}$alkyl, fluoro$C_{1-4}$alkyl, chloro$C_{1-4}$alkyl, $C_{1-4}$alkoxy, fluoro$C_{1-4}$alkoxy or $C_{1-4}$alkoxy substituted by a $C_{1-4}$alkoxy or hydroxyl group, and wherein said $C_{2-4}$alkenyl and $C_{2-4}$alkynyl groups are optionally substituted by a substituent selected from halogen, hydroxy, $N_3$, $-NR^{11}R^{12}$, $-NR^aCOR^b$, $-OSO_2R^a$, $-(CH_2)_pNR^a(CH_2)_qCOOR^b$, $COR^a$ or $COOR^a$;
- $R^8$ represents hydrogen, $C_{1-6}$alkyl, fluoro$C_{1-6}$alkyl, hydroxy, $C_{1-6}$alkoxy or hydroxy$C_{1-6}$alkyl;
- $R^9$ and $R^{10}$ each independently represent hydrogen, halogen, $C_{1-6}$alkyl, $CH_2OR^c$, oxo, $CO_2R^a$ or $CONR^aR^b$ where $R^a$ and $R^b$ are as previously defined and $R^c$ represents hydrogen, $C_{1-6}$alkyl or phenyl;
- $R^{11}$ is hydrogen, $C_{1-4}$alkyl, $C_{3-7}$cycloalkyl, $C_{3-7}$cycloalkyl$C_{1-4}$alkyl, $C_{2-4}$alkyl substituted by a $C_{1-4}$alkoxy or hydroxyl group, or $R^{11}$ is a five membered or six membered nitrogen-containing heteroaromatic ring as previously defined;
- $R^{12}$ is hydrogen or $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;
- or $R^{11}$, $R^{12}$ and the nitrogen atom to which they are attached form a heteroaliphatic ring of 4 to 7 ring atoms, optionally substituted by one or two groups selected from hydroxy, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group, or a five membered or six membered nitrogen-containing heteroaromatic ring as previously defined, or said heteroaliphatic ring is substituted by a spiro-fused lactone ring, and said heteroaliphatic ring optionally containing a double bond, which heteroaliphatic ring may optionally contain an oxygen or sulphur ring atom, a group S(O) or $S(O)_2$ or a second nitrogen atom which will be part of a NH or $NR^d$ moiety, where $R^d$ is $C_{1-4}$alkyl optionally substituted by hydroxy or $C_{1-4}$alkoxy, and where $R^e$ is hydrogen, $C_{1-4}$alkyl or benzyl;
- or $R^{11}$, $R^{12}$ and the nitrogen atom to which they are attached form a non-aromatic azabicyclic ring system of 6 to 12 ring atoms;
- or $R^{11}$, $R^{12}$ and the nitrogen atom to which they are attached form a heteroaliphatic ring of 4 to 7 ring atoms to which is fused a benzene ring or a five membered or six membered nitrogen-containing heteroaromatic ring ring optionally containing 1, 2 or 3 additional heteroatoms selected from N, O and S;
- Z represents a bond, $C_{1-6}$alkylene or $C_{3-6}$cycloalkylene;
- n is zero, 1 or 2;
- p is 1 or 2; and
- q is 1 or 2;

and pharmaceutically acceptable salts thereof.

A preferred class of compounds of formula (I) is that wherein:
- $R^7$ represents halogen, hydroxy, $C_{2-4}$alkenyl, $N_3$, $-NR^{11}R^{12}$, $-NR^aCOR^b$, $-OSO_2R^a$, $-(CH_2)_pNR^a(CH_2)_qCOOR^b$, $COR^a$, $COOR^a$, or a five membered or six membered nitrogen-containing heteroaromatic ring optionally containing 1, 2 or 3 additional heteroatoms selected from N, O and S which heteroaromatic ring is optionally substituted at any substitutable position by a substituent selected from =O, =S, halogen, hydroxy, -SH, $COR^a$, $CO_2R^a$, $-ZNR^{11}R^{12}$, $C_{1-4}$alkyl, hydroxy$C_{1-4}$alkyl, fluoro$C_{1-4}$alkyl, $C_{1-4}$alkoxy, fluoro$C_{1-4}$alkoxy or $C_{1-4}$alkoxy substituted by a $C_{1-4}$alkoxy or hydroxyl group.

Another preferred class of compounds of formula (I) is that wherein:

R$^7$ represents halogen, hydroxy, C$_{2-4}$alkenyl, N$_3$, —NR$^{11}$R$^{12}$, —NR$^a$COR$^b$, —OSO$_2$R$^a$, —(CH$_2$)$_p$NR$^a$(CH$_2$)$_q$COOR$^b$ or a five membered or six membered nitrogen-containing heteroaromatic ring optionally containing 1, 2 or 3 additional heteroatoms selected from N, O and S which heteroaromatic ring is optionally substituted at any substitutable position by a substituent selected from =O, =S, halogen, hydroxy, —SH, COR$^a$, CO$_2$R$^a$, —ZNR$^{11}$R$^{12}$, C$_{1-4}$alkyl, hydroxyC$_{1-4}$alkyl, fluoroC$_{1-4}$alkyl, C$_{1-4}$alkoxy, fluoroC$_{1-4}$alkoxy or C$_{1-4}$alkoxy substituted by a C$_{1-4}$alkoxy or hydroxyl group;

R$^{11}$ is hydrogen or C$_{1-4}$alkyl, C$_{3-7}$cycloalkyl, C$_{3-7}$cycloalkylC$_{1-4}$alkyl, or C$_{2-4}$alkyl substituted by a C$_{1-4}$alkoxy or hydroxyl group;

R$^{12}$ is hydrogen or C$_{1-4}$alkyl, C$_{3-7}$cycloalkyl, C$_{3-7}$cycloalkylC$_{1-4}$alkyl, or C$_{2-4}$alkyl substituted by a C$_{1-4}$alkoxy or hydroxyl group;

or R$^{11}$, R$^{12}$ and the nitrogen atom to which they are attached form a heteroaliphatic ring of 4 to 7 ring atoms, optionally substituted by one or two groups selected from hydroxy, COR$^a$, CO$_2$R$^a$ or C$_{1-4}$alkoxy optionally substituted by a C$_{1-4}$alkoxy or hydroxyl group, and said ring optionally containing a double bond, which ring may optionally contain an oxygen or sulphur ring atom, a group S(O) or S(O)$_2$ or a second nitrogen atom which will be part of a NH or NR$^d$ moiety where R$^d$ is C$_{1-4}$alkyl optionally substituted by hydroxy or C$_{1-4}$alkoxy;

or R$^{11}$, R$^{12}$ and the nitrogen atom to which they are attached form a non-aromatic azabicyclic ring system of 6 to 12 ring atoms;

or a pharmaceutically acceptable salt thereof.

A further preferred class of compounds of formula (I) is that wherein R$^1$ is hydrogen, C$_{1-4}$alkyl, C$_{1-4}$alkoxy, halogen or CF$_3$.

Another preferred class of compounds of formula (I) is that wherein R$^2$ is hydrogen, C$_{1-4}$alkyl, C$_{1-4}$alkoxy, halogen or CF$_3$.

Also preferred is the class of compounds of formula (I) wherein R$^3$ is hydrogen, fluorine, chlorine or CF$_3$.

A particularly preferred class of compounds of formula (I) is that wherein R$^1$ is fluorine, chlorine or CF$_3$.

Another particularly preferred class of compounds of formula (I) is that wherein R$^2$ is hydrogen, fluorine, chlorine or CF$_3$.

Also particularly preferred is the class of compounds of formula (I) wherein R$^3$ is hydrogen, fluorine, chlorine or CF$_3$.

Preferably R$^1$ and R$^2$ are in the 3 and 5 positions of the phenyl ring.

More preferably R$^1$ is 3-fluoro or 3-CF$_3$.

More preferably R$^2$ is 5-fluoro or 5-CF$_3$.

More preferably R$^3$ is hydrogen.

Most preferably R$^1$ is 3-F or 3-CF$_3$, R$^2$ is 5-CF$_3$ and R$^3$ is hydrogen.

A further preferred class of compound of formula (I) is that wherein R$^4$ is hydrogen.

Another preferred class of compounds of formula (I) is that wherein R$^5$ is hydrogen, fluorine, chlorine or CF$_3$.

Preferably R$^4$ is hydrogen and R$^5$ is hydrogen or 4-fluoro.

R$^6$ is preferably C$_{1-4}$alkyl optionally substituted by hydroxy. In particular, R$^6$ is preferably a methyl or hydroxymethyl group.

Where —NR$^{11}$R$^{12}$ is defined as a substituent R$^7$ or as a substituent on a heteroaromatic ring in the definition of R$^7$, then R$^{11}$ may aptly be a C$_{1-4}$alkyl group or a C$_{2-4}$alkyl group substituted by a hydroxyl or C$_{1-2}$alkoxy group, R$^{12}$ may aptly be a C$_{1-4}$alkyl group or a C$_{2-4}$alkyl group substituted by a hydroxyl or C$_{1-2}$alkoxy group, or R$^{11}$ and R$^{12}$ may be linked so that, together with the nitrogen atom to which they are attached, they form an azetidinyl, pyrrolidinyl, piperidinyl, morpholino, thiomorpholino, piperazino or piperazino group substituted on the nitrogen atom by a C$_{1-4}$alkyl group or a C$_{2-4}$alkyl group substituted by a hydroxy or C$_{1-2}$alkoxy group. Particularly preferred heteroaliphatic rings formed by —NR$^{11}$R$^{12}$ are azetidine, pyrolidine, piperidine, morpholine, piperazine and N-methylpiperazine, and especially piperidine.

Where the group NR$^{11}$R$^{12}$ represents a heteroaliphatic ring of 4 to 7 ring atoms substituted by two groups, the first substituent, where present, is preferably selected from hydroxy, CO$_2$R$^e$ (where R$^e$ is hydrogen, methyl, ethyl or benzyl), or C$_{1-2}$alkyl substituted by hydroxy. Where present, the second substituent is preferably a methyl group. Where two substituents are present, said substituents are preferably attached to the same carbon atom of the heteroaliphatic ring.

Where the group NR$^{11}$R$^{12}$ represents a heteroaliphatic ring of 4 to 7 ring atoms substituted by a spiro-fused lactone ring, a particularly preferred example is:

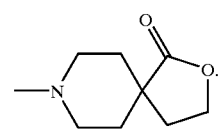

Another preferred example is:

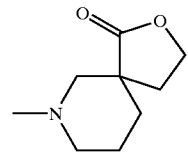

Where the group NR$^{11}$R$^{12}$ represents a heteroaliphatic ring of 4 to 7 ring atoms and said ring contains a double bond, a particularly preferred group is 3-pyrroline.

Where the group NR$^{11}$R$^{12}$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.3.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where the group NR$^{11}$R$^{12}$ represents a heteroaliphatic ring of 4 to 7 ring atoms to which is fused a benzene ring or a five membered or six membered nitrogen-containing heteroaromatic ring ring optionally containing 1, 2 or 3 additional heteroatoms selected from N, O and S, said heteroaromatic ring is preferably a five-membered ring, in particular a pyrrole, imidazole or triazole ring, a nitrogen atom of which is preferably included in the heteroaliphatic ring. Suitable examples of such fused ring systems include

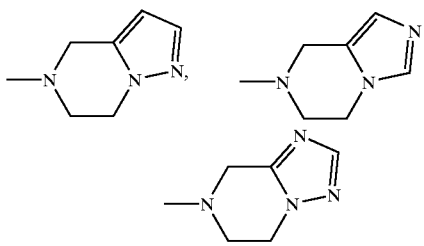

Particularly suitable moieties $NR^{11}R^{12}$ include those wherein $NR^{11}R^{12}$ is amino, methylamino, dimethylamino, diethylamino, azetidino, pyrrolidino, piperidino, morpholino and piperazino.

Where $R^7$ represents an optionally substituted five or six-membered nitrogen-containing heteroaromatic ring optionally containing 1, 2 or 3 additional heteroatoms selected from N, O and S, the heteroaromatic ring is selected from pyrrole, pyridine, pyrazole, imidazole, oxazole, isoxazole, thiazole, isothiazole, pyrazine, pyrimidine, pyridazine, triazole, oxadiazole, thiadiazole, triazine, and tetrazole.

Preferred compounds of the present invention are those wherein $R^7$ is a group selected from imidazole, 1,2,3-triazole and 1,2,4-triazole.

Particularly preferred compounds of the present invention are those wherein $R^7$ is a group selected from imidazol-1-yl and 1,2,4-triazol-1-yl.

Where $R^7$ represents an optionally substituted five membered or six membered nitrogen-containing heteroaromatic ring, preferred substituents are —$ZNR^{11}R^{12}$ and $C_{1-2}$alkyl (especially methyl). With reference to the group $ZNR^{11}R^{12}$ defined as a substituent on a heteroaromatic ring in the definition of $R^7$, Z may be a bond or a linear, branched or cyclic group. Favourably Z is a bond or contains 1 to 4 carbon atoms and most favourably 1 to 2 carbon atoms. A particularly favourable group Z is —$CH_2$—. In this instance, particularly suitable moieties $NR^{11}R^{12}$ include those wherein $NR^{11}R^{12}$ is amino, methylamino, dimethylamino, diethylamino, azetidino, pyrrolidino, piperidino, morpholino and piperazino. Most especially, —$ZNR^{11}R^{12}$, as a substituent on a heteroaromatic ring in the definition of $R^7$, is preferably $CH_2N(CH_3)_2$.

A further preferred class of compound of formula (I) is that wherein $R^7$ represents halogen (especially iodine), hydroxy, vinyl, $N_3$ or —$OSO_2R^a$ (especially where $R^a$ is methyl).

Another preferred class of compound of formula (I) is that wherein $R^8$ is hydrogen or methyl, and especially hydrogen.

A further preferred class of compound of formula (I) is that wherein n is 1 or 2, and especially wherein n is 1.

Another preferred class of compound of formula (I) is that wherein one of $R^9$ and $R^{10}$ is hydrogen, and especially wherein $R^9$ and $R^{10}$ are both hydrogen atoms.

One favoured group of compounds of the present invention are of the formula (Ia) and pharmaceutically acceptable salts thereof:

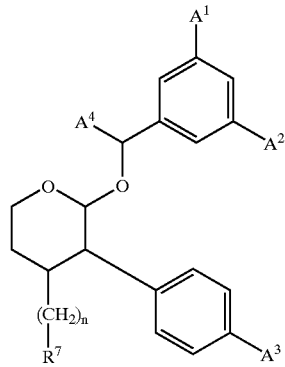

(Ia)

wherein
$A^1$ is fluorine or $CF_3$;
$A^2$ is fluorine or $CF_3$;
$A^3$ is fluorine or hydrogen;
$A^4$ is methyl or hydroxymethyl; and
$R^7$ and n are as defined in relation to formula (I).

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and fluoro$C_{1-6}$ alkoxy" means a $C_{1-6}$alkyl or $C_{1-6}$alkoxy group in which one or more (in particular, 1 to 3) hydrogen atoms have been replaced by fluorine atoms Similarly, the term "fluoro$C_{1-4}$alkyl" means a $C_{1-4}$alkyl group in which one or more (in particular 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

When used herein the term "halogen" means fluorine, chlorine, bromine and iodine. The most apt halogens are fluorine and chlorine of which fluorine is preferred, unless otherwise stated.

Specific compounds within the scope of this invention include:
(2R,3S,4R,8R)-2-(1-(1-(3,5-bis(trifluoromethyl)phenyl) ethyl)oxy)-3-phenyl-4-vinyltetrahydropyran;
(2R,3R,4S,8R)-2-(1-(1-(3,5-bis(trifluoromethyl)phenyl) ethyl)oxy)-3-phenyl-4-vinyltetrahydropyran;
(2R,3S,4S,8R)-2-(1-(1-(3,5-bis(trifluoromethyl)phenyl) ethyl)oxy)-4-hydroxymethyl-3-phenyltetrahydropyran;
(2R,3S,4S,8R)-2-(1-(1-(3,5-bis(trifluoromethyl)phenyl) ethyl)oxy)-4-(methanesulfonyloxy)methyl-3-phenyltetrahydropyran;

(2RS,3SR,4SR,8RS)-4-azidomethyl-2-(1-(1-(3,5-bis(trifluoromethyl)phenyl)ethyl)-oxy)-3-phenyltetrahydropyran;
(2RS,3SR,4SR,8RS)-4-aminomethyl-2-(1-(1-(3,5-bis(trifluoromethyl)phenyl)-ethyl)oxy)-3-phenyltetrahydropyran;
(2RS,3SR,4SR,8RS)-2-(1-(1-(3,5-bis(trifluoromethyl)phenyl)ethyl)oxy)-4-(dimethylamino)methyl-3-phenyltetrahydropyran;
(2RS,3SR,4SR,8RS)-2-(1-(1-(3,5-bis(trifluoromethyl)phenyl)ethyl)oxy)-4-(pyrrolidin-1-yl)methyl-3-phenyltetrahydropyran;
(2RS,3SR,4SR,8RS)-2-(1-(1-(3,5-bis(trifluoromethyl)phenyl)ethyl)oxy)-4-(1,2,4-triazol-1-yl)methyl-3-phenyltetrahydropyran;
(2R,3S,4S,8R)-2-(1-(1-(3,5-bis(trifluoromethyl)phenyl)ethyl)oxy)-4-(2-hydroxyethyl)-3-phenyltetrahydropyran;
(2R,3S,4R,8R)-2-(1-(1-(3,5-bis(trifluoromethyl)phenyl)ethyl)oxy)-4-(2-methanesulfonyloxy)ethyl-3-phenyltetrahydropyran;
(2R,3R,4R,8R)-2-(1-(1-(3,5-bis(trifluoromethyl)phenyl)ethyl)oxy)-4-hydroxymethyl-3-phenyltetrahydropyran;
(2R,3R,4R,8R)-2-(1-(1-(3,5-is(trifluoromethyl)phenyl)ethyl)oxy)-4-(methanesulfonyloxy)methyl-3-phenyltetrahydropyran;
(2R,3R,4R,8R)-2-(1-(1-(3,5-bis(trifluoromethyl)phenyl)ethyl)oxy)-4-(2-hydroxyethyl)-3-phenyltetrahydropyran;
(2R,3R,4S,8R)-2-(1-(1-(3,5-bis(trifluoromethyl)phenyl)ethyl)oxy)-4-(2-methanesulfonyloxy)ethyl-3-phenyltetrahydropyran;
and pharmaceutically acceptable salts thereof.

Further specific compounds of the present invention include:

(2R,3S,4R,8R)-2-(1-(1-(3,5-Bis(trifluoromethyl)phenyl)ethyl)oxy)-4-(2-iodoethyl)-3-phenyltetrahydropyran;
(2R,3R,4R,8R)-2-(1-(1-(3,5-Bis(trifluoromethyl)phenyl)ethyl)oxy)-4-(iodomethyl)-3-phenyltetrahydropyran;
(2R,3R,4S,8R)-2-(1-(1-(3,5-Bis(trifluoromethyl)phenyl)ethyl)oxy)-4-(2-iodoethyl)-3-phenyltetrahydropyran;
(2R,3S,4S,8R)-2-(1-(1-(3,5-Bis(trifluoromethyl)phenyl)ethyl)oxy)-4-formyl-3-phenyltetrahydropyran;
(2R,3S,4R,8R)-2-(1-(1-(3,5-Bis(trifluoromethyl)phenyl)ethyl)oxy)-4-(2-formylmethyl)-3-phenyltetrahydropyran;
(2R,3R,4R,8R)-2-(1-(1-(3,5-Bis(trifluoromethyl)phenyl)ethyl)oxy)-4-formyl-3-phenyltetrahydropyran;
(2R,3S,4R,8R)-2-(1-(1-(3,5-Bis(trifluoromethyl)phenyl)ethyl)oxy)-4-carboxymethyl-3-phenyltetrahydropyran;
(2R,3R,4R,8R)-2-(1-(1-(3,5-Bis(trifluoromethyl)phenyl)ethyl)oxy)-4-carboxy-3-phenyltetrahydropyran;
(2R,3R,4R,8R)-2-(1-(1-(3,5-Bis(trifluoromethyl)phenyl)ethyl)oxy)-4-(4-methyl-4-carboxypiperidin-1-yl)methyl-3-phenyltetrahydropyran;
(2R,3R,4R,8R)-2-(1-(1-(3,5,-Bis(trifluoromethyl)phenyl)ethyl)oxy)-4-(4-ethoxycarbonylpiperidin-1-yl)methyl-3-phenyltetrahydropyran;
(2R,3R,4R,8R)-2-(1-(1-(3,5,-Bis(trifluoromethyl)phenyl)ethyl)oxy)-4-(4-carboxypiperidin-1-yl)methyl-3-phenyltetrahydropyran;
(2R,3R,4R,8R,9(3'R))-2-(1-(1-(3,5-Bis(trifluoromethyl)phenyl)ethyl)oxy)-4-(3-ethoxycarbonyl-3-methylpiperldin-1-yl)methyl-3-phenyltetrahydropyran;
(2R,3R,4R,8R,9(3'S))-2-(1-(1-(3,5-Bis(trifluoromethyl)phenyl)ethyl)oxy)-4-(3-ethoxycarbonyl-3-methylpiperidin-1-yl)methyl-3-phenyltetrahydropyran;
(2R,3R,4R,8R,9(3'R))-2-(1-(1-(3,5-Bis(trifluoromethyl)phenyl)ethyl)oxy)-4-(3-carboxy-3-methylpiperidin-1-yl)methyl-3-phenyltetrahydropyran;
(2R,3R,4R,8R,9(3'S))-2-(1-(1-(3,5-Bis(trifluoromethyl)phenyl)ethyl)oxy)-4-(3-carboxy-3-methylpiperidin-1-yl)lmethyl-3-phenytetrahydropyran;
(2R,3R,4R,8R)-2-(1-(1-(3,5-Bis(trifluoromethyl)phenyl)ethyl)oxy)-3-phenyl-4-(1,2,4-triazol-3-yl)methyltetrahydropyran;
(2R,3S,4S,8R)-2-(1-(1-(3,5-Bis(trifluoromethyl)phenyl)ethyl)oxy)-3-phenyl-4-(1,2,4-triazol-3-yl)methyltetrahydropyran;
(2R,3R,4R,8R)-2-(1-(1-(3,5-Bis(trifluoromethyl)phenyl)ethyl)oxy)-3-phenyl-4-(5-methoxycarbonyl-1,2,3-triazol-1-yl)ethyltetrahydropyran; (2R,3R,4R,8R)-2-(1-(1-(3,5-Bis(trifluoromethyl)phenyl)ethyl)oxy)-4-(4-methoxycarbonyl-1,2,3-triazol-1-yl)ethyl-3-phenyltetrahydropyran;
and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I) and (Ia) will have the stereochemistry of the 2-, 3-, 4- and 8-positions as shown in formulae (Ib) and (Ic)

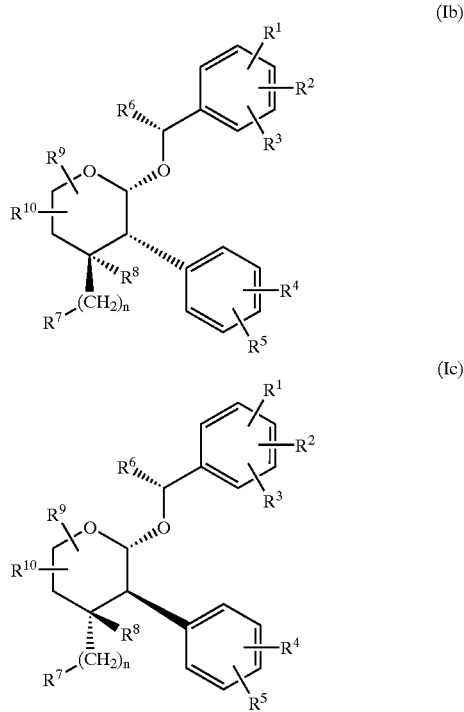

It will be appreciated that the preferred definitions of the various substituents recited herein may be taken alone or in combination and, unless otherwise stated, apply to the generic formula for compounds of the present invention as well as to the preferred classes of compound represented by formula (Ia), formula (Ib) and formula (Ic).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, ethyleneimine compounds, alkyl sulphonates and other compounds with an alkylating action such as nitrosoureas, cisplatin and dacarbazine;

antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting, Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or domperidone or GABA$_B$ receptor agonists such as baclofen. Additionally, a compound of formula (I), either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

Suitable methods for determining the anti-emetic effects of compounds of the present invention are well known in the art, for example, using the ferret model of cisplatin-induced emesis described by F. D. Tattersall et al, in *Eur. J. Pharmacol.*, (1993) 250, R5–R6.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache, including migraine, acute or chronic tension headache, cluster headache, temporomandibular pain, and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination. Thus, for example, for the treatment of respiratory diseases such as asthma, a compound of formula (I) may be used in conjunction with a bronchodilator, such as a β$_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D$_4$ antagonist such as a compound selected from those disclosed in European patent specification Nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and $5-HT_{1A}$ agonists or antagonists, especially $5-HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable $5-HT_{1A}$ receptor agonists or antagonists include, in particular, the $5-HT_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders.

The present invention also provides a method for the treatment or prevention of eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptble salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief.

In a further aspect of the present invention, there is provided a pharmaceutical composition for the treatment or prevention of obesity comprising a compound of formula (I) and an SSRI, together with at least one pharmaceutically acceptable carrier or excipient.

It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of formula (I) and an SSRI as a combined preparation for simultaneous, separate or sequential use in the treatment or prevention of obesity.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared (kg/m$^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycyvstc ovarian disease, cardiovascular diseases, osteoarthritis, dermatological disorders, hypertension, insulin resistance, hypercholesterolemia, hypertriglyceridemia, and cholelithiasis.

A further aspect of the present invention comprises the use of a compound of formula (I) for achieving a chronobiologic (circadian rhythm phase-shifting) effect and alleviating circadian rhythm disorders in a mammal. The present invention is further directed to the use of a compound of formula (I) for blocking the phase-shifting effects of light in a mammal.

The present invention further relates to the use of a compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of formula (I) or a pharmaceutically acceptable salt thereof.

The present invention is further directed to the use of a compound of formula (I) or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of formula (I) or a pharmaceutically acceptable salt thereof The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

As used herein the term "mammals" includes animals of economic importance such as bovine, ovine, and porcine animals, especially those that produce meat, as well as domestic animals, sports animals, zoo animals, and humans, the latter being preferred.

It will be appreciated that when using any combination described herein, both the compound of formula (I) and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), compounds of formula (I), in which n is 1, may be prepared by the reaction of a compound of formula (II)

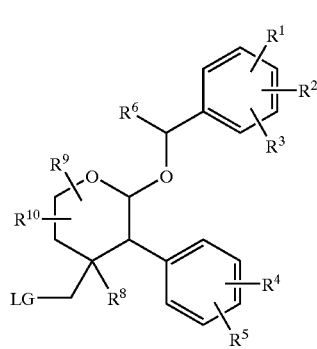

wherein LG is a suitable leaving group such as an alkyl- or arylsulfonyloxy group (e.g. mesylate or tosylate) or a halogen atom (e.g. bromine, chlorine or iodine); by reaction with an appropriate amine of the formula $HNR^{11}R^{12}$, or a heteroaromatic compound suitable for the addition of a five or six-membered nitrogen containing heteroaromatic ring as defined in relation to formula (I), or an azide such as sodium azide.

In each case, the reaction is preferably effected at an elevated temperature, for example, between 40° C. and 80° C., especially between 50° C. and 60° C. The reaction with a heteroaromatic compound is preferably effected in the presence of a suitable organic solvent such as dimethylformamide. The reaction with an azide is preferably effected in the presence of dimethylsulfoxide.

A particularly preferred compound of formula (II) is that wherein the group LG is mesylate—i.e. a compound of formula (I) in which $R^7$ is the group —$OSO_2CH_3$.

According to another general process (B), compounds of formula (I), in which $R^7$ is hydroxy and n is 1 or 2, may be prepared by the interconversion of a corresponding compound of formula (I) in which n is zero and $R^7$ is vinyl, hereinafter referred to as formula (III)

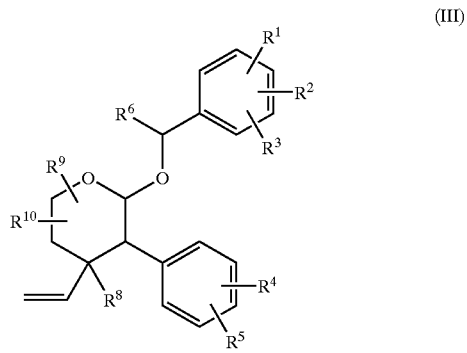

by reaction with ozone, followed by a reaction with a reducing agent such as sodium borohydride (n is 1), or by reaction with a reducing agent such as borane.tetrahydrofuran complex, followed by hydrogen peroxide in the presence of a base such as sodium hydroxide.

According to another general process (C), compounds of formula (I) may be prepared by the reaction of a compound of formula (IV) with a compound of formula (V)

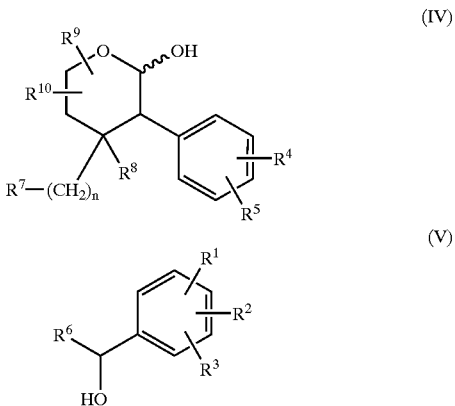

preferably in the presence of a resin catalyst such as Amberlyst™ 15, and 3 Angstrom molecular sieves.

The reaction is conveniently effected in a suitable solvent such as a halogenated hydrocarbon, for example, dichloromethane, conveniently at room temperature.

According to another general process (D), compounds of formula (I), in which $R^6$ is either methyl or hydroxymethyl, may be prepared by the reaction of a compound of formula (VI)

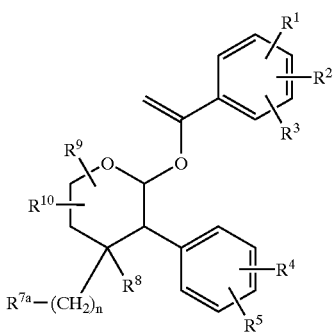

(VI)

wherein $R^{7a}$ is as defined for $R^7$ in relation to formula (I) or, more preferably, is a precursor therefor; under either:

(a) (where $R^6$ is methyl) catalytic hydrogenation conditions (e.g. $H_2$, $Pd(OH)_2$ on carbon) in a suitable solvent such as an ester, for example, ethyl acetate; or (b) (where $R^6$ is hydroxymethyl) reducing conditions (e.g borane or $BH_3.THF$) followed by treatment with hydrogen peroxide and a base such as sodium hydroxide, conveniently in a solvent such as an ether, for example, tetrahydrofuran.

Where $R^{7a}$ is a precursor group (such as a TBDMS-protected hydroxyl group) deprotection is conveniently effected by treatment with an organic acid such as tetrabutylammonium fluoride.

Further details of suitable procedures will be found in the accompanying Examples.

Compounds of formula (II) may be prepared by conventional methods from, for example, a corresponding compound of formula (I) in which $R^7$ is a hydroxyl group. Thus, for example, when LG is a mesylate group a corresponding compound of formula (I) in which $R^7$ is hydroxyl may be reacted with methanesulfonyl chloride in the presence of a base, such as triethylamine. The reaction is conveniently effected in a solvent such as a halogenated hydrocarbon, for example, dichloromethane.

Compounds of formula (III) may be prepared, for example, by the method of general process (C), above.

Compounds of formula (IV) may be prepared by the reduction of a compound of formula (VII)

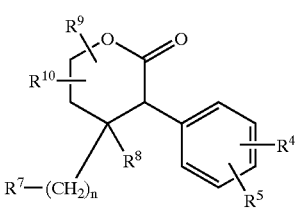

(VII)

using conventional conditions such as sodium borohydride in the presence of a transition metal catalyst such as cerium chloride hexahydrate, in a solvent such as alcohol, for example, ethanol; or using DiBAL in a solvent such as a halogenated hydrocarbon, for example, dichloromethane.

Compounds of formula (VII) in which $R^7$ is vinyl, $R^8$ is hydrogen and n is 1 may be prepared from a compound of formula (VIII)

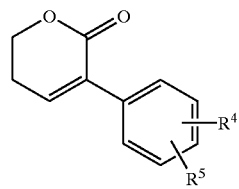

(VIII)

by reaction with a vinyl Grignard reagent such as vinylMgBr, preferably in the presence of copper(I)iodide, and a suitable solvent such as an ether, for example, tetrahydrofuran. This reaction is effected at reduced temperature, for example, below −40° C. and preferably at −78° C.

Compounds of formula (VI) may be prepared by the reaction of a compound of formula (X)

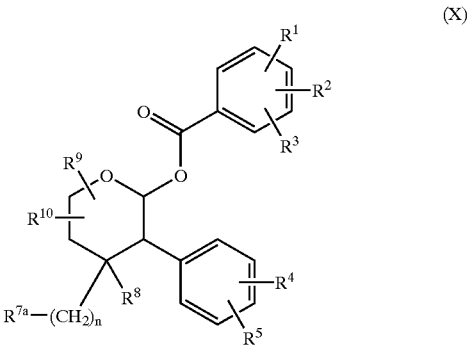

(X)

with dimethyltitanocene in a solvent such as toluene, pyridine or tetrahydrofuran, or a mixture thereof.

Compounds of formula (X) may be prepared by the reaction of a compound of formula (VII) with L-Selectride™ (lithium tri-sec-butylborohydride) followed by treatment with a compound of formula (XI)

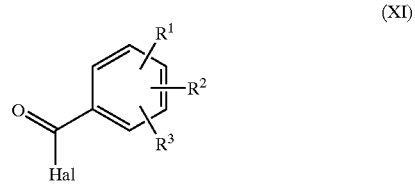

(XI)

wherein Hal is a halogen atom, preferably chlorine.

Compounds of formula (V), (VIII) and (XI) are either known compounds or may be prepared by methods analogous to those described herein.

It will be appreciated that the general methodology described above may be adapted, using methods that are readily apparent to one of ordinary skill in the art, in order to prepare further compounds of the present invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 100 nM on said test method.

The following non-limiting Examples serve to illustrate the preparation of compounds of the present invention:

DESCRIPTION 1

3-Phenyl-4-vinyl-3,4,5,6-tetrahydropyran-2-one

Vinylmagnesium bromide (77 ml, 1M THF) was added to a slurry of copper (I) iodide (7.37 g) in tetrahydrofuran (80 ml) at −78° C. under a nitrogen atmosphere. This mixture was stirred at −40° C. for 30 minutes, then recooled to −78° C. A solution of 3-phenyl-5,6-dihydro-2-pyrone (*J. Org. Chem.* 1967, 32, 2354) (4.6 g) and chlorotrimethylsilane (3.28 ml) in THF (80 ml) was added to the stirred mixture. Thin layer chromatography showed all starting material had reacted. The mixture was quenched with ammonium chloride (saturated aqueous solution) at −78° C. and the resulting mixture was allowed to come to room temperature and was stirred for 2 hours until the aqueous layer became dark blue. The mixture was filtered through Celite™ to remove any insoluble inorganics and the solution was extracted with ethyl acetate (3×100 ml). The pooled organic extracts were washed with brine, dried ($MgSO_4$) and concentrated to give a yellow oil. This was purified on silica using 30–40% ether in hexane as eluant to afford the title compound (4.9 g, crystallised on standing) as a mixture of cis and trans isomers (2:1). Recrystallisation of this mixture from ether-hexane afforded the pure cis isomer as white prisms.

Signals for the cis lactone: $^1$H NMR (360 MHz, $CDCl_3$) δ 1.95–2.15 (2H, m), 2.91–3.00 (1H, m), 3.51 (1H, d, J 5.8Hz), 4.59–4.65 (2H, m), 4.93–5.00 (2H, m), 5.48–5.58 (1H, m), 7.17–7.19 (2H, m), 7.26–7.35 (3H, m). Signals for the trans lactone: $^1$H NMR (360 MHz, $CDCl_3$) δ 1.89–1.99 (1H, m), 2.10–2.18 (1H, m), 2.79–2.85 (1H, m), 3.51 (1H, d, J 10.3Hz), 4.43–4.57 (2H, m), 4.90–5.01 (2H, m), 5.66 (1H, hept, J 17.2, 10.4, 7.0 Hz), 7.16–7.20 (2H, m), 7.23–7.36 (3H, m).

DESCRIPTION 2

(2RS,3SR,4SR)-2-(3,5-bis(Trifluoromethyl)benzoyloxy)-3-phenyl-4-vinyltetrahydropyran The compound of Description 1 (1.8 g, mixture of isomers) was dissolved in THF (30 ml) and the solution was cooled to −78° C. under a nitrogen atmosphere. L-Selectride™ (9.8 ml, 1M in THF) was added dropwise to afford a clear yellow solution; this solution was stirred at −78° C. for 30 minutes. 3,5-Bis(trifluoromethyl)benzoyl chloride (1.7 ml) was added to the solution and tlc analysis showed that all starting material had reacted. The reaction mixture was quenched (ammonium chloride) at low temperature and was subsequently extracted with ethyl acetate (3×50 ml). The pooled organic extracts were washed with brine and dried ($MgSO_4$) and concentrated in vacuo to give a yellow oil. This was purified on silica using 5% ether in hexane as eluant to afford the title compound as a colourless oil. $^1$H NMR (360 MHz, $CDCl_3$) δ 1.72–1.77 (1H, m), 2.00–2.10 (1H, m), 2.84–2.96 (1H, m), 3.33 (1H, dd J 3.1, 3.0 Hz), 3.88 (1H, ddd J 12.1, 12.0, 3.3), 4.30 (1H, ddd J 12.1, 4.5, 4.5), 5.02–5.07 (2H, m), 5.72 (1H, hept, J 17.2, 10.1, 7 Hz), 6.32 (1H, d, 3.1 Hz), 7.25–7.33 (3H, m), 7.40–7.43 (2H, m), 7.99 (1H, s), 8.19 (2H, s).

DESCRIPTION 3

(2RS,3SR,4RS)-2-(3,5-bis(Trifluoromethyl)phenyl)benzoyloxy)-4-formyl-3-phenyltetrahydropyran The compound of Description 2 (5.1 g) was dissolved in a mixture of dichloromethane (75 ml) and methanol (50 ml). This solution was cooled to −78° C. under an inert atmosphere. Ozone was bubbled through the colourless solution until a blue colouration persisted; the solution was then purged with oxygen to remove excess ozone. Dimethyl sulfide (20 ml) was added and the solution was stirred overnight. The solution was concentrated in vacuo and the residue was dispersed between water and ethyl acatate. The ethyl acetate extract was washed with water, brine, dried ($MgSO_4$) and concentrated in vacuo to afford the title compound as a colourless oil. This compound was not purified further at this stage. $^1$H NMR (360 MHz, $CDCl_3$) δ 1.95–2.02 (1H, m), 2.36–2.46 (1H, m), 3.15 (1H, q, J 5.5 Hz), 3.80–3.87 (2H, m), 4.16–4.23 (1H, m), 6.60 (1H, d, J 2.6 Hz), 7.20–7.39 (5H, m), 8.05 (1H, s), 8.35 (2H, s), 9.75 (1H, s).

DESCRIPTION 4

(2RS,3SR,4SR)-2-(3,5-bis(Trifluoromethyl)phenyl)benzoyloxy)-4-formyl-3-phenyltetrahydropyran The compound of Description 3 (1.8 g) was dissolved in dichloromethane (20 ml) and diazabicycloundecane (0.15 ml) was added. This solution was stirred for 2 h and the mixture was concentrated in vacuo. The residue was purified on silica using 10–20% ethyl acetate in hexane as eluant to afford the title compound as a colourless oil which crystallised on standing (1.59 g). $^1$H NMR (360 MHz, $CDCl_3$) δ 1.92–2.13 (2H, m), 3.43–3.57 (2H, m), 4.02 (2H, dd, J 12.3, 3.4 Hz), 6.41 (1H, d, 4.2 Hz), 7.22–7.31 (5H, m), 8.07 (1H, s), 8.36 (2H, s), 9.57 (1H, d, J 3.0 Hz).

DESCRIPTION 5

(2RS,3SR,4SR)-2-(3,5-bis(Trifluoromethyl)phenyl)benzoyloxy)-4-hydroxymethyl-3-phenyltetrahydropyran The compound of Description 4 (1.96 g) was dissolved in dichloroethane (20 ml) and sodium triacetoxyborohydride (1.86 g) was added portionwise. The mixture was stirred at room temperature for 12 hours. Thin layer chromatography analysis showed that some starting material still remained; thus, additional aliquots of reductant were added (3×500 mg) in portions until complete reduction occurred. The mixture was poured onto sodium bicarbonate (saturated aqueous solution) and stirred until all effervescence ceased. The organic layer was washed with additional sodium bicarbonate solution, brine, dried ($MgSO_4$) and concentrated in vacuo to give the title compound as a white foam (2 g). $^1$H NMR (360 MHz, $CDCl_3$) δ 1.82–1.97 (1H, m), 2.04–2.10 (1H, m), 2.60–2.74 (1H, m), 3.12 (1H, dd, J 12.2, 3.2 Hz), 3.38–3.46 (1H, m), 3.62–3.66 (1H, m), 3.98–4.05 (2H, m), 6.33 (1H, d, J 3.2 Hz), 7.20–7.31 (5H, m), 8.07 (1H, s), 8.42 (2H, s).

DESCRIPTION 6

(2RS,3SR,4SR)-2-(3,5-bis(Trifluoromethyl)phenyl)benzoyloxy)-4-(tert-butyldimethylsilyloxy)methyl-3-phenyltetrahydropyran The compound of Description 5 (2.0 g) was dissolved in dimethylformamide (3 ml) and imidazole (758 mg) and tert-butyldimethylsilyl chloride (807 mg) were added. The resulting solution was stirred at room temperature for 1 hour until tlc analysis confirmed that all starting material had reacted. The solution was diluted with water (30 ml) and was extracted with ethyl acetate (3×20 ml). The combined organic extracts were washed with brine, dried (MgSO$_4$) and concentrated in vacuo to afford a colourless oil. This was purified on silica using 3% ether in hexane as eluant to afford the title compound (2 g). $^1$H NMR (360 MHz, CDCl$_3$) δ −0.13 (3H, s), −0.06 (3H, s), 0.86 (9H, s), 1.86–2.02 (2H, m), 2.52–2.71 (1H, m), 3.15 (1H, dd, 12.1, 3.2 Hz), 3.32 (1H, dd, 10.0, 6.0 Hz), 3.54 (1H, dd, 10.0, 2.8 Hz), 3.93–4.09 (2H, m), 6.32 (1H, d, J 3.2 Hz), 7.17–7.27 (5H, m), 8.07 1H, s), 8.43 (2H, s).

DESCRIPTION 7

(2RS,3SR,4SR)-2-(3,5-bis(Trifluoromethyl)phenyl) ethylenoxy)-4-(tert-butyldimethylsilyloxy)methyl-3-phenyltetrahydropyran The compound of Description 6 (1.0 g) was dissolved in toluene (1 ml) and pyridine (1 ml) and a solution of dim-ethyltitanocene (12 ml, 0.3M) was added. The resulting red solution was degassed using a Firestone valve and purged with nitrogen (×3) and was stirred at 80° C. for 1 hour. An additional portion of dimethyltitanocene (15 ml) was added and stirring was continued for 3 hours. The solution was cooled and concentrated in vacuo; hexane was added to precipitate inorganic salts and these were removed by filtration through Celite™. The hexane solution was concentrated and the residue was purified on silica using 0.5% triethylamine in hexane to 2% ether in hexane to afford the title compound as a pale yellow oil (0.65 g). $^1$H NMR (360 MHz, CDCl$_3$) δ −0.16 (3H, s), −0.09 (3H, s), 0.84 (9H, s), 1.87–1.90 (2H, m), 2.55–2.67 (1H, m), 3.05 (1H, dd, J 12.1, 3.3 Hz), 3.32 (1H, dd, J 10.0, 6.0 Hz), 3.50 (1H, dd J 10.0, 2.7 Hz), 3.80–3.97 (2H, m), 4.80 (2H, dd, J 16.8, 2.9 Hz), 5.41 (1H, d, J 3.1 Hz), 7.22–7.27 (2H, m), 7.32–7.34 (3H, m), 7.78 (1H, s), 7.90 (2H, s).

DESCRIPTION 8

(2RS,3SR,4SR,8RS)-2-(3,5-bis(Trifluoromethyl) phenyl)ethoxy)-4-(tert-butyldimethylsilyloxy) methyl-3-phenyltetrahydropyran The compound of Description 7 (600 mg) was dissolved in ethyl acetate (50 ml) and palladium hydroxide (10% on carbon) was added. The mixture was hydrogenated at 40 psi hydrogen for 2 hours. The solution was filtered to remove the catalyst and concentrated to give a clear oil. This was purified on silica using 30–40% dichloromethane in hexane as eluant to afford the title compound as a clear oil (543 mg). $^1$H NMR (360 MHz, CDCl$_3$) δ −0.16 (3H, s), −0.10 (3H, s), 0.83 (9H, s), 1.45 (3H, d, J 6.6 Hz), 1.68–1.82 (1H, m), 1.86–1.94 (1H, m), 2.50–2.63 (1H, m), 2.76 (1H, dd, J 12.0, 3.1 Hz), 3.20 (1H, dd, J 9.8, 6.5 Hz), 3.42 (1H, dd, J 9.8, 2.8 Hz), 3.74–3.78 (1H, m), 4.01–4.10 (1H, m), 4.45 (1H, d, J 3.2 Hz), 4.88 (1H, q, J 6.6 Hz), 7.21–7.27 (7H, m), 7.59 (1H, s).

DESCRIPTION 9

5,6-Dihydro-3-phenylpyran-2-one

A solution of 3-bromo-5,6-dihydropyran-2-one (*Org. Syn.*, 1996, 73, 231) (74.9 g), phenylboronic acid (51.8 g), potassium carbonate (294 g) and tetrakis (triphenylphosphine) palladium(0) (3.4 g) in toluene was heated (100° C.) under an atmosphere of nitrogen for 24 hours. The cooled solution was diluted by addition of ethyl acetate (1000 ml) and water (1000 ml) and the mixture filtered through Hiflo™. The organic phase was dried (MgSO$_4$), evaporated in vacuo and the residue crystallised from methanol and then toluene to give the title compound, 43 g. mp. 100–101° C.

DESCRIPTION 10 trans 3-Phenyl-4-vinyl-3,4,5,6-tetrahydropyran-2-one

A mixture of cis- and trans-3-phenyl-4-vinyl-5,6-dihydropyran-2-one (Description 1; 5.25 g; ratio 2:1) in tetrahydrofuran (10 ml) was heated in an oil bath (80° C.) with 1,8-diazabicyclo[5.4.0]undec-7-ene (0.2 g) for 30 minutes. The cooled solution was evaporated in vacuo and a solution of the residue in dichloromethane (50 ml) was filtered through a pad of silica gel. After washing the silica with dichloromethane (50 ml), the combined filtrate was evaporated to dryness (4.8 g, cis:trans ratio 1:19) and used without further purification. $^1$H NMR (360 MHz, CDCl$_3$) δ 1.99–1.89 (1H, m), 2.18–2.10 (1H, m), 2.88–2.79 (1H, m), 3.50 (1H, d J 10.3 Hz), 4.57–4.443 (2H, m), 5.03–4.90 (2H, m), 5.71–5.63 (1H, m), 7.36–7.16 (5H, m).

DESCRIPTION 11 trans 3-Phenyl-4-vinyl-tetrahydropyran-2-ol

To a cooled (−30° C.) solution of trans 3-phenyl-4-vinyl-5,6-dihydropyran-2-one (Description 10; 0.97 g) in ethanol (21 ml) was added a solution of cerium chloride hexahydrate (1.79 g) in water (7 ml) followed by a slow addition of sodium borohydride (0.18 g) (so as to maintain an internal temperature of −20° C. to −30° C.). After stirring the solution for 30 minutes at −30° C. acetone (2 ml) was added. The solution was evaporated and the residue partitioned between ethyl acetate and water. The organic phase was dried (MgSO$_4$) and evaporated to dryness (0.92 g) giving a mixture of 2,3-cis:trans lactol isomers (approximately 30:70 by NMR). $^1$H NMR (360 MHz, CDCl$_3$) δ 1.67–1.80 (m), 2.35 (d J 2.0 Hz), 2.38 (1.6H, dd J 11.4 Hz and 8.3 Hz), 2.6 (1.9H, m), 2.8 (dd J 12.0 Hz and 2.7 Hz), 3.2 (m), 3.75 (m) 4.15 (m), 4.24 (dd J 12.2 Hz and 3.0 Hz),4.78–4.87 (m), 4.95 (dt J 17.2 Hz and 1.36 Hz), 5.20 (dd J 5.8 Hz and 2.9 Hz), 5.46–5.57 (m), 7.18–7.34 (m).

DESCRIPTION 12

3,5-bis(Trifluoromethyl)styrene Oxide

A solution of 3,5-bis(trifluoromethyl)styrene (13.3 g) and m-chloroperbenzoic acid (21 g) in dichloromethane (100 ml) was stirred at room temperature for 16 hours. The resulting suspension was diluted with water (100 ml) and dichloromethane (100 ml), and the organic phase was washed further with water (2×100 ml) and saturated brine (100 ml). After drying (MgSO$_4$) the solvent was removed in vacuo and the residue purified by chromatography on silica (eluting with isohexane followed by 10% ethyl acetate in isohexane) to provide the title compound. $^1$H NMR (400 MHz, CDCl$_3$) δ 2.79 (1H, dd J 6.0 Hz and 2.7 Hz), 3.23 (1H, dd J 5.9 Hz and 4.5 Hz), 3.99 (1H, dd J 4,4 Hz and 2.7 Hz), 7,74 (2H,s), 7.82 (1H, s).

DESCRIPTION 13

2-Benzyloxy-1-(3,5-bis(trifluoromethyl)phenyl)-1-hydroxyethane

To a cooled (0° C.) solution of 3,5-bis(trifluoromethyl) styrene oxide (Description 12, 0.5 g) and benzyl alcohol (1 g) in tetrahydrofuran (10 ml) was added sodium hydride (50% in mineral oil, 48 mg). The solution was stirred at room temperature for 16 hours. A further addition of sodium hydride (20 mg) was made and the solution heated to reflux for 2 hours. The cooled solution was evaporated to dryness and the residue purified by chromatography on silica (eluting with increasing concentrations of ethyl acetate in isohexane 0–20%) to provide the title compound. $^1$H NMR (360 MHz, CDCl$_3$) δ 3.22 (1H, d J 3.1 Hz), 3.48 (1H, dd J 8.2 Hz and 9.6 Hz), 3.67 (1H, dd J 9.7 Hz and 3.5 Hz), 4.57 (1H, s), 4.98 (1H, m), 7.23–7.37 (5H, m), 7.80 (1H, s), 7.83 (2H, s).

DESCRIPTION 14

(2RS,3SR,4RS,8SR)-2-(2-Benzyloxy-1-(1-(3,5-bis(trifluoromethyl)phenyl)ethyl)oxy)-3-phenyl-4-vinyltetrahydropyran; and (2RS,3RS,4SR,8SR)-2-(2-Benzyloxy-1-(1-(3,5-bis(trifluoromethyl)phenyl)ethyl)oxy)-3-phenyl-4-vinyltetrahydropyran A solution of the product of Description 11 (2 g) and the product of Description 13 (3.73 g) in dichloromethane (10 ml) were stirred at room temperature for 5 days with Amberlyst™ 15 (0.5 g) and 3 Å molecular sieves (2 g). The filtered solution was evaporated to dryness and the residue purified by chromatography on silica (eluting with increasing proportions of dichloromethane in isohexane (5–100%)).
Isomer 1
(faster eluting as a mixture of major and minor isomers approximately 10:4): $^1$H NMR (360 MHz, CDCl$_3$) δ 1.53–1.80 (4.1H, m), 2.72 (1H, dd, J 12.0 Hz and 3.2 Hz), 2.82 (0.4H, dd J 12.2 Hz and 3.2 Hz), 3.1–3.3 (2.8H, m), 3.52 (1H, dd J 10.3 Hz and 4.7 Hz), 3.60 (1H, m), 3.73 (1H, dd J 10.2 Hz and 6.8 Hz), 4.117 (1H, dd J 16.9 Hz and 2.7 Hz), 4.20 (1H, td J 12.5 Hz and 2.8 Hz), 4.53 (1H, d 3.1 Hz), 4,58 (2H, ABd J 12.2 Hz), 4.75–5.0 (7H, m), 5.52 (1.5H, m), 6.98 (0.7H, m) 7.06 (0.7H, dd J 7.7 Hz and 2.1 Hz), 7.17–7.4 (17H, m), 7.62 (1H, s), 7.72 (1H, s),7.8 (0.4H, s), 7.83 (0.8H, s).
Isomer 2
(slower eluting major isomer): $^1$H NMR (360 MHz, CDCl$_3$) δ 1.71 (2H, m), 2.44–2.58 (2H, m), 3.43 (1H, dd J 10.2 Hz and 6.0 Hz), 3.58 (1H, m), 3.70 (1H, dd J 10.1 Hz and 5.5 Hz), 4.15 (1H, dt J 11.8 Hz and 3.6 Hz), 4.29 (1H, d J 8.0 Hz), 4.44 (1H, ABd J 12.2 Hz), 4.49 (1H, ABd J 12.1 Hz), 4.78 (1H, d J 1.7 Hz), 4.82 (1H, d J 3.1 Hz), 5.02 (1H, t J 5.8 Hz), 5.49 (1H, m), 7.01 (2H, m), 7.14 (2H, dd J 7.7 Hz and 2.1 Hz), 7.24–7.35 (8H, m), 7.68 (1H, s).

DESCRIPTION 15

Benzyl 4-Methylpiperidine-4-carboxylate
(i) N-Butoxycarbonylpiperidine-4-carboxylic Acid
Isonipecotic acid (6.42 g) was dissolved in a 4:1 mixture of tetrahydrofuran:water (100 ml), potassium carbonate (10.3 g) and di-tert-butyl dicarbonate (11.4 g) were added and stirred at room temperature over night. The tetrahydrofuran was removed in vacuo and the residue dispersed between water (100 ml) and ethyl acetate (100 ml), the aqueous phase was extracted with ethyl acetate (3×75 ml). The combined organics were washed with brine and dried (MgSO$_4$). The solution was filtered, evaporated to dryness to afford a white solid of N-butoxycarbonylpiperidine-4-carboxylic acid(11.6 g).
$^1$H NMR (360 MHz, CDCl$_3$) δ 1.46 (9H, s), 1.58–1.71 (2H, m), 1.87–1.95 (2H, m), 2.45–2.53 (1H, m), 2.81–2.90 (2H, m), 3.97–4.04 (2H, m).

(ii) Benzyl N-Butoxycarbonylpiperidine-4-carboxylate
N-Butoxycarbonyl-4-piperidinecarboxylic acid (4.6 g) was dissolved in dimethylformamide (20 ml) and placed under an atmosphere of nitrogen. Benzyl bromide (2.9 ml) and potassium carbonate (8.3 g) were added and heated at 60° C. for 3 h. The dimethylformamide was removed in vacuo and azeotroped with toluene (three times). The residue was dispersed between ethyl acetate and water and the aqueous phase was extracted with ethyl acetate (3×100 ml). The combined organic phases were washed with brine and dried (MgSO$_4$). The solution was filtered, evaporated to dryness and the residue was purified by chromatography on silica gel (eluting with isohexane containing increasing concentrations amounts of ethyl acetate 5–30%) to give benzyl N-butoxycarbonylpiperidine-4-carboxylate as a clear oil (7.68 g).
$^1$H NMR (400 MHz, CDCl$_3$) δ 1.45 (9H, s), 1.61–1.70 (2H, m), 1.87–1.94 (2H, m), 2.45–2.53 (1H, m), 2.77–2.87 (2H, m), 23.96–4.06 (2H, m), 5.13 (2H, s)7.28–7.38 (5H, m).

(iii) Benzyl N-Butoxycarbonyl-4-methylpiperidine-4-carboxylate
The benzyl ester (5.18 g) was dissolved in tetrahydrofuran (40 ml) under an atmosphere of nitrogen and cooled to −78° C., potassium bis(trimethylsilyl)amide (32.5 ml 0.5M in toluene) was added dropwise keeping the internal temperature below −60° C. The reaction was stirred at −78° C. for 15 mins, methyl iodide (2.5 ml) was added and the temperature was allowed to warm to room temperature. Water (5 ml) was added, the solvent was removed in vacuo, and the residue was dispersed between ethyl acetate (100 ml) and water (100 ml). The aqueous layer was extracted with ethyl acetate (3×60 ml), the combined organics were washed with brine and dried over MgSO$_4$. The solution was filtered, evaporated to dryness and the residue was purified by chromatography on silica gel (eluting with isohexane containing increasing concentrations of ethyl acetate 2.5–5%) to give a clear oil (3.4 g).
$^1$H NMR (400 MHz, CDCl$_3$) δ 1.22 (3H, s), 1.33–1.42 (2H, m), 1.44 (9H, s), 2.05–2.12 (2H, m), 2.95–3.03 (2H, m), 3.68–3.78 (2H, m), 5.14 (2H, s), 7.30–7.39 (5H, m).

(iv) Benzyl 4-Methylpiperidine-4-carboxylate
The Boc-protected amine (2.8 g) was dissolved in dichloromethane (4 ml) and cooled to 0° C., trifluoroacetic acid (2 ml) was added dropwise and the reaction allowed to warm to room temperature. After 1 hr the solvent was removed in vacuo and the residue dispersed between ethyl acetate (50 ml) and sat. K$_2$CO$_3$ (50 ml). The aqueous layer was extracted with ethyl acetate (3×30 ml), the combined organics were washed with brine and dried over MgSO$_4$. The solution was filtered, evaporated to dryness to afford a white solid (1.91 g). MS m/z (ES$^+$) 234 (M+H).
$^1$H NMR (400 MHz, CDCl$_3$) δ 1.22 (3H, s), 1.40 (2H, ddd J 10 Hz 10 Hz 3.9 Hz), 1.98 (1H, s), 2.10 (2H, dm J 16.5 Hz), 2.67 (2H, ddd J 10.3 Hz 10.3 Hz 2.8 Hz), 2.91 (2H, m), 5.14 (2H, s), 7.28–7.39 (5H, m).

DESCRIPTION 16

(±) Ethyl 3-Methylpiperidine-3-carboxylate
(i)Ethyl N-(t-Butyloxycarbonyl)nipecotate
Di-t-butyl dicarbonate (138.8 g, 0.63 mol) was dissolved in dichloromethane (500 ml) and the resulting solution was cooled in an ice bath. Ethyl nipecotate (100 g, 0.64 mol) in dichloromethane (100 ml) was added dropwise to the stirred solution resulting in copious effervescence. This solution was stirred at room temperature overnight and was then evaporated leaving a colourless oil which crystallized on standing (161 g). mp 39–40° C.

¹H NMR (400 MHz, CDCl$_3$) δ 1.26 (3H, t, J 7.1 Hz), 1.46 (9H, s), 1.55–1.76 (3H, m), 2.02–2.09 (1H, m), 2.40–2.49 (1H, m) 2.81 (1H, dt), 2.85–3.11 (1H, v br m), 3.86–3.95 (1H, m) 4.14 (2H, q, J 7.1 Hz) 4.12–4.16 (1H, br m). MS (ES$^+$) m/z 258 (MH$^+$, 15%), 202 (MH$^+$ –56, 80%), 184 (MH$^+$ –74, 10%), 158 (MH$^+$ –100, 10%).

(ii) Ethyl N-t-Butyloxycarbonyl-3-methylpiperidine-3-carboxylate

Potassium bis(trimethylsilyl)amide (1200 ml, 0.5M in toluene, 0.6 mol) was added to a 3-necked 3-l flask equipped with an overhead stirrer, followed by tetrahydrofuran (90 ml) and the solution was cooled to –78° C. Ethyl N-(t-butyloxycarbonyl)nipecotate (100 g, 0.39 mol) in tetrahydrofuran (90 ml) was added dropwise and the resulting solution allowed to age for 15 minutes. Iodomethane (37.4 ml, 85.2 g, 0.6 mol) was added dropwise to the stirred solution keeping the temperature below –70° C. The resulting mixture was stirred at room temperature overnight and was evaporated under reduced pressure. The residue was partitioned between ethyl acetate and water and the organic layer was washed with brine, dried (sodium sulphate) and evaporated to give a yellow oil. This was purified on a plug of silica using dichloromethane as eluant to afford the product (94 g, 90%) as a pale yellow oil.

¹H NMR (400 MHz, CDCl$_3$) δ 1.16 (3H, s), 1.25 (3H, t, J 7.1 Hz), 1.45 (9H, br s), 1.52–1.62 (3H, m), 1.98–2.06 (1H, m), 3.13 (1H, d, J 13.3 Hz), 3.19–3.30 (1H, m), 3.39–3.47 (1H, m), 3.83 (1H, d, J 13.3 Hz), 4.08–4.16 (2H, m). MS (ES$^+$) m/z 272 (MH$^+$, 15%), 216 (MH$^+$ –56, 100%), 198 (MH$^+$ –74, 80%), 172 (MH$^+$ –100, 10%).

(iii) Ethyl 3-Methylpiperidinium-3-carboxylate Hydrochloride

Through a cooled (0° C.) solution of ethyl N-t-butyloxycarbonyl-3-methylpiperidine-3-carboxylate (94.1 g) in ethyl acetate (2500 ml) was bubbled hydrogen chloride gas until the solution was saturated. The solution was allowed to stand at room temperature for 16 h and then evaporated under reduced pressure. The residue was crystallised from ethyl acetate to give the first crop of the title compound 59 g (together with additional material 12.9 g from crop 2), mp 143–144° C.

¹H NMR (360 MHz, CDCl$_3$) δ 1.10 (3H, s), 1.27 (3H, t, J 7.1 Hz), 1.32–1.49 (2H, m), 1.50–1.60 (1H, m), 2.12–2.21 (1H, m), 2.41 (1H, d, J 13.0 Hz), 2.57–2.62 (1H, m), 2.90–2.95 (1H, m), 3.32 (1H, d, J 13.0 Hz), 4.11–4.23 (2H, m). MS (ES$^+$) m/z 172 (MH$^+$, 100%).

DESCRIPTION 17

4-(4-Methyltriazol-3-yl)piperidine Hydrochloride i) N-Benzyloxycarbonyl-4-(N$^4$-methyl(thiosemicarbazido)carbonyl)piperidine N-Benzyloxycarbonyl-4-(hydrazinocarbonyl)piperidine (231 g) was dissolved in toluene (500 ml) and a solution of methyl isothiocyanate (90 g) in toluene (50 ml) was added with stirring. After 1hr the resulting precipitate was separated, washed with ether and dried to give the title compound (280 g).

ii) N-Benzyloxycarbonyl-4-(5-mercapto-4-methyltriazol-3-yl)piperidine

Sodium (54 g) was dissolved in methanol (785 ml), by adding portions of 4–5 g, under cooling on an ice bath. To the obtained methanolic NaOMe solution was added the compound of step (i) (270 g). The reaction mixture was refluxed with a condenser for 1 hr. Then it was diluted with aqueous acetic acid (400 ml), containing 135 ml (141 g) of acid, on an ice bath with stirring. Upon addition of the last portion of acid a solid precipitated. It was separated, washed with ether and dried to give the title compound (230 g).

iii) N-Benzyloxycarbonyl-4-(4-methyltriazol-3-yl)piperidine

The compound of step (ii) (225 g) was dissolved by adding portions of 15–20 g to concentrated nitric acid (10M, 500 ml) on an ice bath with stirring. The mixture was stirred for 1 hr and poured onto an ice-cold solution of KOH (600 g) with continuous addition of ice. Then the reaction mixture was divided into 4 portions and each portion of 500 ml was extracted with 300 ml of chloroform. The combined organic layers were dried with anhydrous sodium sulfate and then evaporated in vacuo to give the title compound.

iv) 4-(4-Methyltriazol-3-yl)piperidine Hydrochloride

The compound of step (iii) was re-dissolved in methanol to the volume of 400 ml. Then to the solution were added 5% Pd/C and concentrated HCl (50 ml). The mixture was hydrogenated for 24 hr at hydrogen pressure of 100 atm and temperature 90° C. The mixture was cooled, filtered and evaporated. The resulting oily residue was dissolved at reflux in isopropanol (100 ml) and to the solution was added concentrated HCl (50 ml). The mixture was allowed to crystallise at 5° C. for 3 days and then filtered to give the title compound (135 g).

¹H NMR (100 MHz, DMSO-d$_6$) δ 1.90–2.15 (4H, m), 2.88–3.10 (2H, m), 3.20–3.50 (3H, m), 3.77 (3H, s), 9.30 (1H, s). MS (CI$^+$) m/z 167 (MH$^+$, 100%).

DESCRIPTION 18

3-(4-Fluoro)phenyl-5,6-dihydro-2-pyranone

The title compound was prepared by a procedure analogous to that described in Description 9 using 3-bromo-5,6 dihydropyran-2-one and 4-fluorophenylboronic acid.

¹H NMR (360 MHz, CDCl$_3$) δ 2.60–2.65 (2H, m), 4.47–4.51 (2H, m), 6.98 (1H, t, J 4.5 Hz), 7.02–7.08 (2H, m), 7.42–7.47 (2H, m).

DESCRIPTION 19 trans-3-(4-Fluoro)phenyl-4-vinyl-3,4,5,6-tetrahydropyranone

The title compound was prepared by a procedure analogous to that described in Description 1 from the product of Description 18 followed by a procedure analogous to Description 10.

¹H NMR (360 MHz, CDCl$_3$) δ 1.88–2.07 (1H, m), 2.10–2.19 (1H, m), 2.72–2.83 (1H, m), 3.47 (1H, d, J 10.7 Hz), 4.41–4.58 (2H, m), 4.88 (1H, d, J 10.3 Hz), 4.99 (1H, d, J 10.3 Hz), 5.57–5.68 (1H, m), 6.94–7.08 (2H, m), 7.09–7.18 (2H, m).

DESCRIPTION 20

3,4-trans-3-(4-Fluoro)phenyl-4-vinyl-3,4,5,6-tetrahydropyran-2-ol

The title compound was prepared by a procedure analogous to that described in Description 11 from the product of Description 19.

Mixture of diastereoisomers: ¹H NMR (360 MHz, CDCl$_3$) δ 1.55–1.81 (m), 2.36 (1H, dd, J 11.4, 8.3 Hz, H-3$_{isomer\ 1}$), 2.44–2.57 (m), 2.58–2.67 (m), 2.75 (1H, dd, J 11.8, 2.6 Hz, H-3$_{isomer\ 2}$), 2.92–3.08 (m), 3.10 (1H, d, J4.9 Hz), 3.51–3.76 (m), 3.79–3.91 (m), 4.03–4.23 (m), 4.70–4.78 (m), 4.79–5.07 (m), 5.11–5.20 (m), 5.40–5.52 (m), 6.91–7.05 (m), 7.08–7.18 (m), 7.19–7.28 (m).

DESCRIPTION 21

(S)-1-(3,5-bis(Trifluoromethyl)phenyl)ethan-1,2-diol 3,5-Bis(trifluromethyl)styrene (13 g) was dissolved in a mixture of water (270 ml) and 2-methylpropan-2-ol (270 ml)

and cooled to 0° C. AD-mix-α (76 g) was added in one portion and the reaction left to warm to room temperature over 72 hours. The mixture was then cooled to 0° C., sodium sulfite (81 g) added and the reaction mixture extracted into ethyl acetate (3×250 ml). The combined organics were dried (brine, MgSO₄) and concentrated under reduced pressure to afford the product as a crude orange solid which was purified on silica eluting with 35% ethyl acetate/iso-hexane to afford the product as a crystalline white solid (chiral hplc, ee 92.2%). This was recrystallised from toluene to give the title compound as a white fibres (chiral hplc, ee 96.2%).

¹H NMR (CDCl₃, 400 MHz): δ 1.98–2.04 (1H, m), 2.81 (1H, d, J 2.44 Hz), 3.62–3.69 (1H, m), 3.84–3.90 (1H, m), 4.92–4.98 (1H, m), 7.82 (1H, s), 7.86 (1H, s).

DESCRIPTION 22

(S)-2-Benzyloxy-1-(3,5-bis(trifluoromethyl)phenyl)ethanol (S)-1-(3,5-Bis(trifluoromethyl)phenyl)ethan-1,2-diol (11.45 g) and di-n-butyltin oxide (10.40 g) were dissolved in toluene (200 ml) and refluxed in a Dean and Stark apparatus for 16 hours. The toluene was removed under reduced pressure, cesium fluoride (12.70 g) suspended in N,N-dimethylformamide (200 ml) was added and the reaction stirred for 1 hour. The reaction was diluted with water and filtered through Hyflo™ before concentrating under reduced pressure and extracting into ethyl acetate. The organic phase was dried (brine, MgSO₄) and concentrated under reduced pressure to give a crude brown oil. This was purified on silica eluting with 20% ethyl acetate/iso-hexane to afford the title compound as a pale yellow oil.

¹H NMR (CDCl₃, ₄₀₀ MHz): δ 3.04 (1H, d, J 2.6 Hz), 3.50 (1H, t, J 9.0 Hz), 3.69 (1H, dd, J 9.6, 7.2 Hz), 4.60 (1H, s), 4.98–5.03 (1H, s), 7.29–7.38 (1H, m), 7.80 (1H, s), 7.85 (2H, s).

DESCRIPTION 23

(2R,3S,4R,8S)-2-(2-Benzyloxy-1-(1-(3,5-bis(trifluoromethyl)phenyl)ethyl)oxy)-3-phenyl-4-vinyl-3,4,5,6-tetrahydropyran; and (2R,3R,4S,8S)-2-(2-Benzyloxy-1-(1-(3,5-bis(trifluoromethyl)phenyl)ethyl)oxy)-3-phenyl-4-vinyl-3,4,5,6-tetrahydropyran The title compounds were prepared from the product of Description 22 and the product of Description 11 by a method analogous to that described in Description 14.

Isomer 1 (2,3-cis-3,4-trans)

(faster eluting as a mixture of major and minor isomers approximately 10:4): ¹H NMR (360 MHz, CDCl₃) δ 1.53–1.80 (4.1H, m), 2.72 (1H, dd, J 12.0 Hz and 3.2 Hz), 2.82 (0.4H, dd J 12.2 Hz and 3.2 Hz), 3.1–3.3 (2.8H, m), 3.52 (1H, dd J 10.3 Hz and 4.7 Hz), 3.60 (1H, m), 3.73 (1H, dd J 10.2 Hz and 6.8 Hz), 4.117 (1H, dd J 16.9 Hz and 2.7 Hz), 4.20 (1H, td J 12.5 Hz and 2.8 Hz), 4.53 (1H, d 3.1 Hz), 4,58 (2H, ABd J 12.2 Hz), 4.75–5.0 (7H, m), 5.52 (1.5H, m), 6.98 (0.7H, m) 7.06 (0.7H, dd J 7.7 Hz and 2.1 Hz), 7.17–7.4 (17H, m), 7.62 (1H, s), 7.72 (1H, s), 7.8 (0.4H, s), 7.83 (0.8H, s).

Isomer 2 (2,3-trans-3,4-trans)

(slower eluting major isomer): ¹H NMR (360 MHz, CDCl₃) δ 1.71 (2H, m), 2.44–2.58 (2H, m), 3.43 (1H, dd J 10.2 Hz and 6.0 Hz), 3.58 (1H, m), 3.70 (1H, dd J 10.1 Hz and 5.5 Hz), 4.15 (1H, dt J 11.8 Hz and 3.6 Hz), 4.29 (1H, d J 8.0 Hz), 4.44 (1H, ABd J 12.2 Hz), 4.49 (1H, ABd J 12.1 Hz), 4.78 (1H, d J 1.7 Hz), 4.82 (1H, d J 3.1 Hz), 5.02 (1H, t J 5.8 Hz), 5.49 (1H, m), 7.01 (2H, m), 7.14 (2H, dd J 7.7 Hz and 2.1 Hz), 7.24–7.35 (8H, m), 7.68 (1H, s).

DESCRIPTION 24

(2R,3S,4S,8S)-2-(2-Benzyloxy-1-(1-(3,5-bis(trifluoromethyl)phenyl)ethyl)oxy)-3-phenyl-4-(hydroxymethyl)-3,4,5,6-tetrahydropyran The title compound was prepared from isomer 1 (Description 23) by a method analogous to that described in Example 5.

¹H NMR (360 MHz, CDCl₃) δ 1.08 (1H, t, J 5.3 Hz), 1.73 (1H, td, J 11.8, 5.1 Hz), 1.91 (1H, bd, J 13.2 Hz), 2.58–2.71 (1H, m), 2.77 (1H, dd, J 12.1, 3.1 Hz), 3.27–3.36 (1H, m), 3.46–3.58 (2H, m), 3.70–3.81 (2H, m), 4.19 (1H, td, J 11.4, 2,6 Hz), 4.50 (1H, d, J 3.1 Hz), 4.56 (1H, d, J 12.3 Hz), 4.59 (1H, d, J 12.3 Hz), 4.99 (1H, dd, J 6.6, 4.7 Hz), 7.20–7.36 (12H, m), 7.62 (1H, s).

DESCRIPTION 25

(2R,3S,4S,8S)-2-(2-Benzyloxy-1-(1-(3,5-bis(trifluoromethyl)phenyl)ethyl)oxy)-3-phenyl-4-(2-hydroxyethyl)-3,4,5,6-tetrahydropyran The title compound was prepared from isomer 1 (Description 23) by a method analogous to that described in Example 20.

¹H NMR (360 MHz, CDCl₃) δ 1.12–1.21 (1H, m), 1.48–1.64 (2H, m), 1.95 (1H, bd J 13.5 Hz), 3.52 (1H, dd J 10.2 4.8 Hz), 3.58–3.64 (1H, m), 3.68–3.75 (1H, m), 4.11–4.19 (1H, m), 4.48 (1H, d J 1.9 Hz), 4.56 (1H, dd J 14.5, 11.3 Hz), 4.97 (1H, dd J 6.6, 4.8 Hz), 7.18–7.37 (12H, m), 7.61 (1H, s).

DESCRIPTION 26

(2R,3R,4R,8S)-2-(2-Benzyloxy-1-(1-(3,5-bis(trifluoromethyl)phenyl)ethyl)oxy)-3-phenyl-4-(hydroxymethyl)-3,4,5,6-tetrahydropyran The title compound was prepared from isomer 2 (Description 23) by a method analogous to that described in Example 5.

¹H NMR (360 MHz, CDCl₃) δ 1.07 (1H, t, J5.1 Hz), 7.58–1.72 (1H, m), 1.78–1.84 (1H, m), 1.91–2.03 (1H, m), 2.59 (1H, dd, J 11.6, 8.4 Hz), 3.23–3.31 (1H, m), 3.37–3.45 (2H, m), 3.56 (1H, td, J 12.0, 2.4 Hz), 3.69 (1H, dd, J 10.2, 5.5 Hz), 4.18 (1H, ddd, J 11.7, 4.6, 1.7 Hz), 4.31 (1H, d, J8.3 Hz), 4.44 (1H, d, J 12.2 Hz), 4.48 (1H, d, J 12.2 Hz), 5.02 (1H, t, J5.8 Hz), 7.03–7.15 (4H, m), 7.19–7.30 (9H, m), 7.68 (1H, s).

DESCRIPTION 27

(2R,3R,4R,8S)-2-(2-Benzyloxy-1-(1-(3,5-bis(trifluoromethyl)phenyl)ethyl)oxy)-3-phenyl-4-(2-hydroxyethyl)-3,4,5,6-tetrahydropyran The title compound was prepared from isomer 2 (Description 23) by a method analogous to that described in Example 20.

¹H NMR (400 MHz, CDCl₃) δ 1.19–1.29 (1H, m)1.41–1.55 (2H, m), 1.80 (1H, dt 13.5 1.9 Hz), 1.90–2.02 (1H, m), 2.45 (1H, dd J 11.4, 8.4 Hz), 3.38–3.56 (4H, m), 3.68 (1H, dd, J 10.1, 5.5 Hz), 4.09–4.15 (1H, m), 4.26 (1H, d, J 8.4 Hz), 4.46 (1H, dd, J 20.0, 12.1 Hz), 5.00 (1H, t, J 5.7 Hz), 7.01–7.07 (2H, m), 7.09–7.13 (2H, m), 7.17–7.28 (8H, m), 7.67 (1H, s).

DESCRIPTION 28

(2R,3S,4S,8S)-2-(2-Benzyloxy-1-(1-(3,5-bis(trifluoromethyl)phenyl)ethyl)oxy)-3-phenyl-4-(methanesulfonyloxymethyl)-3,4,5,6-tetrahydropyran The title compound was prepared from the compound of Description 24 by a method analogous to that described in Example 6.

$^1$H NMR (360 MHz, CDCl$_3$) δ 1.62–1.35 (1H, m), 1.91–1.98 (1H, m), 2.77 (3H, s), 2.80 (1H, d, J 3.0 Hz), 2.83–2.93 (1H, m), 3.53 (1H, dd, J 10.2, 4.5 Hz), 3.68–3.86 (3H, m), 4.08 (1H, dd, J 9.8, 3.0 Hz), 4.15–4.24 (1H, m), 4.49–4.62 (2H, m), 4.98 (1H, dd, J 6.8, 4.5 Hz), 7.18–7.38 (12H, m), 7.62 (1H, s).

DESCRIPTION 29

(2R,3S,4R,8S)-2-(2-Benzyloxy-1-(1-(3,5-bis(trifluoromethyl)phenyl)ethyl)oxy)-3-phenyl-4-(2-methanesulfonyloxyethyl)-3,4,5,6-tetrahydropyran The title compound was prepared from the compound of Description 25 by a method analogous to that described in Example 6.

$^1$H NMR (360 MHz, CDCl$_3$) δ 1.22–1.39 (1H, m), 1.49–1.58 (1H, m), 1.72–1.83 (1H, m), 1.92 (1H, bd, J 12.7 Hz), 2.59–2.68 (2H, m), 2.92 (3H, s), 3.53 (1H, dd, J 10.2, 4.7 Hz), 3.72 (1H, dd, J 10.2, 6.6 Hz), 4.12–4.22 (3H, m), 4.49 (1H, d, J 1.5 Hz), 4.58 (2H, s), 4.97 (1H, dd, J 6.6, 4.7 Hz), 7.18–7.39 (12H, m), 7.62 (1H, s).

DESCRIPTION 30

(2R,3R,4R,8S)-2-(2-Benzyloxy-1-(1-(3,5-bis(trifluoromethyl)phenyl)ethyl)oxy)-3-phenyl-4-(methanesulfonyloxymethyl)-3,4,5,6-tetrahydropyran The title compound was prepared from the compound of Description 26 by a method analogous to that described in Example 6.

$^1$H NMR (400 MHz, CDCl$_3$) δ 1.66–1.88 (2H, m), 2.15–2.28 (1H, m), 2.63 (1H, dd, J 11.6, 8.2 Hz), 2.83 (3H, s), 3.41 (1H, dd, J 10.2, 5.9 Hz), 3.56 (1H, td, J 11.9, 2.4 Hz), 3.68 (1H, dd, J 10.2, 5.6 Hz), 3.81 (1H, dd, J 9.8, 6.8 Hz), 3.96 (1H, dd, J 9.8, 3.4 Hz), 4.18 (1H, ddd, J 11.8, 4.6, 1.8 Hz), 4.31 (11H, d, J 8.2 Hz), 4.44 (1H, d, J 12.2 Hz), 4.50 (1H, d, J 12.2 Hz), 5.02 (1H, t, J 5.7 Hz), 7.03–7.15 (4H, m), 7.19–7.32 (9H, m), 7.68 (1H, s).

DESCRIPTION 31

(2R,3R,4S,8S)-2-(2-Benzyloxy-1-(1-(3,5-bis(trifluoromethyl)phenyl)ethyl)oxy)-3-phenyl-4-(2-methanesulfonyloxyethyl)-3,4,5,6-tetrahydropyran The title compound was prepared from the compound of Description 27 by a method analogous to that described in Example 6.

$^1$H NMR (360 MHz, CDCl$_3$) δ 1.32–1.56 (2H, m), 1.59–1.72 (1H, m), 1.81 (1H, dd J 13.4, 1.6 Hz), 1.69–2.02 (1H, m), 2.45 (1H, dd J 11.4, 8.4 Hz), 2.85 (3H, s), 3.41 (1H, dd J 10.1, 5.9 Hz), 3.54 (1H, td, J 11.9, 1.8 Hz), 3.67 (1H, dd, J 10.1, 5.5 Hz), 3.97 (2H, m), 4.15 (1H, dd J 12.1, 3.5 Hz), 4.27 (1H, d, J 8.3 Hz), 4.43 (1H, d, J 12.2 Hz), 4.49 (1H, d J 12.2 Hz), 5.00 (1H, t, J 5.8 Hz), 7.01 (2H, m), 7.09–7.31 (10H, m), 7.68 (1H, s).

DESCRIPTION 32

(3R)-(+)-Ethyl 3-Methylpiperidine-3-carboxylate (±)-Ethyl 3-methylpiperidine-3-carboxylate hydrochloride (53 g, 0.25 mol; Description 16 (iii)) was partitioned between dichloromethane and aqueous potassium carbonate (pH 10). The aqueous phase was extracted (twice) with dichloromethane and the combined organic phases were washed with saturated brine and dried (MgSO$_4$). The solvent was removed in vacuo and to a solution of the residue dissolved in 20% ethyl acetate/propan-2-ol (200 ml) was added a solution of D-dibenzoyl tartaric acid (22.8 g, 0.064 mol) in 20% ethyl acetate/propan-2-ol (200 ml). After partial evaporation (to approximately 300 ml) the solution was cooled (+5° C.) to give the crystalline (D)-dibenzoyl tartrate salt (24.5 g) mp 178–180° C.

The salt was partitioned between dichloromethane and aqueous potassium carbonate (pH 10) as above to give the free base as an oil [α]$_D$=+9.0° (c=1 MeOH) chiral hplc Chiralpak AD (250×4.6 mm) 10% ethanol in hexane; 1 ml/min, 210 nm: >99% ee MS m/z 172 (M+H, 100%).

A sample of this material was crystallised as the hydrochloride salt from ethyl acetate-methanol as colourless needles 143–144° C. [α]$_D$=−5.0° (c=1 MeOH)

$^1$H NMR (400 MHz, MeOH-d$_4$) δ 1.26 (3H, s), 1.30 (3H, d J 7.1 Hz), 1.58–1.64 (2H, m), 1.85–1.88 (1H, m), 2.18–2.23 (1H, m), 2.85 (1H, d J 12.9 Hz), 2.91–2.98 (1H, m), 3.23–3.31 (1H, m), 3.59 (1H, br d J 12.9 Hz), 4.19–4.31 (2H, m). MS m/z 172 (M+H, 100%).

DESCRIPTION 33

(3S)-(−)-Ethyl 3-Methylpiperidine-3-carboxylate

The title compound was prepared by the procedure of Description 32 using L-dibenzoyl tartaric acid as resolving agent.

DESCRIPTION 34

N-[(2R,3R,4R,8R)-2-(1-(3,5-bis(Trifluoromethyl)phenyl)ethoxy)-3-phenyl-3,4,5,6-tetrahydropyran-4-ylmethylene]-N'-(1-amino-2-chloroethylidene)hydrazine

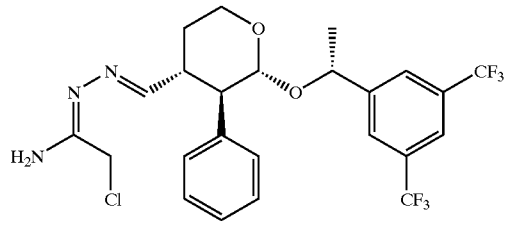

i) The aldehyde of Example 45 (1.0 g) was dissolved in methanol (5 ml), N,N-dimethylhydrazine was added and the resulting solution was stirred overnight. The solution was concentrated in vacuo to afford the desired N,N'-dimethylhydrazone as a clear oil which crystallised on standing. MS (ES$^+$) m/z 489 (M+H, 100%), 231 (M+H−257, 50%).

ii) The compound of step (i) above (1.1 g) was dissolved in ethanol (9 ml) and hydrazine hydrate (1 ml, excess), was added. The solution was heated at 80° C. for 12 hours. The resulting solution was concentrated in vacuo to afford the unsubstituted hydrazone as a clear oil. MS (ES$^+$) m/z 461 (M+H, 10%), 203 (M+H−257, 100%).

iii) The compound of step (ii) above (1.0 g) was dissolved in methanol and 2-chloroacetimidate (8 ml×0.3M solution in methanol) was added at room temperature. After 10 min the solution was concentrated in vacuo and the resulting solution was dispersed between ethyl acetate and water. The organic phase was washed with brine, dried (MgSO$_4$) and concentrated in vacuo. The residue was purified by chromatography on silica using 10–50% ethyl acetate in hexane. This afforded the title compound as a colourless solid, 300 mg. MS (ES$^+$) m/z 536 (M+H, 10%) 278 (M+H−257, 100%).

EXAMPLE 1

(2RS,3SR,4RS,8RS)-2-(1-(1-(3,5-bis (Trifluoromethyl)phenyl)ethyl)oxy)-3-phenyl-4-vinyltetrahydropyran; and (2RS,3RS,4SR,8RS)-2-(1-(1-(3,5-bis(Trifluoromethyl)phenyl)ethyl)oxy)-3-phenyl-4-vinyltetrahydropyran A solution of the mixture of lactol isomers of trans 3-phenyl-4-vinyltetrahydropyran-2-ol (Description 11; 7.4 g) and (±) 1-(3,5-bis(trifluoromethyl)phenyl)ethanol (10 g) in dichloromethane was stirred with Amberlyst™ 15 resin (10 g) and 3 Å molecular sieves (10 g) for 16 hours. The solution was filtered, evaporated to dryness and the residue purified by column chromatography on silica gel (eluting with a increasing amounts of dichloromethane in isohexane, 0–20%).

Isomer 1

(2R/S/3S/R,4R/S,8R/S)3,4-trans-2,3-cis (earlier eluting) isomer: $^1$H NMR (400 MHz, CDCl$_3$) δ 1.45 (3H, d J 6.6 Hz), 1.75 (1H, qd J 12.3 Hz and 4.9 Hz), 2.71 (1H, dd J 12.0 Hz and 3.1 Hz), 3.14 (1H, m), 3.76 (1H, dd J 11.3 Hz and 4.0 Hz), 4.06 (1H, td J 13.3 Hz and 2.52 Hz), 4.48 (1H, d J 3.08 Hz), 4.86 (2H, m), 4.97 (1H, d J 17.2 Hz), 5.52 (1H, m), 7.27–7.18 (7H, m), 7.59 (1H, s).

Isomer 2 and 3

(approximately 1:1 mixture of isomers with undetermined relative stereochemistry): $^1$H NMR (400 MHz, CDCl$_3$) δ 1.00 (3H, d J 6.5 Hz), 1.07 (3H, d J 6.4 Hz), 1.72 (4H, m), 2.55 (1H, dd J 11.5 Hz and 7.9 Hz), 2.62 (1H, m), 2.81 (1H, dd J 12.0 Hz and 3.2 Hz), 3.02 (1H, m), 3.60 (2H, m), 3.75 (1H, td J 11.3 Hz and 3.8 Hz), 4.07 (1H, dm J approx. 11.4 Hz), 4.59 (1H, d J 8.0 Hz), 4.67 (1H, q J 6.41 Hz), 4.73 (1H, q J 6.4 Hz), 4.82–4.97 (5H, m), 5.47–5.57 (2H, m), 7.20–7.65 (12H, m), 7.65 (2H, s), 7.71 (1H, s), 7.77 (2H, s), 7.78 (1H, s).

Isomer 4

(2R/S,3R/S,4S/R,8R/S)3,4-trans-2,3-trans (later eluting) isomer: $^1$H NMR (360 MHz, CDCl$_3$) δ 1.36 (3H, d J 6.6 Hz), 1.73–1.67 (2H, m), 2.55–2.42 (2H, m), 362–3.55 (1H, m), 4.13 (1H, dt J 11.8 Hz and 3.6 Hz), 4.23 (1H, d J 8.0 Hz), 4.77 (1H, d, J 2.2 Hz), 4.81 (1H, apparent s), 4.96 (1H, q J 6.6 Hz), 4.48 (1H, m), 6.99–7.02 (2H, m), 7.25–7.18 (5H, m), 7.66 (1H, s).

EXAMPLE 2

(2RS,3SR,4SR,8RS)-2-(1-(1-(3,5-bis (Trifluoromethyl)phenyl)ethyl)oxy)-4-hydroxymethyl-3-phenyltetrahydropyran Method 1

The compound of Description 8 (530 mg) was dissolved in THF (5 ml) and tetrabutylammonium fluoride (1.1 ml, 1M in THF) was added and the resulting brown solution was stirred at room temperature overnight. The solution was concentrated in vacuo and the residue was diluted with water and was extracted with ethyl acetate (3×10 ml). The organic extracts were combined and were washed with brine, dried (MgSO$_4$) and evaporated. The residue was purified on silica using 20–25% ethyl acetate in hexane as eluant to afford the title compound as a colourless oil (408 mg). $^1$H NMR (360 MHz, CDCl$_3$) δ 1.07 (1H, t, J 5.4 Hz), 1.46 (3H, d, J 6.6 Hz), 1.66–1.80 (1H, m), 1.92–2.00 (1H, m), 2.58–2.72 (1H, m), 2.75 (1H, dd, J 12.0, 3.0 Hz), 3.27–3.32 (1H, m), 3.48–3.52 (1H, m), 3.79 91H, dd, J 11.1, 3.6 Hz), 4.06 (1H, t app, J 10.8 Hz), 4.46 (1H, d, J 3.1 Hz), 4.89 (1H, q, J 6.6 Hz), 7.22 (2H, s), 7.25–7.29 (5H, m), 7.60 (1H, s).

Method 2

(2RS,3SR,4RS,8RS)-2-(1-(1-(3,5-Bis(trifluoromethyl) phenyl)ethyl)oxy)-3-phenyl-4-vinyltetrahydropyran (3,4-trans-2,3-cis; isomer 1; Example 1; 2.41 g) was dissolved in dichloromethane (30 ml) and methanol (30 ml). This solution was cooled to −78° C. under an inert atmosphere and through the solution was bubbled ozone until the solution produced a persistent blue colouration. The solution was then purged with nitrogen followed by careful addition of sodium borohydride (1.02 g). The solution was stirred at room temperature for 1 hour and then evaporated to dryness. The residue was partitioned between ethyl acetate and water and the organic phase was washed further with brine and the dried (MgSO$_4$). After removal of the solvent in vacuo the residue was purified by chromatography on silica (eluting with increasing concentrations (5–15%) of ethyl acetate in isohexane). $^1$H NMR (360 MHz, CDCl$_3$) δ 1.07 (1H, t, J 5.4 Hz), 1.46 (3H, d, J 6.6 Hz), 1.66–1.80 (1H, m), 1.92–2.00 (1H, m), 2.58–2.72 (1H, m), 2.75 (1H, dd, J 12.0, 3.0 Hz), 3.27–3.32 (1H, m), 3.48–3.52 (1H, m), 3.79 91H, dd, J 11.1, 3.6 Hz), 4.06 (1H, t app, J 10.8 Hz), 4.46 (1H, d, J 3.1 Hz), 4.89 (1H, q, J 6.6 Hz), 7.22 (2H, s), 7.25–7.29 (5H, m), 7.60 (1H, s).

EXAMPLE 3

(2RS,3SR,4SR,8RS)-2-(1-(1-(3,5-bis (Trifluoromethyl)phenyl)ethyl)oxy)-4-(methanesulfonyloxy)methyl-3-phenyltetrahydropyran The compound of Example 2 (350 mg) was dissolved in dichloromethane and triethylamine (195 μl) was added. Methanesulfonyl chloride (99 μl) was added dropwise and the mixture was stirred for 30 minutes. The mixture was washed with water, brine and dried (MgSO$_4$) and concentrated in vacuo to afford the title compound as a colourless oil (420 mg). $^1$H NMR (400 MHz, CDCl$_3$) δ 1.46 (3H, d, J 6.6 Hz), 1.79 (1H, dddd, J 12.0, 12.0, 12.0, 5.1 Hz), 1.98 (1H, d br), 2.77 (3H, s), 2.77 (1H, dd, J 12.0, 3.1 Hz), 2.87–2.97 (1H, m), 3.78–3.85 (2H, m), 4.02–4.10 (2H, m), 4.47 (1H, d, J 3.1 Hz), 4.89 (1H, q, J 6.6 Hz), 7.20 (2H, s), 7.23–7.34 (5H, m), 7.60 (1H, s).

EXAMPLE 4

(2R,3S,4R,8R)-2-(1-(1-(3,5-bis(Trifluoromethyl) phenyl)ethyl)oxy)-3-phenyl-4-vinyltetrahydropyran; and (2R,3R,4S,8R)-2-(1-(1-(3,5-bis (Trifluoromethyl)phenyl)ethyl)oxy)-3-phenyl-4-vinyltetrahydropyran A solution of the mixture of lactol isomers of trans 3-phenyl-4-vinyltetrahydropyran-2-ol (Description 11; 15.8 g) and (R)-1-(3,5-bis(trifluoromethyl)phenyl)ethanol (20 g) in dichloromethane (200 ml) was stirred with Amberlyst™ 15 resin (5 g) and 3 Å molecular sieves (15 g) for 72 hours. The solution was filtered, evaporated to dryness and the residue purified by column chromatography on silica gel (eluting with increasing amounts of dichloromethane in isohexane, 0–20%).

Isomer 1

(2R,3S,4R,8R)3,4-trans-2,3-cis (earlier eluting) isomer: $^1$H NMR (400 MHz, CDCl$_3$) δ 1.45 (3H, d J 6.6 Hz), 1.75 (1H, qd J 12.3 Hz and 4.9 Hz), 2.71 (1H, dd J 12.0 Hz and 3.1 Hz), 3.14 (1H, m), 3.76 (1H, dd J 11.3 Hz and 4.0 Hz), 4.06 (1H, td J 13.3 Hz and 2.52 Hz), 4.48 (1H, d J 3.08 Hz), 4.86 (2H, m), 4.97 (1H, d J 17.2 Hz), 5.52 (1H, m), 7.27–7.18 (7H, m), 7.59 (1H, s).

Isomer 2 and 3

(approximately 1:1 mixture of isomers with undetermined relative stereochemistry): $^1$H NMR (400 MHz, CDCl$_3$) δ 1.00 (3H, d J 6.5 Hz), 1.07 (3H, d J 6.4 Hz), 1.72 (4H, m), 2.55 (1H, dd J 11.5 Hz and 7.9 Hz), 2.62 (1H, m), 2.81 (1H, dd J 12.0 Hz and 3.2 Hz), 3.02 (1H, m), 3.60 (2H, m), 3.75 (1H, td J 11.3 Hz and 3.8 Hz), 4.07 (1H, dm J approx. 11.4 Hz), 4.59 (1H, d J 8.0 Hz), 4.67 (1H, q J 6.41 Hz), 4.73 (1H, q J 6.4 Hz), 4.82–4.97 (5H, m), 5.47–5.57 (2H, m), 7.20–7.65 (12H, m), 7.65 (2H, s), 7.71 (1H, s), 7.77 (2H, s), 7.78 (1H, s).

Isomer 4

(2R,3R,4S,8R)3,4-trans-2,3-trans (later eluting) isomer: $^1$H NMR (360 MHz, CDCl$_3$) δ 1.36 (3H, d J 6.6 Hz), 1.73–1.67 (2H, m), 2.55–2.42 (2H, m), 3.62–3.55 (1H, m), 4.13 (1H, dt J 11.8 Hz and 3.6 Hz), 4.23 (1H, d J 8.0 Hz), 4.77 (1H, d, J 2.2 Hz), 4.81 (1H, apparent s), 4.96 (1H, q J 6.6 Hz), 4.48 (1H, m), 6.99–7.02 (2H, m), 7.25–7.18 (5H, m), 7.66 (1H, s).

EXAMPLE 5

(2R,3S,4S,8R)-2-(1-(1-(3,5-bis(Trifluoromethyl) phenyl)ethyl)oxy)-4-hydroxymethyl-3-phenyltetrahydropyran (2R,3S,4S,8R)2-(1-(3,5-bis(trifluoromethyl)phenyl) ethyl-1-oxy)-3-phenyl-4-vinyltetrahydropyran (3,4-trans-2, 3-cis isomer1; Example 4; 3.95 g) was dissolved in dichloromethane (40 ml) and methanol (40 ml). This solution was cooled to –78° C. under an inert atmosphere and through the solution was bubbled ozone until the solution produced a persistent blue colouration. The solution was then purged with nitrogen followed by careful addition of sodium borohydride (1.68 g). The solution was stirred at room temperature for 1 hour and then evaporated to dryness. The residue was partitioned between ethyl acetate and water and the organic phase was washed further with brine and the dried (MgSO$_4$). After removal of the solvent in vacuo the residue was purified by chromatography on silica (eluting with increasing concentrations (5–15%) of ethyl acetate in isohexane). $^1$H NMR (360 MHz, CDCl$_3$) δ 1.07 (1H, t, J 5.4 Hz), 1.46 (3H, d, J 6.6 Hz), 1.66–1.80 (1H, m), 1.92–2.00 (1H, m), 2.58–2.72 (1H, m), 2.75 (1H, dd, J 12.0, 3.0 Hz), 3.27–3.32 (1H, m), 3.48–3.52 (1H, m), 3.79 91H, dd, J 11.1, 3.6 Hz), 4.06 (1H, t app, J 10.8 Hz), 4.46 (1H, d, J 3.1 Hz), 4.89 (1H, q, J 6.6 Hz), 7.22 (2H, s), 7.25–7.29 (5H, m), 7.60 (1H, s).

EXAMPLE 6

(2R,3S,4S,8R)-2-(1-(1-(3,5-bis(Trifluoromethyl) phenyl)ethyl)oxy)-4-(methanesulfonyloxy)methyl-3-phenyltetrahydropyran The compound of Example 5 (2.63 mg) was dissolved in dichloromethane (20 ml) and triethylamine (1.23 ml) was added. Methanesulfonyl chloride (0.68 ml) was added dropwise and the mixture was stirred for 1 hour. The mixture was washed with water, brine and dried (MgSO$_4$) and concentrated in vacuo to afford the title compound as a colourless oil (3.18 g). $^1$H NMR (400 MHz, CDCl$_3$) δ 1.46 (3H, d, J 6.6 Hz), 1.79 (1H, dddd, J 12.0, 12.0, 12.0, 5.1 Hz), 1.98 (1H, d br), 2.77 (3H, s), 2.77 (1H, dd, J 12.0, 3.1 Hz), 2.87–2.97 (1H, m), 3.78–3.85 (2H, m), 4.02–4.10 (2H, m), 4.47 (1H, d, J 3.1 Hz), 4.89 (1H, q, J 6.6 Hz), 7.20 (2H, s), 7.23–7.34 (5H, m), 7.60 (1H, s).

EXAMPLE 7

(2RS,3SR,4SR,8RS)-4-Azidomethyl-2-(1-(1-(3,5-bis (trifluoromethyl)phenyl)ethyl)oxy)-3-phenyltetrahydropyran The compound of Example 3 (280 mg) was dissolved in dimethylsulfoxide (1 ml) and sodium azide (132 mg) was added. The mixture was heated at 50° C. for 3 hours. The mixture was cooled, diluted with water (10 ml) and this suspension was extracted with ether (4×10 ml) until the aqueous layer was clear. The ethereal extracts were combined and washed with brine, dried (MgSO$_4$) and concentrated in vacuo to give the title compound as a clear oil (180 mg). $^1$H NMR (360 MHz, CDCl$_3$) δ 1.46 (3H, d, J 6.6 Hz), 1.62–1.76 (1H, m), 1.90–1.95 (1H, m), 2.64–2.76 (2H, m), 2.94 (1H, dd, J 12.2, 7.0 Hz), 3.24 (1H, dd, J 11.3, 3.7 Hz), 4.04 (1H, t, J 10.8 Hz), 4.46 (1H, d, J 2.4 Hz), 4.88 (1H, q, J 6.6 Hz), 7.21 (2H, s), 7.24–7.32 (5H, m), 7.60 (1H, s).

EXAMPLE 8

(2RS,3SR,4SR,8RS)-4-Aminomethyl-2-(1-(1-(3,5-bis(trifluoromethyl)phenyl)ethyl)oxy)-3-phenyltetrahydropyran The compound of Example 7 (180 mg) was dissolved in 2-propanol (10 ml) and palladium (10% on carbon) was added. This mixture was shaken at 40 psi hydrogen for 2 hours. The mixture was filtered to remove catalyst and the filtrate was concentrated to give the title compound as an oil. $^1$H NMR (360 MHz, CDCl$_3$) δ 1.38 (3H, d, J 6.6 Hz), 1.50 (1H, dddd, 12.8, 12.8, 12.8, 5.0 Hz), 1.85–1.89 (1H, m), 2,25 (1H, dd, J 12.6, 7.8 Hz), 2.39–2.47 (1H, m), 2.54 (1H, dd, J 12.7, 3.1 Hz), 2.59 (1H, dd, J 12.0, 3.2 Hz), 3.72 (1H, dd, J 11.1, 4.0 Hz), 4.00 (1H, ddd, J 13.2, 13.2, 2.4 Hz), 4.37 (1H, d, J 3.1 Hz), 4.81 (1H, q, J 6.6 Hz), 7.14 (2H, s), 7.16–7.24 (5H, m), 7.52 (1H, s). MS (ES$^+$) m/z 448 (M+1, 100%).

EXAMPLE 9

(2RS,3SR,4SR,8RS)-2-(1-(1-(3,5-bis (Trifluoromethyl)phenyl)ethyl)oxy)-4-(dimethylamino)methyl-3-phenyltetrahydropyran The compound of Example 8 (150 mg) was dissolved in isopropanol (10 ml) and aqueous formaldehyde (2 ml), chloroform (30 µl) and palladium hydroxide on carbon (50 mg, 10%) was added to the solution. This mixture was hydrogenated at 40 psi for 4 hours. The mixture was filtered to remove the catalyst, the filtrate was evaporated and dissolved in ethyl acetate and washed with potassium carbonate (aqueous solution), dried (MgSO$_4$) and concentrated. The residue was purified on silica using medium pressure chromatography with 0.5% aqueous ammonia, 10% methanol in dichloromethane as eluant. This afforded the title compound as a clear oil. $^1$H NMR (360 MHz, CDCl$_3$) δ 1.45 (3H, d, J 6.6 Hz), 1.46–1.52 (1H, m), 1.95–2.05 (1H, m), 2.10–2.26 (2H, m), 2.19 (6H, s), 2.56 (1H, dd, J 11.9, 3.0 Hz), 2.59–2.68 (1H, m), 3.76 (1H, ddd, J 11.1, 4.8, 1.0 Hz), 4.02 (1H, ddd, J 11.4, 11.4, 2.4 Hz), 4.42 (1H, d, J 3.0 Hz), 4.88 (1H, q, J 6,6 Hz), 7.19 (2H, s), 7.21–7.31 (5H, m), 7.59 (1H, s). MS (ES$^+$) m/z 476 (M+1, 100%).

EXAMPLE 10

(2RS,3SR,4SR,8RS)-2-(1-(1-(3,5-bis (Trifluoromethyl)phenyl)ethyl)oxy)-4-(pyrrolidin-1-yl)methyl-3-phenyltetrahydropyran Hydrochloride Salt The compound of Example 3 (0.2 g) was dissolved in pyrrolidine (2 ml) and the solution heat (60° C.) for 1 hour. The solution was evaporated to dryness and the residue purified by chromatography on silica (eluting with increasing proportions of methanol/aqueous ammonia (100:4) in dichloromethane 0–10%). The product was evaporated to dryness, dissolved in diethyl ether (1 ml) and to this solution was added 1M-HCl in diethyl ether (1 equivalent). The crystals which formed were removed by filtration and dried in vacuo to give the title compound. mp 206° C.; $^1$H NMR (400 MHz, CDCl$_3$) δ 1.49 (3H, d J 6.6 Hz), 1.67 (1H, qd J 11.0 Hz and 4.84 Hz), 1.94 (2H, m), 2.30 (2H, m), 2.63 (4H, m), 2.84 (2H, m), 2.94 (1H, d J 14.9 Hz), 3.83 (3H, m), 4.04 (1H, t J 11.6 Hz), 4.44 (1H, d J 3 Hz), 4.89 (1H, q J 6.64 Hz), 7.20 (2H, s), 7.20–7.34 (5H, m), 7.60 (1H, s), 12.16 (1H, s).

Examples 11, 12, 15, 16, 17 (Table 1) were prepared by a procedure analogous to that described for Example 10 using either the single enantiomer Example 6 or the racemic mesylate Example 3 as the starting material.

EXAMPLE 13

(2RS,3SR,4SR,8RS)-2-(1-(1-(3,5-bis (Trifluoromethyl)phenyl)ethyl)oxy)-4-(1,2,4-triazol-1-yl)methyl-3-phenyltetrahydropyran The compound of Example 3 (0.2 g) was dissolved in dimethylformamide (4 ml) and to this solution was added 1,2,4-triazole (0.052 g). The solution was heated (60° C.) for 1 hour. The cooled solution was dispersed between ethyl acetate and water. The organic phase was washed with water a further three times, saturated brine and dried (MgSO$_4$). After removal of the solvent in vacuo the residue was purified by chromatography on silica (eluting with increasing proportions of methanol/aqueous ammonia (100:4) in dichloromethane 0–10%). $^1$H NMR (400 MHz, CDCl$_3$) δ 1.45 (3H, s), 1.62 (2H, m), 2.66 (1H, dd J 12.2 Hz and 3.1 Hz), 3.09 (1H, m), 3.74 (2H, m), 3.98 (1H, m), 4.08 (1H, dd J 13.9 Hz and 3.6 Hz), 4.46 (1H, d J 3.1 Hz), 4.86 (1H, q J 6.6 Hz), 7.19 (2H, s), 7.26–7.37 (5H, m), 7.60 (1H, s), 7.76 (1H, s), 7.94 (1H, s).

Examples 14, 18, 19 (Table 1) were prepared by a procedure analogous to that described for Example 13 using either the single enantiomer Example 6 or the racemic mesylate Example 3 as the starting material.

EXAMPLE 20

(2RS,3SR,4SR,8RS)-2-(1-(1-(3,5-bis (Trifluoromethyl)phenyl)ethyl)oxy)-4-(2-hydroxyethyl)-3-phenyltetrahydropyran To a cooled (−20° C.) solution of the compound of Example 1 (isomer 1, 486 mg) in tetrahydrofuran (10 ml) was added dropwise a solution of borane. tetrahydrofuran complex (3.28 ml, 1M in tetrahydrofuran) and the reaction allowed to warm to room temperature. After stirring for 30 minutes, the reaction was re-cooled and a premixed solution of 2M sodium hydroxide (4 ml) and 1 ml of 30% hydrogen peroxide was added slowly. The reaction was partitioned between ethyl acetate and water and the combined organics dried (brine, MgSO$_4$) and concentrated under reduced pressure to yield 520 mg of crude colourless oil. This was purified on silica eluting with 30% ethyl acetate/isohexane to afford the desired product as a colourless oil (328 mg). $^1$H NMR (CDCl$_3$, 360 MHz): δ 1.05 (1H, t, J 5.4 Hz), 1.08–1.18 (1H, m), 1.45 (3H, d, J 6.6 Hz), 1.50–1.58 (2H, m), 1.95 (1H, br d, J 12.8 Hz), 2.60–2.64 (2H, m), 3.58–3.64 (2H, m), 3.74 (1H, ddd, J 11.2, 4.9, 1.4 Hz), 4.00–4.07 (1H, m), 4.44 (1H, d, J 1.9 Hz), 4.87 (1H, q, J 6.5 Hz), 7.20–7.30 (7H, m), 7.59 (1H, s).

EXAMPLE 21

(2RS,3SR,4RS,8RS)-2-(1-(1-(3,5-bis (Trifluoromethyl)phenyl)ethyl)oxy)-4-(2-methanesulfonyloxy)ethyl-3-phenyltetrahydropyran The compound of Example 20 (1.6 g) was dissolved in dichloromethane (0° C.) (3.5 ml) and triethylamine (0.67 ml) was added. Methanesulfonyl chloride (0.35 ml) was added dropwise and the mixture was stirred for 45 minutes. Further addition of triethylamine (0.13 ml) and methanesulfonyl chloride (0.24 ml) was made and after 5 minutes the solvent was removed in vacuo. The residue was dissolved in ethyl acetate and the solution was washed with water, brine and dried (MgSO$_4$) and concentrated in vacuo to afford the title compound as a colourless oil (1.6 g). $^1$H NMR (CDCl$_3$, 360 MHz): δ 1.27–1.34 (1H, m), 1.46 (3H, d, J 6.6 Hz), 1.50–1.52 (1H, m), 1.54–1.56 (1H, m), 1.93–1.96 (1H, m), 2.60–2.65 (2H, m), 2.93 (3H, s), 3.76 (1H, dd, J 11.2, 4.7 Hz), 4.03 (1H, t, J 11.2 Hz), 4.10–4.18 (2H, m), 4.44 (1H, br s), 4.87 (1H, q, J 6.6 Hz), 7.17 (2H, s), 7.20–7.31 (5H, m), 7.60 (1H, s).

EXAMPLE 22

(2R,3S,4S,8R)-2-(1-(1-(3,5-bis(Trifluoromethyl) phenyl)ethyl)oxy)-4-(2-hydroxyethyl)-3-phenyltetrahydropyran The title compound was prepared from the compound of Example 4 (isomer 1) by a procedure analogous to that described in Example 20. $^1$H NMR (CDCl$_3$, 360 MHz): δ 1.05 (1H, t, J 5.4 Hz), 1.08–1.18 (1H, m), 1.45 (3H, d, J 6.6 Hz), 1.50–1.58 (2H, m), 1.95 (1H, br d, J 12.8 Hz), 2.60–2.64 (2H, m), 3.58–3.64 (2H, m), 3.74 (1H, ddd, J 11.2, 4.9, 1.4 Hz), 4.00–4.07 (1H, m), 4.44 (1H, d, J 1.9 Hz), 4.87 (1H, q, J 6.5 Hz), 7.20–7.30 (7H, m), 7.59 (1H, s).

EXAMPLE 23

(2R,3S,4R,8R)-2-(1-(1-(3,5-bis(Trifluoromethyl) phenyl)ethyl)oxy)-4-(2-methanesulfonyloxy)ethyl-3-phenyltetrahydropyran The title compound was prepared from the compound of Example 22 by a procedure analogous to that described in Example 21.

Examples 24, 25, 26, 27 (Table 1) were prepared from the compound of Example 21 and the appropriate amine by procedures analogous to those described in Examples 10 and 13.

Examples 28 and 29 (Table1) were prepared from the compound of Example 23 and the appropriate amine by procedures analogous to that described in Examples 10 and 13.

EXAMPLE 30

(2R,3R,4R,8R)-2-(1-(1-(3,5-bis(Trifluoromethyl)phenyl)ethyl)oxy)-4-hydroxymethyl-3-phenyltetrahydropyran The title compound was prepared from isomer 4 in Example 4 by a procedure analogous to that described in Example 5. $^1$H NMR (CDCl$_3$, 360 MHz): δ 1.07 (1H, t J 5.5 Hz), 1.37 (3H, d J 6.6 Hz), 1.63 (1H, m), 1.81 (1H, dm), 1.97 (1H, m), 2.55 (1H, dd J 11.6 Hz and 8.4 Hz), 3.26 (1H, m), 3.40 (1H, m), 3.57 (1H, td J 12.0 Hz and 2.4 Hz), 4.18 (1H, dm), 4.25 (1H, d J 8.4 Hz), 4.95 (1H, q J 6.6 Hz), 7.03 (1H, m), 7.18 (2H, s), 7.22–7.27 (3H, m), 7.66 (1H, s).

EXAMPLE 31

(2R,3R,4R,8R)-2-(1-(1-(3,5-bis(Trifluoromethyl)phenyl)ethyl)oxy)-4-(methanesulfonyloxy)methyl-3-phenyltetrahydropyran The title compound was prepared from the compound of Example 30 by a procedure analogous to that described in Example 6. $^1$H NMR (CDCl$_3$, 360 MHz): δ 1.37 (3H, d J 6.6 Hz), 1.73 (1H, qd J 11.8 Hz and 4.6 Hz), 1.83 (1H, dm, J 11.5 Hz), 2.2 (1H, m), 2.58 (1H, dd J 11.7 Hz and 8.3 Hz), 2.83 (3H, s), 3.56 (1H, td J 12 Hz and 2.5 Hz), 3.80 (1H, dd J 9.8 Hz and 6.8 Hz), 3.94 (1H, dd J 9.9 Hz and 3.4 Hz), 4.17 (1H, dm J 11.9 Hz), 4.24 (1H, d J 8.3 Hz), 4.95 (1H, q J 6.59 Hz), 7.04 (2H, m), 7.17 (2H, s), 7.27 (3H, m), 7.67 (1H, s).

Examples 32, 33, 34, 35 and 36 (Table 2) were prepared from the product of Example 31 by procedures analogous to those described in Example 10 and Example 13.

EXAMPLE 37

(2R,3R,4R,8R)-2-(1-(1-(3,5-bis(Trifluoromethyl)phenyl)ethyl)oxy)-4-(2-hydroxyethyl)-3-phenyltetrahydropyran The title compound was prepared from the product of isomer 4 in Example 4 by a procedure analogous to that described in Example 20. $^1$H NMR (400 MHz, CDCl$_3$) δ 0.91–0.93 (1H, m), 1.19–1.28 (1H, m), 1.35 (3H, d, J 6.6 Hz), 1.40–1.50 (2H, m), 1.79 (1H, d, br), 1.89–1.98 (1H, m), 2.42 (1H, dd, J 11.4, 8.6 Hz), 3.45–3.57 (3H, m), 4.14 (1H, dd, J 10.6, 4.4 Hz), 4.20 (1H, d, J 8.4 Hz), 4.94 (1H, q, J 6.5 Hz), 7.02–7.04 (2H, m), 7.17 (2H, s), 7.22–7.26 (3H, m), 7.65 (1H, s).

EXAMPLE 38

(2R,3R,4S,8R)-2-(1-(1-(3,5-bis(Trifluoromethyl)phenyl)ethyl)oxy)-4-(2-methanesulfonyloxy)ethyl-3-phenyltetrahydropyran The title compound was prepared from the product Example 22 by a procedure analogous to that described in Example 21. $^1$H NMR (360 MHz, CDCl$_3$) δ 1.35 (3H, d, J 6.6 Hz), 1.48–1.55 (2H, m), 1.61–1.71 (1H, m), 1.77–1.84 (1H, m), 1.88–2.00 (1H, m), 2.42 (1H, t, J 9.9 Hz), 2.81 (3H, s), 3.55 (1H, td, J 12.1, 2.0 Hz), 3.97–4.18 (3H, m), 4.21 (1H, d, J 8.4 Hz), 4.94 (1H, q, J 6.6 Hz), 7.01–7.03 (2H, m), 7.16 (2H, s), 7.23–7.26 (3H, m), 7.66 (1H, s).

TABLE 1

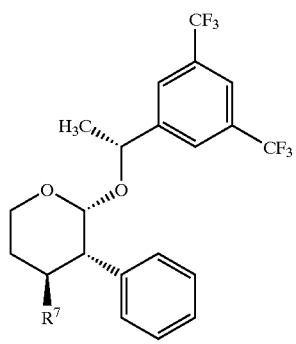

| Ex. No. | R$^7$ | Method | MS(ES$^+$) (M+H) | $^1$H NMR | Stereochemistry |
|---|---|---|---|---|---|
| 6 | Me$_2$N—CH$_2$— | from 6 | 476 | (360MHz, CDCl$_3$)δ 1.45(3H, d J 6.52Hz), 1.49(1H, bm), 1.96(2H, vbs)2.17(7H, vbs), 2.55(1H, dd J 11.7Hz and 3.1Hz), 2.61(1H, m), 3.76(1H, dd J 10.8Hz, 4.3Hz), 4.02(1H, td J 13.3Hz and 2.6Hz), 4.42(1H d J 2.8Hz), 4.87(1H, q J 6.7Hz), 7.19–7.31(7H, m), 7.59(1H, s). | 2R, 3S, 4S, 8R |
| 7 | N$_3$—CH$_2$— | from 3 | | (360MHz, CDCl$_3$)δ 1.46(3H, d, J 6.6Hz), 1.62–1.76(1H, m), 1.90–1.95(1H, m), 2.64–2.76(2H, m), 2.94)1H, dd, J 12.2, 7.0Hz), 3.24(1H, dd, J 11.3, 3.7Hz), 4.04(1H, t, J 10.8Hz), 4.46(1H, d, J 2.4Hz), 4.88(1H, q, J 6.6Hz), 7.21 (2H, s), 7.24–7.32(5H, m), 7.60(1H, s). | (±)2R/S, 3S/R, 4S/R, 8R/S |
| 10 HCl salt | ⟨pyrrolidine⟩N—CH$_2$— | from 3 | 502 | (400MHz, CDCl$_3$)δ 1.47(3H, d J 6.6Hz), 1.67 (1H, bq), 1.94(2H, bd J 7.56Hz), 2.29(2H, bd J 6.24Hz), 2.60(4H bdd), 2.88(3H m), 3.83(3H bdd J 11.32Hz and 4.44Hz), 4.03(1H, t J 11.2Hz), 4.44(1H, d J 3.0Hz), 4.89(1H, q J 6.56Hz), 7.19–7.34(7H, m), 7.60(1H, s), 12.19(1H, bs). | (±)2R/S, 3S/R, 4S/R, 8R/S |

TABLE 1-continued

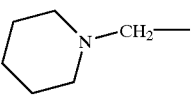

| Ex. No. | R⁷ | Method | MS(ES⁺) (M+H) | ¹H NMR | Stereochemistry |
|---|---|---|---|---|---|
| 11 HCl salt | piperidinyl-CH₂— | from 3 | 516 | (400MHz, CDCl₃)δ 1.35(1H, vbq), 1.48(3H, d J 6.6Hz), 1.69(3H, vbm), 1.83(1H, vbd), 2.33–2.67(7H, vbm), 2.98(2H, vbm), 3.37(1H, vbs), 3.63(1H, vbs), 3.81(1H, dd J 11.36Hz and 4.32Hz), 4.03(1H, t J 11.6Hz), 4.45(1H, 3.0Hz), 4.89(1H, 6.6Hz), 7.19–7.33(7H, m), 7.60(1H, s), 11.90(1H, s). | (±)2R/S, 3S/R, 4S/R, 8R/S |
| 12 free base | azetidinyl-CH₂— | from 3 | 488 | (360MHz, CDCl₃): δ 1.43–1.56(4H, m), 1.97–2.05(4H, m), 2.21(1H, dd, J 12.0, 2.9Hz), 2.45–2.52(1H, m), 2.57 (1H, dd, J 12.0, 3.1Hz), 3.07–3.15(4H, m), 3.71–3.76(1H, m), 3.96–4.03(1H, m), 4.40(1H, d, J 3.1Hz), 4.86(1H, q, J 6.6Hz), 7.18–7.31(7H, m), 7.59(1H, s). | (±)2R/S, 3S/R, 4S/R, 8R/S |
| 13 | 1,2,4-triazolyl-CH₂— | from 3 | 500 | (400MHz, CDCl₃)δ 1.45(3H, d J 6.6Hz), 1.63(2H, m), 2.65(1H, dd J 12.2Hz and 3.1Hz), 3.08(1H, m), 3.75(2H, m), 3.97(1H, m), 4.00(1H, dd J 13.9Hz and 3.6Hz), 4.46(1H, d J 3.1Hz), 4.87(1H, q J 6.6Hz). 7.9(2H, s), 7.26–7.36(5H, m). 7.60(1H, s), 7.76(1H, s), 7.93(1H, s). | (±)2R/S, 3S/R, 4S/R, 8R/S |
| 14 free base | imidazolyl-CH₂— | from 3 | 499, 100% | (400MHz, CDCl₃): δ 1.45(3H, d, J 6.5Hz), 1.54(1H, dddd, J 12.7, 12.7, 12.7, 4.8Hz), 1.62–1.65(1H, m), 2.63 (1H, dd, J 12.1, 2.6Hz), 2.80–2.88(1H, m), 3.54(1H, dd, J 11.3, 4.6Hz), 3.74(1H, dd, J 11.3, 4.6Hz), 3.87(1H, dd, J 14.1, 2.6Hz), 3.97(1H, t, J 11.3Hz), 4.45(1H, d, J2.6Hz), 4.87(1H, q, J 6.5Hz), 6.79(1H, s), 7.04(1H, s), 7.18(2H, s), 7.26–7.39(6H, m), 7.60(1H, s). | (±)2R/S, 3S/R, 4S/R, 8R/S |
| 15 | morpholinyl-CH₂— | from 3 | 518, 100% | (400MHz, CDCl₃): δ 1.45(3H, d, J 6.5Hz), 1.44–1.55 (1H, m), 1.91(1H, t, J 10.6Hz), 2.09–2.18(4H, m), 2.43– 2.52(2H, m), 2.53–2.69(2H, m), 2.53–2.69(2H, m), 3.61– 3.71(4H, m), 4.75(1H, dd, J 11.2, 4.6Hz), 4.00(1H, t, J 12.1Hz), 4.43(1H, br s), 4.87(1H, q, J 6.5Hz), 7.17–7.19 (4H, m), 7.23–7.28(3H, m), 7.59(1H, s). | (±)2R/S, 3S/R, 4S/R, 8R/S |
| 16 HCl salt | pyrrolidinyl-CH₂— | from 6 | 502 | (400MHz, CDCl₃)δ 1.47(3H, d J 6.6Hz), 1.67(1H, bq), 1.94(2H, bd J 7.56Hz), 2.29(2H, bd J 6.24Hz), 2.60(4H bdd), 2.88(3H m), 3.83(3H bdd J 11.32Hz and 4.44Hz), 4.03(1H, t J 11.2Hz), 4.44(1H, d J 3.0Hz). 4.89(1H, q J 6.56Hz), 7.19–7.34(7H, m), 7.60(1H, s), 12.19(1H, bs). | 2R, 3S, 4S, 8R |
| 17 | azetidinyl-CH₂— | from 6 | 488 | (360MHz, CDCl₃)δ 1.43(3H, d J 6.6Hz), 1.47(1H, vbm), 2.02(4H, bm), 2.19(1H, bm), 2.45(1H, bm), 2.57(1H, bdd), 3.11(4H, vbt), 3.72(1H, bdd), 3.99(1H, btd), 4.40(1H, d J 3.0Hz), 4.86(1H, q J 6.6Hz), 7.18–7.30(7H, m). 7.58(1H, s). | 2R, 3S, 4S, 8R |
| 18 | 1,2,4-triazolyl-CH₂— | from 6 | 500 | (400MHz, CDCl₃)δ 1.45(3H, d J 6.6Hz), 1.63(2H, m), 2.65(1H, dd J 12.2Hz and 3.1Hz), 3.08(1H, m), 3.75(2H, m), 3.97(1H, m), 4.00(1H, dd J 13.9Hz and 3.6Hz), 4.46(1H, d J 3.1Hz), 4.87(1H, q J 6.6Hz). 7.19(2H, s), 7.26–7.36(5H, m), 7.60(1H, s), 7.76(1H, s), 7.93(1H, s). | 2R, 3S, 4S, 8R |
| 19 | I—CH₂— | from 6 | — | (360MHz, CDCl₃): δ 1.45(3H, d, J 6.6Hz), 1.64(1H, dddd, J 11.6, 11.6, 11.6, 5.1Hz), 1.97(1H, br d, J 13.1Hz), 2.35–2.40(1H, m), 2.68(1H, 1H, dd, J 11.6, 3.2Hz), 2.84 (1H, dd, J 9.9, 7.6Hz), 3.19(1H,, dd, 9.9, 2.6Hz), 3.81 (1H, ddd, J 11.3, 3.8, 1.3Hz), 4.10(1H, ddd, J 13.4, 13.4, 2.5Hz), 4.41(1H, d, J 3.2Hz), 4.87(1H, q, J 6.6Hz), 7.20 (2H, s), 7.23–7.35(5H, m), 7.60(1H, s). | 2R, 3S, 4S, 8R |

TABLE 1-continued

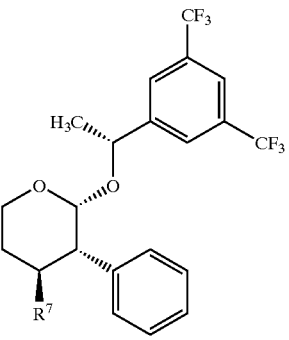

| Ex. No. | R⁷ | Method | MS(ES⁺) (M+H) | ¹H NMR | Stereochemistry |
|---|---|---|---|---|---|
| 24 free base | pyrrolidine-N-CH₂CH₂— | from 21 | 516, 100% | (400MHz, CDCl₃): δ 1.05–1.11(1H, m), 1.44(3H, d, J 6.6 Hz), 1.47–1.55(2H, m), 1.71(4H, br s), 1.93(1H, d, J 12.9 Hz), 2.15–2.52(7H, m), 2.60(1H dd, J 12.0, 3.1Hz), 3.73 (1H, dd, J 11.1, 4.6Hz), 4.03(1H, t, J 11.2Hz), 4.43(1H, d, J 2.8Hz), 4.87(1H, q, J 6.5Hz). 7.19–7.28(7H, m), 7.59(1H, s). | 2R/S, 3S/R, 4S/R, 8R/S |
| 25 HCl salt | piperidine-N-CH₂CH₂— | from 21 | 530, 100% | (400MHz, DMSO-d₆): δ 1.20–1.67(12H, m), 1.87(1H, br d, J 12.5Hz), 2.40–2.50(1H, m), 2.60–2.80(3H, m), 2.97–3.04(2H, br m), 3.20–3.27(2H, m), 3.72(1H, dd, J 10.9, 4.2Hz),, 3.90–3.98(1H, m), 4.41(1H, d, J 2.6Hz), 4.93–4.99(1H, m), 7.23–7.29(5H, m), 7.45(2H, s),7.84(1H, s), 9.20(1H, s). | 2R/S, 3S/R, 4S/R, 8R/S |
| 26 HCl salt | azetidine-N-CH₂CH₂— | from 21 | 520, 100% | (400MHz, DMSO-d₆): δ 0.95–1.10(1H, m), 1.22–1.34(1H, m), 1.33–1.46(4H, m), 1.88(1H, d, J 12.9Hz), 2.12–2.25 (1H, m), 2.25–2.34(1H, m), 2.40–2.53(1H, m), 2.65(1H, dd, J 11.9, 2.4Hz), 3.02–3.17(2H, m), 3.70–3.84(3H, m), 3.91–3.97(3H, m), 4.40(1H, d, J 2.6Hz), 4.96(1H,q, J 6.2Hz), 7.23–7.29(5H, m), 7.44(1H, s), 9.99(1H, s). | 2R/S, 3S/R, 4S/R, 8R/S |
| 27 free base | imidazol-1-yl-CH₂CH₂— | from 21 | 513, 100% | (360MHz, CDCl₃): δ 1.32–1.44(4H, m), 1.52–1.54(1H, m), 1.74–1.88(2H, m), 2.34–2.43(1H, m), 2.61(1H, dd, J 11.9, 3.2Hz), 3.75(1H, dd, J 10.7, 4.2Hz), 3.78–3.87(2H, m), 3.96–4.02(1H, m), 4.43(1H, d, J 3.2Hz), 4.85(1H, q, J 6.6Hz), 6.75(1H, s), 7.05(1H, s), 7.11–7.13(2H,m), 7.18(2H, m)7.25–7.31(3H, m), 7.36(1H, s), 7.59(1H, s). | 2R/S, 3S/R, 4S/R, 8R/S |
| 28 free base | morpholine-N-CH₂CH₂— | from 21 | 532, 100% | (360MHz, CDCl₃): δ 0.98–1.08(1H, m), 1.45(3H, d, J 6.6Hz), 1.46–1.56(2H, m), 1.89–1.93(1H, m), 2.23–2.34 (6H, m), 2.46–2.52(1H, m), 2.60(1H, dd, J 12.0, 3.2Hz), 3.65(4H, t, J 4.68), 4.02(1H, ddd, J 13.2, 13.2, 2.4Hz), 4.44(1H, d, J 3.2Hz), 4.86(1H, q, J 6.6Hz),7.19–7.29 (7H, m), 7.59(1H, s). | 2R/S, 3S/R, 4S/R, 8R/S |
| 29 free base | 1,2,4-triazol-1-yl-CH₂CH₂— | from 23 | 514, 100% | (400MHz, CDCl₃)δ 1.44(3H, d, J 6.6Hz), 1.47–1.58(2H, m), 1.81–1.92(2H, m), 2.41–2.50(1H, m), 2.62(1H, dd, J 11.9, 2.8Hz), 3.75(1H, dd J 11.4, 4.8Hz), 3.98–4.13(3H, m), 4.43(1H, d, J 2.8Hz), 4.85(1H, q, J 6.6Hz), 7.12–7.14 (2H, m), 7.19(2H, s), 7.26–7.28(3H, m), 7.59(1H, s), 7.91(2H, s). | 2R, 3S, 4S, 8R |

TABLE 2

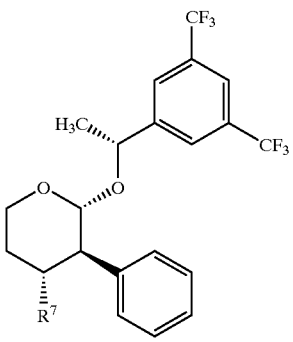

| Ex. No. | R⁷ | Method | MS(ES⁺) (M+H) | ¹H NMR | Stereochemistry |
|---|---|---|---|---|---|
| 32 | pyrrolidine-N-CH₂— | from 31 | 502 | | 2R, 3R, 4R, 8R |
| 33 HCl salt | piperidine-N-CH₂— | from 31 | 516 | (400MHz, CDCl₃)δ 1.27(1H, m), 1.35(3H, d J 6.6Hz), 1.50(1H, bd J 14Hz), 1.62(2H, vbs), 1.74(1H, bd, J 13.6Hz), 2.04(1H, m), 2.19(1H, m), 2.32(3H, vbs), 2.52(2H, m), 2.71(1H, m), 2.83(1H, d J 13.3Hz), 3.24(1H, d J 11.8Hz), 3.34(1H, d J 10.6Hz), 3.59(1H, t J 12.4Hz), 4.16(1H, dd J 11.4Hz and 3.4Hz), 4.26(1H, d J6.7Hz), 4.94(1 H, q J 6.4Hz), 7.04(2H, m), 7.16(2H, s), 7.27(3H, m), 7.67(1H, s), 1.90(1H, s). | 2R, 3R, 4R, 8R |
| 34 free base | EtOOC-piperidine-N— | from 31 | 588 | (400MHz, CDCl₃)δ 1.21(3H, t J 7.9Hz), 1.35(3H, d J 7.4Hz), 1.4(1H, m), 1.57–1.66(3H, m), 1.76(2H, m), 1.88–2.00(5H, m), 2.12(1H, m), 2.37(1H, bt J 11.2Hz), 2.56(1H, bd J 12.6Hz), 2.68(1H, m), 3.52(1H, td, J 13.3Hz and 1.7Hz), 4.08(2H, q J 7.8Hz), 4.13(1H, m), 4.17(1H, dJ 9.2Hz), 4.93(1H, q J 7.32Hz), 6.99(2H, m), 7.16(2H, s), 7.20(3H, m), 7.65(1H, s). | 2R, 3R, 4R, 8R |
| 35 | triazole-N-CH₂— | from 31 | 500 | (400MHz, CDCl₃)δ 1.36(3H, d J 6.5Hz), 2.41(1H, m), 2.49(1H, dd J 11.4Hz and 7.8Hz), 3.50(1H, td J 13.6Hz and 1.7Hz), 3.79(1H, m), 3.95(1H, dd J 13.7Hz and 3.2Hz), 4.10(1H, dd J 11.8Hz and 3.9Hz), 4.22(1H, d J 7.9Hz), 4.93(1H, q J 6.6Hz), 7.10(2H, dd J 7.4Hz and 3.2Hz), 7.15(2H, s), 7.25–7.29(5H, m), 7.66(1H, s), 7.78(1H, s), 7.87(1H, s). | 2R, 3R, 4R, 8R |
| 36 | azetidine-N-CH₂— | from 31 | 488 | | 2R, 3R, 4R, 8R |
| 39 | Me₂N-CH₂CH₂— | from 38 | 490 | (400MHz, CDCl₃)δ 1.34(3H, d, J 6.6Hz), 1.43–1.69(4H, m), 1.86(1H, d, br), 2.08–2.17(1H, m), 2.38–2.43(3H, s, br), 2.69–2.72(2H, m), 3.65(1H, t, J 11.8Hz), 4.13(1H, dd, J 11.8, 4.2Hz), 4.27(1H, d, J 8.3Hz), 4.94(1H, q, J 6.6Hz), 7.07–7.09(2H, m), 7.15(2H, s), 7.25–7.29(3H, m), 7.66(1H, s) | 2R, 3R, 4R, 8R |

EXAMPLE 40

(2R,3S,4R,8R)-2-(1-(1-(3,5-bis(Trifluoromethyl) phenyl)ethyl)oxy)-4-(2-iodoethyl)-3-phenyltetrahydropyran To a room temperature solution of the compound of Example 22 (556 mg) in diethyl ether (7.5 ml) and acetonitrile (2.5 ml) was added triphenylphosphine (322 mg), imidazole (125 mg) and iodine (467 mg) with vigorous stirring. After 1 hr, a further portion of triphenylphosphine (32 mg) was added and the reaction left for a further 16 hrs. The mixture was concentrated in vacuo and partitioned between ethyl acetate and saturated sodium thiosulfate solution. The organic phase was dried (brine, magnesium sulfate) and concentrated in vacuo before purifying on silica, using 4% diethyl ether in isohexane as eluent, to afford the title compound as a colourless oil.

¹H NMR (360 MHz, CDCl₃) δ 1.25–1.44 (2H, m), 1.46 (3H, d, J 6.6 Hz), 1.80–1.94 (2H, m), 2,51–2.64 (2H, m), 3.00–3.09 (1H, m), 3.13–3.21 (1H, m), 3.75–3.80 1H, m), 4.01–4.07 (1H, m), 4.43 (1H, d, J 2.7 Hz), 4.87 (1H, q, J 6.6 Hz), 7.19–7.33 (7H, m), 7.60 (1H, s).

EXAMPLE 41

(2R,3R,4R,8R)-2-(1-(1-(3,5-bis(Trifluoromethyl) phenyl)ethyl)oxy)-4-(iodomethyl)-3-phenyltetrahydropyran The compound of Example 31 (1 g) was dissolved in dimethoxyethane (10 ml) and sodium iodide (0.57 g) added.

The mixture was heated to reflux and stirred under an atmosphere of nitrogen for 3 hours. The mixture was cooled to room temperature, filtered through a pad of celite and concentrated in vacuo to afford an orange oil. This was purified on silica, using 20% dichloromethane in hexane as eluant, gradually increasing to 50% dichloromethane in hexane, to afford the title compound as a colourless oil.

$^1$H NMR (400 MHz, CDCl$_3$) δ 1.35 (3H, d, J 6.6 Hz), 1.59–1.64 (2H, m), 1.83 (1H, d, J 9.9 Hz), 2.54 (1H, dd, J 10.6, 8.4 Hz), 2.78 (1H, dd, J 10.0, 6.6 Hz), 3.06 (1H, dd, J 9.9, 2.5 Hz), 3.61 (1H, td, J 11.9, 2.4 Hz), 4.18 (1H, d, m, J 10.9 Hz), 4.25 (1H, d, J 8.4 Hz), 4.94 (1H, q, J 6.6 Hz), 7.04–7.06 (2H, m), 7.17 (2H, s), 7.24–7.26 (3H, m), (1H, s).

EXAMPLE 42

(2R,3R,4S,8R)-2-(1-(1-(3,5-bis(Trifluoromethyl) phenyl)ethyl)oxy)-4-(2-iodoethyl)-3-phenyltetrahydropyran Example 42 was prepared from the compound of Example 38 by a procedure analogous to that described in Example 41.

$^1$H NMR (360 MHz, CDCl$_3$) δ 1.35 (3H, d, J 6.6 Hz), 1.38–1.49 (2H, m), 1.64–1.79 (2H, m), 1.88–1.99 (1H, m), 2.44 (1H, dd, J 11.4, 8.4 Hz), 2.89–2.96 (1H, m), 3.04–3.11 (1H, m), 3.56 (1H, td, J 12.1, 2.3 Hz), 4.14 (1H, ddd, J 11.8, 4.6, 1.6 Hz), 4.20 (1H, d, J 8.4 Hz), 4.94 (1H, q, J 6.6 Hz), 7.01–7.04 (2H, m), 7.16 (2H, s), 7.22–7.26 (3H, m), 7.77 (1H, s).

EXAMPLE 43

(2R,3S,4S,8R)-2-(1-(1-(3,5-bis(Trifluoromethyl) phenyl)ethyl)oxy)-4-formyl-3-phenyltetrahydropyran The compound of Example 4 (isomer 1, 1.25 g), was dissolved in dichloromethane (50 ml) and methanol (20 ml) and the solution was cooled to −78° C. The solution was purged with ozone until a blue coloration persisted. The solution was purged with nitrogen for 10 min and dimethyl sulfide (20 ml) was added and the solution was allowed to warm to room temperature overnight. The solution was concentrated in vacuo and the residue was extracted with ethyl acetate and washed with water, brine then dried (MgSO$_4$) and concentrated in vacuo. The resulting oil was purified by chromatography on silica using 30–90% dichloromethane in isohexane as eluant. This afforded the title aldehyde as a colourless oil which crystallised on standing.

$^1$H NMR (400 MHz, CDCl$_3$) δ 1.46 (3H, d, J 6.6 Hz), 1.85 (1H, dddd, J 5.0, 12.2, 12.2, 12.2 Hz), 1.92–1.96 (1H, m), 3.09 (1H, dd, J 3.1, 12.3 Hz), 3.51 (1H, tt, J 3.0, 12.1 Hz), 3.83 (dd, J 4.8, 11.3 Hz), 4.04 (1H, dt, J 2.7, 11.8 Hz), 4.55 (1H, q, J 6.6 Hz), 7.19 (2H, s), 7.23–7.35 (5H, m), 7.62 (1H, s), 9.46 (1H, s).

EXAMPLE 44

(2R,3S,4R,8R)-2-(1-(1-(3,5-bis(Trifluoromethyl) phenyl)ethyl)oxy)-4-(2-formylmethyl)-3-phenyltetrahydropyran Oxalyl chloride (424 mg) was dissolved in dichloromethane (10 ml) and cooled to −78° C. before adding a solution of dimethylsulfoxide (221 mg in 2.5 ml dichloromethane) dropwise. After ½ hr, a solution of the product from Example 22 (1.19 g in 5 ml of dicloromethane) was added dropwise. After ½ hr, triethylamine (1.30 g) was added and the reaction allowed to warm to room temperature. The reaction mixture was washed with water (3×25 ml) and dried (brine) before passing through a Whatman 2 μm PTFE filter and concentrating the resulting organics under reduced pressure. The resulting crude oil was purified on silica eluting with 20% ethyl acetate in isohexane to afford the title compound (1.05 g) as a colourless oil.

$^1$H NMR (CDCl$_3$, 360 MHz): δ 1.47 (3H, d, J 6.6 Hz), 1.50–1.61 (1H, m), 1.95 (1H, br d, J 13.5 Hz), 2.11 (1H, ddd, J 17.5, 9.8, 2.1 Hz), 2.35 (1H, dd, J 17.5, 2.1 Hz), 2.66 (1H, dd, J 12.2, 3.1 Hz), 3.01–3.12 (1H, m), 3.72 (1H, dd, J 11.5, 4.0 Hz), 4.02–4.14 (1H, m), 4.47 (1H, d, J 3.1 Hz), 4.89 (1H, q, J 6.6 Hz), 7.21–7.31 (7H, m), 7.60 (1H, s), 9.64 (1H, s).

EXAMPLE 45

(2R,3R,4R,8R)-2-(1-(1-(3,5-bis(Trifluoromethyl) phenyl)ethyl)oxy)-4-formyl-3-phenyltetrahydropyran The title compound was prepared from the compound of Example 4 (isomer 4) by a procedure analogous to that described in Example 43.

$^1$H NMR (360 MHz, CDCl$_3$) δ 1.39 (3H, d, J 6.6 Hz), 1.81–1.87 (2H, m), 2.72–2.79 (1H, m), 3.00 (1H, dd, J 7.1, 10.4 Hz), 3.57–3.64 (1H, m), 4.13–4.19 (1H, m), 4.35 (1H, d, J 7.1 Hz), 4.96 (1H, q, J 6.6 Hz), 7.15–7.18 (2H, m), 7.24 (2H, s), 7.24–7.30 (3H, m), 7.68 (1H, s), 9.48 (1H, s).

EXAMPLE 46

(2R,3S,4R,8R)-2-(1-(1-(3,5-bis(Trifluoromethyl) phenyl)ethyl)oxy)-4-carboxymethyl-3-phenyltetrahydropyran The aldehyde of Example 44 (97 mg) was dissolved in a dichloromethane (2 ml)/water (2 ml) mixture and cooled to 0° C. before adding sulfamic acid (82 mg) and sodium chlorite (57 mg). The reaction was allowed to warm to room temperature before passing it through a Whatman 2 μm PTFE filter and concentrating the resulting organics under reduced pressure to afford the title compound.

$^1$H NMR (CDCl$_3$, 360 MHz): δ 1.46 (1H, d, J 6.6 Hz), 1.50–1.62 (1H, m), 1.92 (1H, dd, J 16.0, 10.4 Hz), 2.00 (1H, br d, J 17.1 Hz), 2.35 (1H, dd, J 16.0, 3.2 Hz), 2.65 (1H, dd, J 12.2, 3.3 Hz), 2.90–2.99 (1H, m), 3.74 (1H, dd, J 11.3, 3.6 Hz), 4.07 (1H, td, J 12.1, 2.5 Hz), 4.47 (1H, d, J 3.2 Hz), 4.88 (1H, q, J 6.6 Hz), 7.20 (2H, s), 7.21–7.34 (5H, m), 7.60 (1H, s).

EXAMPLE 47

(2R,3R,4R,8R)-2-(1-(1-(3,5-bis(Trifluoromethyl) phenyl)ethyl)oxy)-4-carboxy-3-phenyltetrahydropyran The title compound was prepared from the aldehyde of Example 45 by a procedure analogous to that described in Example 46.

$^1$H NMR (400 MHz, CDCl$_3$) δ 1.34 (3H, d J 6.6 Hz), 1.85–1.99 (2H, m), 2.76–2.87 (1H, m), 3.01 (1H, dd J 11.2 Hz 8.0 Hz), 3.57 (1H, tm J 10.4 Hz), 4.15 (1H dm J 11.9 Hz), 4.23 (1H, d J 8.1 Hz), 4.93 (1H, q J 6.6 Hz), 7.04–7.09 (2H, m), 7.16–7.23 (5H, m), 7.66 (1H, s).

EXAMPLE 48

(2R,3R,4R,8R)-2-(1-(1-(3,5-bis(Trifluoromethyl) phenyl)ethyl)oxy)-4-(4-methyl-4-carboxypiperidin-1-yl)methyl-3-phenyltetrahydropyran Step (i)—The compound of Example 31 (0.5 g) was dissolved in dimethylformamide (2 ml) under an atmosphere of nitrogen. The compound of Description 15 (0.44 g) and diisopropylethylamine (0.33 ml) were added and heated at 60° C. overnight. The dimethylformamide was removed in vacuo and the residue was dispersed between ethyl acetate (40 ml) and water (100 ml). The aqueous phase was extracted with ethyl acetate (3×40 ml). The combined organics were washed with brine and dried (MgSO$_4$). The solution was filtered, evaporated to dryness followed by chromatography on silica gel (eluting with isohexane containing increasing amounts of ethyl acetate 5–50%) to give a clear pale yellow oil (0.52 g). MS m/z (ES$^+$) 644 (M+H). $^1$H NMR (400 MHz, CDCl$_3$) δ 1.11 (3H, s), 1.28–1.45 (6H, m), 1.69–2.06 (8H, m), 2.22–2.49 (3H, m), 3.47–3.55 (1H, m), 4.12–4.19 (2H, m), 4.93 (1H, q J 6.6 Hz), 5.05 (2H, s), 6.96–7.04 (2H, m), 7.13–7.32 (10H, m), 7.65 (1H, s).

Step (ii)—The benzyl ester (Example 48 step (i); 0.5 g) was dissolved in methanol (40 ml), palladium on carbon 10% (80 mg) was added and shaken under hydrogen (50 psi) for 2 hr. The catalyst was removed by filtration and the methanol evaporated to give a white foam (0.38 g). The foam was dissolved in diethyl ether, etheral HCl (0.6 ml of 1.0M solution) was added and left to stand for 15 mins. The solvent was removed and the hydrochloride salt crystallised from a 9:1 mixture of ethyl acetate and isopropanol). $^1$H NMR (400 MHz, CDCl$_3$) δ 0.95 (3H, s), 1.06–1.47 (7H, m), 1.82–2.78 (10H, m), 3.41 (1H, t J 11.6 Hz), 3.92 (1H, dm J 11.6 Hz), 4.19 (1H, d J 8.2Hz), 4.93 (1H, q J 6.5 Hz), 6.95–7.05 (2H, m), 7.12–7.28 (5H, m), 7.67 (1H, s). MS m/z (ES$^+$) 574 (M+H).

EXAMPLE 49

(2R,3R,4R,8R)-2-(1-(1-(3,5,-bis(Trifluoromethyl) phenyl)ethyl)oxy)-4-(4-ethoxycarbonylpiperidin-1-yl)methyl-3-phenyltetrahydropyran A solution of the compound of Example 31; (0.93 g, 1.8 mmol) and ethyl 4-isonipecotate (1.08 g, 7.0 mmol) in dimethylformamide (1.5 ml) was heated at 60° C. for 16 h and 80° C. for 4 h. After cooling the solution was diluted by addition of ethyl acetate (100 ml) and water (10 ml). The organic phase was washed with water (5×50 ml) and saturated brine (50 ml) and dried (MgSO$_4$). The solution was filtered, evaporated to dryness and the residue purified by chromatography on silica gel (eluting with 1% methanol in dichloromethane) followed by chromatography on silica gel (eluting with isohexane containing increasing amounts of ethyl acetate (0–10%)) to give the title compound (1.0 g).

$^1$H NMR (360 MHz, CDCl$_3$) δ 1.21 (3H, t, J 7.1 Hz), 1.35 (3H, d J 8.8 Hz), 1.39 (1H, m), 1.5–1.8 (6H, m), 1.85–2.0 (4H, m), 2.1 (1H, m), 2.37 (1H, dd J 9.9 Hz and 8.5 Hz), 2.54 (1H, m), 2.55 (1H, m), 2.67 (1H, m), 3.50 (1H, td J 10.7 Hz and 1.9 Hz), 4.07 (2H, q J 7.1 Hz), 4.14 (1H, m), 4.17 (1H, d J 8.4 Hz), 4.9 (1H, q, J 6.5 Hz), 7.0 (2H, m), 7.16 (2H, s), 7.20 (3H, m), 7.65 (1H, s).

To a solution of the free base (0.73 g) in diethyl ether (5 ml) was added toluenesulphonic acid monohydrate (0.24 g). After cooling the solution at 0° C. for 0.5 h the crystals which had formed were removed by filtration to give the title compound tosylate salt 0.81 g mp 150–153° C.

EXAMPLE 50

(2R,3R,4R,8R)-2-(1-(1-(3,5,-bis(Trifluoromethyl) phenyl)ethyl)oxy)-4-(4-carboxypiperidin-1-yl) methyl-3-phenyltetrahydropyran A solution of the compound of Example 49, (0.63 g) was stirred in a mixture of a methanol:water (2:1; 13 ml) and lithium hydroxide (0.36 g). The solution was stirred at room temperature for 2 h and then reduced in volume in uacuo. The solution was neutralised by addition of carbon dioxide (pH 7.0) and cooling to +5° C. The solid which formed was removed by filtration and was washed with cold water and dried in vacuo to give the title compound.

$^1$H NMR (360 MHz, CDCl$_3$) δ 1.33 (3H, d J 6.6 Hz), 1.45 (1H, m), 1.57–1.85 (5H, m), 1.90–2.2 (5H, m), 2.19–2.44 (2H, m), 2.90 (1H, v broad d J 11.0 Hz), 2.98 (1H, m), 3.47 (1H, t J 11.2 Hz), 4.05 (1H, dd J 11.3 Hz and 3.6 Hz), 4.18 (1H, d J 8.2 Hz), 4.91 (1H, q J 6.5 Hz), 5.65 (1H, v broad s), 6.99 (2H, m), 7.15 (2H, s), 7.22 (3H, apparent t J 3.0 Hz), 7.66 (1H, s).

To a solution of the zwitterion above (0.22 g) dissolved in diethyl ether (10 ml) was added 1M ethereal HCl. The crystalline solid which formed was removed by filtration and was dried in vacuo mp 200–201° C. M/Z (ES$^+$) 560 (M+H).

EXAMPLE 51

(2R,3R,4R,8R,9(3'R))-2-(1-(1-(3,5-bis (Trifluoromethyl)phenyl)ethyl)oxy)-4-(ethoxycarbonyl-3-methylpiperidin-1-yl)methyl-3-phenyltetrahydropyran and

EXAMPLE 52

(2R,3R,4R,8R,9(3'S))-2-(1-(1-(3,5-bis (Trifluoromethyl)phenyl)ethyl)oxy)-4-(3-ethoxycarbonyl-3-methylpiperidin-1-yl)methyl-3-phenyltetrahydropyran A mixture of the compound of Example 31 (0.2 g) and ethyl 3-methylpiperidine-3-carboxylate (Description 15, 0.2 g) were heated at 90° C. for 16 h. The cooled residue was purified by chromatography on silica gel eluting with ethyl acetate in isohexane (5% to 10%) to give two separated diastereomers.

Example 51 (faster eluting) (2R,3R,4R,8R,9(3'R))-2-(1-(1-(3,5-bis(trifluoromethyl)phenyl)ethyl)oxy)-4-(3-ethoxycarbonyl-3-methylpiperidin-1-yl)methyl-3-phenyltetrahydropyran $^1$H NMR (360 MHz, CDCl$_3$) δ 1.06 (3H, s, CH3), 1.23 (3H, t, J 7.2 Hz), 1.35 (3H, d, J 6.6 Hz, CH3), 1.4–1.6 (5H, m), 1.62–1.79 (1H, m), 1.88–1.97 (5H, m), 2.33–2.38 (2H, m), 2.57–2.69 (1H, m), 3.49 (1H, brt), 4.08–4.14 (3H, m), 4.15 (1H, d, J 8.3 Hz), 4.93 (1H, q, J 6.5 Hz), 6.99–7.02 (2H, m), 7.15 (2H, s), 7.19–7.22 (3H, m), 7.65 (1H, s). MS (ES$^+$) m/z 602 (M+H, 100%).

Example 52 (slower eluting) (2R,3R,4R,8R,9(3'S))-2-(1-(1-(3,5-bis(trifluoromethyl)phenyl)ethyl)oxy)-4-(3-ethoxycarbonyl-3-methylpiperidin-1-yl)methyl-3-phenyltetrahydropyran $^1$H NMR (400 MHz, CDCl$_3$) δ 1.04 (3H, s), 1.27 (4H, m), 1.32 (3H, d J 6.6 Hz), 1.41–1.47 (2H, m), 1.61–1.68 (2H, m), 1.82–2.07 (6H, m), 2.35 (2H, dd J 10.3 Hz and 8.3 Hz), 2.95 (1H, d J 10.7 Hz), 3.54 (1H td J 10.7 Hz and 2.1 Hz), 3.99–4.20 (4H, m), 4.96 1(1H, q J 6.6 Hz), 7.02 (2H, m), 7.17 (2H, s), 7.22–7.26 (3H, m), 7.66 (1H, s). MS (ES$^+$) m/z 602 (M+H, 100%).

EXAMPLE 53

(2R,3R,4R,8R,9(3'R))-2-(1-(1-(3,5-bis (Trifluoromethyl)phenyl)ethyl)oxy)-4-(3-carboxy-3-methylpiperidin-1-yl)methyl-3-phenyltetrahydropyran The product of Example 51 (0.13 g) was heated in methanol (3 ml) and 4M-NaOH (0.5 ml, aqueous) at 60° C.

for 16 h. The solution was cooled to room temperature and the methanol removed by evaporation. The solution was adjusted to pH 7.0 by addition of solid $CO_2$ and then extracted with ethyl acetate (three times). The combined organic phases were dried ($Na_2SO_4$) and evaporated to dryness. The residue was purified by chromatography on silica gel (eluting with increasing concentrations of $CH_2Cl_2$/ MeOH/conc. aqueous $NH_3$ (100:10:0.4) in $CH_2Cl_2$ (0%–100%) to give the title compound as the free base.

$^1$H NMR (360 MHz, $CDCl_3$) δ 1.09 (3H, s), 1.35 (3H, d J 6.6 Hz), 1.45–1.75 (5H, m), 1.90 (2H, v broad d J 13.1 Hz), 2.0 (1H, d J 11.7 Hz), 2.1–2.25 (3H, m), 2.38 (1H, dd J 11.2 Hz and 9.2 Hz), 2.75 (1H, d J 11.8 Hz), 2.90 (1H, d J 9.2 Hz), 3.55 (1H, td J 12.1 Hz and 2.2 Hz), 4.16 (1H dd J 12.0 Hz and 3.1 Hz), 4.95 (1H q J 6.5 Hz), 7.00 (2H, m), 7.16 (2H, s), 7.25 (3H, m), 7.66 (1H, s).

To a solution of the free base (87 mg) in $CH_2Cl_2$ was added 1M-ethereal HCl (0.16 ml). The solution was evaporated to dryness and the product as the hydrochloride salt crystallised from diethyl ether:mp 166–167° C.

$^1$H NMR (400 MHz, MeOH) δ 1.19 (3H, s, CH3), 1.33 (3H, d, J 6.6 Hz, $CH_3$), 1.40 (1H, ddd, J 3.9, 3.9, 13.7 Hz), 1.60–1.71 (2H, m), 1.76–1.81 (1H, m), 2.01–2.12 (2H, m), 2.45–2.51 (2H, m), 2.56 (1H, ddd, J 3.0, 3.0, 12.7 Hz), 2.72 (1H, d, J 13.2 Hz), 2.77 (1H, d, 12.4 Hz), 3.01–3.07 (1H, m), 3.24–3.27 (1H, m), 3.50 (1H, d, J 12.4 Hz), 3.69 (1H, ddd, J 1.9, 1.9, 12.0 Hz), 4.17 (1H, dd, J 3.0, 12.0 Hz), 4.42 (1H, d, J 7.8 Hz), 5.04 (1H, q, J 6.5 Hz), 7.15–7.17 (2H, m), 7.24–7.32 (3H, m), 7.33 (2H, s), 7.74 (1H, s). MS (ES+) m/z 574 (MH+, 100%).

EXAMPLE 54

(2R,3R,4R,8R,9(3'S))-2-(1-(1-(3,5-bis (Trifluoromethyl)phenyl)ethyl)oxy)-4-(3-carboxy-3-methylpiperidin-1-yl)methyl-3-phenyltetrahydropyran The product of Example 52 (0.087 g) was deprotected and isolated by a procedure analogous to that described for diastereomer 1 (in Example 53 (ii) above).

$^1$H NMR (360 MHz, $CDCl_3$) δ 1.08 (3H, s), 1.35 (3H, d J 5.9 Hz), 1.54 (1H, ddd J 11.1 Hz and 3.6 Hz), 1.60 (2H, d J 11.7 Hz), 1.88 (2H, m), 2.0–2.2 (4H, m), 2.32 (2H, m), 2.87 (m), 3.56 (td J 11.0 Hz and 1.6 Hz), 4.12 (2H, m), 4.21 (1H, d J 7.5 Hz), J 4.94 (1H, q J 5.9 Hz), 7.01 (2H, m), 7.16 (2H s), 7.26 (3H, m), 7.66 (1H, s). MS (ES+) m/z 574 (MH+, 100%).

To a solution of the free base (74 mg) in $CH_2Cl_2$ was added 1M-ethereal HCl (0.16 ml). The solution was evaporated to dryness and the product as the hydrochloride salt crystallised from ethyl acetate mp 166° C.

EXAMPLE 55

(2R,3R,4R,8R)-2-(1-(1-(3,5-bis(Trifluoromethyl) phenyl)ethyl)oxy)-3-phenyl-4-(1,2,4-triazol-3-yl) methyltetrahydropyran a) (2R,3R,4R,8R)-2-(1-(1-(3,5-bis(Trifluoromethyl)phenyl) ethyl)oxy)-3-phenyl-4-(1-hydroxy-1-($N^2$-(trimethylsilyl) ethoxymethyl)-1,2,4-triazol-3-yl)methyltetrahydropyran n-Butyllithium (1.12 ml, 1.6M hexane) was added to a solution of $N^2$-(trimethylsilyl)ethoxymethyl-1,2,4-triazole (0.357 g) in tetrahydrofuran (4 ml) at −78° C. under a nitrogen atmosphere. The mixture was stirred at −78° C. for 10 minutes then warmed to −20° C. and stirred for 30 minutes. This mixture was re-cooled to −78° C. and a solution of the aldehyde of Example 45 in tetrahydrofuran (6 ml) was added dropwise. The mixture was quenched with water, then allowed to warm to room temperature. The solution was extracted with ethyl acetate and the pooled organic extracts washed with brine, dried (magnesium sulfate), and concentrated to leave an orange oil. This was purified on silica using 30% ethyl acetate in hexane as eluant, to afford the title compound as a mixture of carbinol epimers. MS (ES+) m/z 646 (M++H), 388 (M+ −257).

b) (2R,3R,4R,8R)-2-(1-(1-(3,5-bis(Trifluoromethyl)phenyl) ethyl)oxy)-3-phenyl-4-($N^2$-(trimethylsilyl)ethoxymethyl-1, 2,4-triazol-3-yl)methyltetrahydropyran The carbinol described in (a) above, (0.497 g, mixture of epimers) was dissolved in 1,2-dichloroethane (3 ml) and thiocarbonyldiimidazole (0.260 g) was added. The mixture was heated to reflux and stirred under an atmosphere of nitrogen for 5 hours. The mixture was cooled to room temperature and extracted into dichloromethane. The pooled organic extracts were washed with brine, dried (magnesium sulfate) and concentrated in vacuo to afford a yellow oil. This was purified on silica, using 40% ethyl acetate in hexane to elute epimer A and 80% ethyl acetate in hexane to elute epimer B.

A mixture of both epimers (0.341 g) and azobisisobutyronitrile (38 mg) was dissolved in toluene and added to a refluxing solution of tributyltin hydride (0.298 ml) in toluene (3 ml) via a syringe pump over 1.5 hours. The mixture was refluxed for a further 3 h under an atmosphere of nitrogen after which time further azobis isobutyronitrile (38 mg) was added. After 2 h the mixture was cooled to room temperature and extracted with ethyl acetate. The pooled organic extracts were washed with brine, dried (magnesium sulfate), and concentrated in vacuo to afford a yellow oil. This was purified on silica, using 25% ethyl acetate in hexane, gradually increasing to 100% ethyl acetate as eluant, to afford the title compound as a yellow oil.

c) (2R,3R,4R,8R)-2-(1-(1-(3,5-bis(Trifluoromethyl)phenyl) ethyl)oxy)-3-phenyl-4-(1,2,4-triazol-3-yl) methyltetrahydropyran The Sem-protected triazole described in (b) above (0.1 g) was dissolved in tetrahydrofuran and tetrabutylammonium fluoride (0.8 ml, 1M THF) was added. The mixture was heated to 40° C. and stirred under an atmosphere of nitrogen for 15 hours. The mixture was cooled to room temperature and extracted with ethyl acetate. The pooled organic extracts were washed with brine, dried (magnesium sulfate), and concentrated in vacuo to afford a pale yellow oil. This was purified using medium pressure chromatography, using 4% methanol in dichloromethane as eluant, to afford the title compound as a white foam. $^1$H NMR (360 MHz, $CDCl_3$) δ 1.09 (1H, d, J 11.8 Hz), 1.19–1.32 (1H, m), 1.37 (3H, d, J 6.6 Hz), 1.69–1.82 (1H, m), 2.41–2.48 (1H, m), 2.93 (1H, dd, J 11.8, 8.4 Hz), 3.51 (1H, td, J 12.6, 2.3 Hz), 4.07 (1H, dd, J 11.7, 3.2 Hz), 4.31 (1H, d, J 8.4 Hz), 4.59 (1H, d, J 2.2 Hz), 4.95 (1H, q, J 6.5 Hz), 7.13–7.32 (7H, m), 7.67 (1H, s), 7.93 (1H, s); MS (ES+) m/z 242 (M+ −257).

EXAMPLE 58

(2R,3S,4S,8R)-2-(1-(1-(3,5-bis(Trifluoromethyl) phenyl)ethyl)oxy)-3-phenyl-4-(1,2,4-triazol-3-yl) methyltetrahydropyran This compound was prepared from the aldehyde of Example 43 following the procedure described in Example 55.

$^1$H NMR (360 MHz, $CDCl_3$) δ 1.44 (3H, d, J 6.6 Hz), 1.62 (1H, dddd, J 5.0, 12.8, 12.8, 12.8 Hz), 1.79–1.83 (1H, m), 2.40 (1H, dd, J 9.5, 14.8 Hz), 2.66 (1H, dd, J 3.2, 12.0 Hz), 2.77 (1H, dd, 3.5, 14.8 Hz), 2.96–3.05 (1H, m), 3.96–3.73 (1H, m), 4.01 (1H, ddd, 2.4, 13.4, 13.4 Hz), 4.47 (1H, d, J 3.1 Hz), 4.87 (1H, q, J 6.6 Hz), 7.20 (2H, s), 7.26–7.33 (5H, m), 7.60 (1H, s), 7.99 (1H, s).

EXAMPLE 128

(2R,3R,4R,8R)-2-(1-(1-(3,5-bis(Trifluoromethyl) phenyl)ethyl)oxy)-3-phenyl-4-(5-methoxycarbonyl-1,2,3-triazol-1-yl)ethyltetrahydropyran a) (2R,3R,4R,8R)-4-Azidoethyl-2-(1-(1-(3,5-bis (trifluoromethyl)phenyl)ethyl)oxy)-4-(5-methoxycarbonyl-1,2,3-triazol-1-yl)ethyl-3-phenyltetrahydropyran The mesylate of Example 38 (0.397 g) was dissolved in dimethylformamide (1.5 ml) and sodium azide (0.072 g) was added. The mixture was heated to 60° C. and stirred under an atmosphere of nitrogen for 4 hours. Further sodium azide (0.024 g) was added to the mixture and the mixture was stirred for 5 hours. The mixture was cooled to room temperature and extracted with ethyl acetate. The pooled organic extracts were washed with water, brine, dried (magnesium sulfate) and concentrated in vacuo to afford a colourless oil. This was purified on silica using 7% ethyl acetate in hexane as eluant, to afford the azide as a colourless oil.

$^1$H NMR (360 MHz, CDCl$_3$) δ 1.16–1.29 (1H, m), 1.35 (3H, d, J 6.6 Hz), 1.40–1.54 (2H, m), 1.75 (1H, d, J 13.3 Hz), 1.85–1.94 (1H, m), 2.40 (1H, dd, J 11.4, 8.4 Hz), 3.02–3.17 (2H, m), 3.54 (1H, td, J 12.1, 2.1 Hz), 4.09–4.16 (1H, m), 4.20 (1H, d, J 8.4 Hz), 4.94 (1H, q, J 6.6 Hz), 7.01–7.04 (2H, m), 7.17 (2H, s), 7.23–7.26 (3H, m), 7.66 (1H, s).

b) (2R,3R,4R,8R)-2-(1-(1-(3,5-bis(Trifluoromethyl)phenyl) ethyl)oxy)-4-(5-methoxycarbonyl-1,2,3-triazol-1-yl)ethyl-3-phenyltetrahydropyran The azide described in (a) above (0.233 g) was dissolved in toluene (1 ml) and methyl propiolate (0.047 ml) was added. The mixture was heated to 80° C. and stirred under an atmosphere of nitrogen for 24 hours. Further methyl propiolate (0.047 ml) was added and the mixture stirred for 5 hours. The mixture was cooled to ambient temperature and concentrated in vacuo to afford a yellow oil. This mixture of regioisomers was purified on silica using 25% ethyl acetate in hexane, gradually increasing to 40% ethyl acetate in hexane as eluant, to afford the title compound (the faster eluting compound) as a colourless oil.

$^1$H NMR (400 MHz, CDCl$_3$) δ 1.33 (3H, d, J 6.5 Hz), 1.48–1.57 (2H, m), 1.60–1.69 (1H, m), 1.74–1.82 (1H, m), 1.90 (1H, d, Br), 2.40 (1H, t, J 10.8 Hz), 3.51 (1H, t, J 11.9 Hz), 3.76 (3H, s), 4.11–4.15 (2H, m), 4.47–4.55 (1H, m), 4.58–4.65 (1H, m), 4.91 (1H, q, J 6.5 Hz), 6.83 (2H, d, J 6.2 Hz), 7.13 (2H, s), 7.16–7.17 (2H, m), 7.64 (1H, s), 8.02 (1H, s); MS (ES$^+$) m/z 572 (MH$^{+)}$, 314 (M$^+$ −257).

EXAMPLE 129

(2R,3R,4R,8R)-2-(1-(1-(3,5-bis(Trifluoromethyl) phenyl)ethyl)oxy)-4-(4-methoxycarbonyl-1,2,3-triazol-1-yl)ethyl-3-phenyltetrahydropyran This compound was obtained as the slower eluting regioisomer from the experiment described in Example 128 (b).

$^1$H NMR (400 MHz, CDCl$_3$) δ 1.34 (3H, d, J 6.5 Hz), 1.44–1.57 (1H, m), 1.60–1.72 (2H, m), 1.75–1.84 (2H, m), 2.43 (1H, t, J 9.8 Hz), 3.50 (1H, t, J 11.4 Hz), 3.93 (3H, s), 4.11–4.29 (4H, m), 4.92 (1H, q, J 6.5 Hz), 6.89 (2H, d, J 6.7 Hz), 7.14 (2H, s), 7.22–7.23 (3H, m), 7.65 (1H, s), 7.71 (1H, s); MS (ES$^+$) m/z 572 (MH$^+$), 314 (M$^+$ −257).

The Examples shown below in Tables 3 and 4 were prepared by reacting the mesylate (Examples 3, 6, 21, 23, 31 or 38) or iodide (Examples 19, 40, 41 or 42) with the appropriate amine. For the Examples in Tables 3 and 4 which contain carboxylic acids, the amines were added as amino esters and the resulting esters were subsequently deprotected by standard methodology, as in Example 48 (ii) or Example 53.

TABLE 3

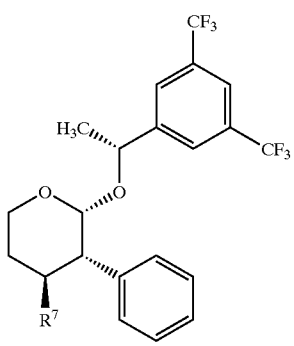

| Ex. No. | From mesylate | R$^7$ | MS (ES$^+$) (M + H) | $^1$H NMR | Stereochemistry |
|---|---|---|---|---|---|
| 56 | 6 | ![pyrazole-CH2—] | 500 | (360 MHz, CDCl$_3$) δ 1.45(3H, d, J 6.6Hz), 1.56–1.64(2H, m), 2.67(1H, dd, J 3.1, 12.2Hz), 3.07–3.13(1H, m), 3.70–3.75(1H, m), 3.93–3.98(1H, m), 3.98(1H, dd, J 8.7, 13.6Hz), 4.31(1H, dd, J 3.6, 13.9Hz), 4.47(1H, d, J 3.1Hz), 4.87(1H, q, J 6.6Hz), 7.19(2H, s), 7.26–7.38(6H, m), 7.61 (1H,s), 7.66(1H, s). | 2R,3S, 4S,8R |

TABLE 3-continued

[Structure: tetrahydropyran with (1-(3,5-bis(trifluoromethyl)phenyl)ethoxy) at position 2, phenyl at position 3, and R⁷ at position 4]

| Ex. No. | From mesylate | R⁷ | MS (ES⁺) (M + H) | ¹H NMR | Stereo-chemistry |
|---|---|---|---|---|---|
| 57 | 6 | 2H-1,2,3-triazol-2-yl-CH₂— | 500 | (360 MHz, CDCl₃) δ 1.44(3H, d, J 6.6Hz), 1.45–1.50(1H, m),1.58(1H, dddd, J 5.0, 12.4, 12.4, 12.4Hz), 2.77(1H, dd, J 3.2, 12.2Hz), 3.16–3.22(1H, m), 3.67–3.72(1H, m), 3.96 (1H, dt, J 2.6, 12.7Hz), 4.02(1H, dd, J 9.8, 13.5Hz), 4.35 (1H, dd, J 3.9, 13.5Hz), 4.48(1H, d, J 3.2Hz), 4.86(1H, q, J 6.6Hz), 7.20(2H, s), 7.28–7.35(5H, m), 7.58(2H, s), 7.61 (1H, s). | 2R,3S, 4S,8R |
| 59 | 23 | 1H-tetrazol-1-yl-CH₂—CH₂— | 515 | (360 MHz, CDCl₃) δ 1.44(3H, d, J 6.6Hz), 1.50–1.64(2H, m), 1.83–1.95(2H, m), 2.37–2.46(1H, m), 2.62(1H, dd, J 11.2, 3.2Hz), 3.77(1H, dd, J 11.4, 3.9Hz), 3.98–4.09(1H, m), 4.24–4.40(2H, m), 4.40(1H, d, J 3.2Hz), 4.86(1H, q, J 6.6Hz), 7.11–7.13(2H, m), 7.19(2H, s), 7.26–7.31(3H, m), 7.59(1H, s). | 2R,3S, 4S,8R |
| 60 | 23 | 1H-1,2,3-triazol-1-yl-CH₂—CH₂— | 514 | (360 MHz, CDCl₃) δ 1.43(1H, d, J 6.6Hz), 1.45–1.62(2H, m), 1.90–1.93(1H, m), 1.94–2.02(1H, m), 2.35–2.48(1H, m), 2.58–2.63(1H, m), 3.71–3.78 m (1H, m), 3.94–4.06 (1H, m), 4.23–4.41(2H, m), 4.43(1H, d, J 3.0Hz), 4.82–4.85(1H, m), 7.09–7.11(2H, m), 7.18(2H, s), 7.26–7.29 (3H, m), 7.36(1H, s), 7.59(1H, s), 7.69(1H, s). | 2R,3S, 4S,8R |
| 61 | 23 | 1H-pyrazol-1-yl-CH₂—CH₂— | 514 | (360 MHz, CDCl₃) δ 1.43(3H, d, J 6.7Hz), 1.46–1.62(2H, m), 1.90(1H, br d, J 13.2Hz), 1.93–2.03(1H, m), 2.48–2.52 (1H, m), 2.62(1H, dd, J 11.9. 3.1Hz), 3.73(1H, dd, J 11.2, 4.7Hz), 3.94–4.03(1H, m), 4.37–4.43(3H, m), 4.84(1H, q, J 6.6Hz), 7.04–7.12(2H, m), 7.18(2H, s), 7.20–7.27(3H, m), 7.57–7.61(3H, m). | 2R,3S, 4S,8R |
| 62 | 23 | —CH₂—CH₂—NMe₂ | 516 | (360 MHz, CDCl₃) δ 1.35(3H, d, J 6.6Hz), 1.46–1.67(3H, m), 1.85–1.91(3H, m), 2.08–2.20(3H, m), 2.27–2.32(1H, m), 2.40(1H, dd, J 11.4, 8.3Hz), 2.47–2.53(1H, m), 2.69–2.75(2H, m), 3.30–3.40(1H, m), 3.64(2H, t, Br), 4.12(1H, dd, J 11.8, 3.1Hz), 4.27(1H, d, J 8.3Hz), 4.93(1H, q, J 6.6Hz), 7.07–7.10(2H, m), 7.15(2H, s), 7.25–7.28 (3H, m), 7.65(1H, s) | 2R,3S, 4S,8R |
| 63 HCl salt | 23 | —H₂C—H₂C—N(3-carboxypiperidin-1-yl) | 574 | (360 MHz, MeOD) δ 1.25–2.21(11H, m), 2.53–3.21(8H, m), 3.48–3.52(1H, m), 3.76(1H, dd J 11.2Hz 4.5Hz), 4.44 (1H, 2.5Hz), 4.95(1H, q J 6.0Hz), 7.22–7.49(7H, m), 7.68(1H, s). | 2R,3S, 4S,8R, 3'R/S |
| 64 Free base | 23 | —H₂C—H₂C—N(2-carboxypiperidin-1-yl) | 574 | (400 MHz, CDCl₃) δ 1.24–1.88(14H, m), 2.03–2.14(1H, m), 2.38–3.11(1H, m), 2.61(1H, dd J 11.8Hz 2.6Hz), 3.99 (1H, tm J 11.3Hz), 4.41(1H, d J 2.7Hz), 4.86(1H, q J 6.4Hz), 7.13–7.38(7H, m), 7.70(1H, s) | 2R,3S, 4S,8R, 2'R |
| 65 | 23 | CH₂—CH₂—(2-(hydroxymethyl)pyrrolidin-1-yl) | 546 | (360 MHz, CDCl₃) δ 1.04–1.17(1H, m), 1.41–2.21(12H, m), 2.35–2.53(2H, m), 2.61(1H, dd J 12.0Hz 3.2Hz), 2.71–3.04(3H, m), 3.34(1H, dd J 10.8Hz 3.7Hz), 3.53(1H, dd J 10.8Hz 3.7Hz), 3.73(1H, dm J 10.0Hz), 4.01(1H, tm, J 13.2Hz), 4.44(1H, d J 3.1Hz), 4.87(1H, q J 6.6Hz), 7.16–7.33(7H, m), 7.60(1H, s). | 2R,3S, 4S,8R, 2'R |

TABLE 3-continued

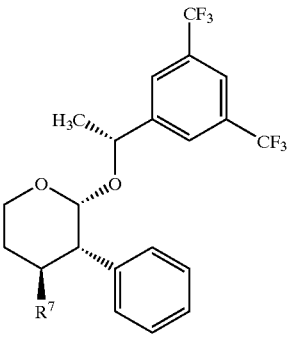

| Ex. No. | From mesylate | R⁷ | MS (ES⁺) (M + H) | ¹H NMR | Stereo-chemistry |
|---|---|---|---|---|---|
| 66 HCl salt | 23 | —H₂C—H₂C—N(piperidine)—COOEt | 602 | (DMSO-d₆, 360 MHz) δ 1.17(3H, t, J 7.1Hz), 1.21–1.32 (2H, m), 1.40(3H, d, J 6.5Hz), 1.44–1.52(1H, m), 1.60–1.17(1H, m), 1.85–1.90(1H, m), 1.91–2.03(2H, m), 2.35–2.47(1H, m), 2.52–2.60(1H, m), 2.64–2.70(1H, m), 2.70–2.81(1H, m), 2.82–2.90(1H, m), 2.99–3.10(2H, m), 3.35–3.41(3H, m), 3.68–3.73(1H, m), 3.90–3.97(1H, m), 4.06 (2H, q, J 7.1Hz), 4.40–4.42(1H, m), 4.94(1H, m), 7.26–7.30(5H, m), 7.45(2H, s), 7.83(1H, s), 9.10–9.30(1H, m). | 2R,3S, 4S,8R |
| 67 Free base | 23 | —H₂C—H₂C—N(piperidine)—COOH | 575 | (CDCl₃, 400 MHz) δ 1.27–1.34(1H, m), 1.42(3H, d, J 6.6 Hz), 1.51(1H, qd, J 13.2, 5.1Hz), 1.58–1.68(1H, m), 1.69–1.82(2H, m), 1.83–2.00(3H, m), 2.01–2.22(3H, m), 2.42–2.49(1H, m), 2.54–2.67(2H, m), 2.72–2.82(1H, m), 3.70 (1H, dd, J 11.0, 4.0Hz), 3.96(1H, br t, J 11.0Hz), 4.41(1H, d, J 3.0Hz), 4.84(1H, q, J 6.5Hz), 7.13–7.21(5H, m), 7.23–7.28(2H, m), 7.59(1H, s). | 2R,3S, 4S,8R |
| 68 HCl salt | 23 | triazole-CH₂—CH₂—, with CH₂—NMe₂ | 571 | (DMSO-d₆, 360 MHz) δ 1.40(3H, d, J 6.6Hz), 1.43–1.54 (2H, m), 1.58–1.64(1H, m), 1.99–2.02(1H, m), 2.43–2.52 (1H, m), 2.70(1H, dd, J 12.0, 3.0Hz), 2.80(6H, s), 3.74(1H, dd, J 11.2, 4.1Hz), 3.96(1H, br t, J 11.4Hz), 4.12–4.30(2H, m), 4.41–4.50(3H, m), 4.96(1H q, J 6.5Hz), 7.10–7.27(5H, m), 7.44(2H, s), 7.82(1H, s), 8.06(1H, s), 10.70(1H, s). | 2R,3S, 4S,8R |
| 69 HCl salt | 23 | CH₂—CH₂— N(pyrrolidine)—COOH | 560 | (360 MHz, DMSO) δ 1.17–1.29(1H, m), 1.41(3H, d, J 6.6Hz), 1.46–1.59(1H, m), 1.76–2.02(4H, m), 2.30–2.39(2H, m), 2.67(1H, dd, J 11.7, 2.3Hz), 2.89–2.98(1H, m), 3.02–3.12(1H, m), 3.20–3.46(3H, m), 3.72(1H, dd, 10.2, 4.0Hz), 3.95(1H, tm, J 11.1Hz), 4.09–4.16(1H, m), 4.41(1H, d, J 3.1Hz), 4.96(1H, q, J 6.1Hz), 7.20–7.31 (5H, m), 7.46(1H, s), 7.83(1H, s) | 2R,3S, 4S,8R, 2'R |
| 70 | 23 | CH₂—CH₂— N(pyrrolidine)—COOMe | 574 | (400 MHz, CDCl3) δ 0.98–1.08(1H, m), 1.41–1.54(5H, m), 1.69–1.80(1H, m), 1.81–2.0(3H, m), 2.01–2.12(2H, m), 2.26–2.34(1H, m), 2.49–2.61(2H, m), 2.67(1H, qm, J 8.12, 3.5Hz), 2.98–3.04(2H, m), 3.63(3H, s), 3.73(1H, dd, J 10.6, 4.2Hz), 4.04(1H, dt, J 13.1, 2.2Hz), 4.42–4.45(1H, m), 4.86(1H, q, J 6.8Hz), 7.18–7.29(7H, m), 7.59(1H, s) | 2R,3S, 4S,8R, 2'R |
| 146 | 23 | CH₂—CH₂— N(pyrrolidine)—OH | 546 | (360 MHz, DMSO) δ 1.15–1.29(1H, m), 1.38–1.50(5H, m), 1.53–1.80(3H, m), 1.82–1.95(2H, m), 1.95–2.06(1H, m), 2.67(1H, dd, J 11.9, 3.1Hz), 2.80–2.90(1H, m), 2.97–3.09(1H, m), 3.25–3.41(2H, m), 3.52–3.60(1H, m), 3.72 (2H, dt, J 11.3, 4.1Hz), 3.95(1H, tm, J 10.7Hz), 4.41(1H, d, J 3.1Hz), 4.96(1H, q, J 6.4Hz), 5.39–5.45(1H, m), 7.20–7.32(5H, m), 7.46(2H, s), 7.83(1H, s) | 2R,3S, 4S,8R, 2'R |
| 71 | 23 | —H₂C—H₂C—N(piperidine)(Me)—COOH | 588 | (400 MHz, CDCl₃) δ 1.08(3H, s), 1.21–1.33(1H, m), 1.43 (3H, d, J 6.6Hz), 1.44–1.57(3H, m), 1.58–1.69(1H, m), 1.86(1H, d, J 13.3Hz), 2.03–2.13(2H, m), 2.38–2.50(1H, m), 2.54–2.68(4H, m), 2.72–3.01(3H, m), 3.71(1H, dd, J 10.64, 4.4Hz), 3.98(1H, t, J 10,92Hz), 4.41(1H, d, J 2.9Hz), 4.84(1H, q, J 6.4Hz), 7.18(4H, s, br), 7.21–7.27 (3H, m), 7.59(1H, s) | 2R,3S, 4S,8R |

TABLE 3-continued

[Structure: tetrahydropyran with (1R)-1-(3,5-bis(trifluoromethyl)phenyl)ethoxy group at position 2, phenyl at position 3, and R⁷ at position 4]

| Ex. No. | From mesylate | R⁷ | MS (ES⁺) (M + H) | ¹H NMR | Stereo-chemistry |
|---|---|---|---|---|---|
| 72 Free base | 23 | —H₂C—H₂C—N(piperidine with 4-Me and 4-CH₂OH) | 574 | (360 MHz, CDCl₃) δ 0.90(3H, s), 1.02–1.23(1H, m), 1.28 (2H, dm, J 13.6Hz), 1.42–1.61(7H, m), 1.83–2.52(9H, m), 2.60(1H, dd J 12.0Hz 3.2Hz), 3.33(2H, s), 3.72(1H, dd J 10.1Hz 3.7Hz), 4.02(1H, td J 13.2Hz J 2.3Hz), 4.42(1H, d J 3.1Hz), 4.85(1H, q J 6.6Hz), 7.17–7.29(7H, m), 7.59(1H, s). | 2R,3S, 4S,8R |
| 73 HCl salt | 23 | —H₂C—H₂C—N(piperidine with 4-CH₂OH) | 560 | (400 MHz, MeOD) δ 1.32–1.75(9H, m), 1.83–1.97(3H, m), 2.51–2.63(1H, m), 2.68–2.95(3H, m), 2.99(1H, td J 12.4Hz 4.8Hz), 3.10(1H, td J 12.4Hz 4.8Hz), 3.33–3.45(4H, m), 3.76(dd J 11.4Hz 3.9Hz), 4.45(1H, d J 3.1Hz), 4.96(1H, q J 6.5Hz), 7.23–7.39(7H, m), 7.69(1H, s). | 2R,3S, 4S,8R |
| 74 | 23 | CH₂—CH₂— N(pyrrolidine-2-COOH) | 560 | (360 MHz, CDCl₃) δ 1.03–1.18(1H, m), 1.40–1.61(5H, m), 1.64–1.92(4H, m), 1.96–2.12(1H, m), 2.15–2.48(3H, m), 2.29(1H, dd J 11.9Hz 3.1Hz), 2.68(1H, td J 11.3Hz 5.3Hz), 2.91–3.09(2H, m), 3.63(3H, s), 3.72(1H, dd J 11.2Hz 3.8H), 4.00(1H, td J 13.2Hz 2.3 Hz), 4.42(1H, d J 3.1Hz), 4.86(1H, q J 6.6Hz), 7.15–7.31(7H, m), 7.59(1H, s). | 2R,3S, 4S,8R, 2'S |
| 75 | 40 | isoxazole-3-CH₂-N(Me)-CH₂—CH₂— | 557 | | 2R,3S, 4S,8R |
| 76 | 40 | —H₂C—H₂C—N(piperidine-4-OH) | 546 | | 2R,3S, 4S,8R |
| 77 | 40 | —H₂C—H₂C—N(piperidine-4-(4-Me-1,2,4-triazol-3-yl)) | 611 | | 2R,3S, 4S,8R |
| 78 | 23 | —H₂C—H₂C—N(piperidine-3-COOH) | 574 | (400 MHz, CDCl₃) δ 1.45–2.36(14H, m), 2.42–2.65(4H, m), 2.66–3.04(2H, m), 3.74(1H, dm, J 11.1, 4.4Hz), 3.99–4.08(1H, m), 4.41–4.46(1H, m), 4.86(1H, q, J 7.0Hz), 7.19–7.32(7H, m), 7.70(1H, s). | 2R,3S, 4S,8R, 3'R |
| 79 HCl salt | 23 | —H₂C—H₂C—N(piperidine-2-COOH) | 574 | (360 MHz, CDCl₃) δ 1.21 1.89(12H, m), 2.03–2.86(5H, m), 3.12–3.38(3H, m), 3.71(1H, bd J 7.7Hz), 3.99(1H, tm J 11.5Hz), 4.43(1H, s), 4.85(1H, d J 6.0Hz), 7.1–7.42(7H, m), 7.6(1H, s). | 2R,3S, 4S,8R, 2'S |
| 80 | 40 | —H₂C—H₂C—N(5,6,7,8-tetrahydroimidazo[1,5-a]pyrazine) | 568 | | 2R,3S, 4S,8R |

TABLE 3-continued

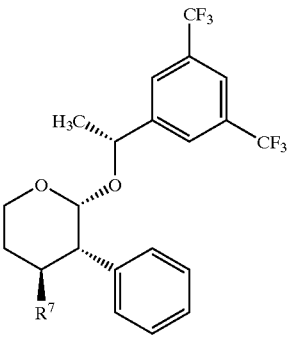

| Ex. No. | From mesylate | R⁷ | MS (ES⁺) (M + H) | ¹H NMR | Stereo-chemistry |
|---|---|---|---|---|---|
| 81 | 40 | —H₂C—H₂C—N(morpholine) | 532 | | 2R,3S, 4S,8R |
| 82 | 40 | —H₂C—H₂C—N(N-Me piperazine) | 545 | | 2R,3S, 4S,8R |
| 83 | 6 | —H₂C—N(2-oxa-8-azaspiro[4.5]decan-1-one) | 586 | (400 MHz, CDCl₃) δ 1.38–1.61(3H, m), 1.45(3H, d, J 6.6Hz), 1.80–2.01(4H, m), 2.09–2.19(5H, m), 2.53–2.68 (3H, m), 2.90–2.98(1H, m), 3.76(1H, dd, J 11.3, 3.8Hz), 4.01(1H, td, J 12.2, 2.1Hz), 4.24(2H, t, J 7.1Hz), 4.42(1H, d, J 2.9Hz), 4.87(1H, q, J 6.5Hz), 7.19(3H, s, br), 7.23–7.29(4H, m), 7.59(1H, s) | 2R,3S, 4S,8R |
| 84 HCl salt | 6 | —H₂C—N(3-Me-3-COOH piperidine) | 574 | (400 MHz, MeOH) δ 1.33(3H, s), 146–1.55(4H, m), 1.64–1.88(3H, m), 2.16–2.29(2H, m), 2.60–2.66(1H, m), 2.72–2.85(4H, m), 3.12–3.24(2H, m), 3.80–3.85(1H, m), 3.99 (1H, d, 12.4Hz), 4.17(1H, dt, J 13.4, 2Hz), 4.46–4.48(1H, m), 4.98(1H, q, 6.5Hz), 7.26–7.39(7H, m), 7.69(1H, s). | 2R,3S, 4S,8R 9(3'S/R) |
| 85 HCl salt | 6 | —H₂C—N(4-Me-4-COOH piperidine) | 574 | (400 MHz, MeOH) δ 1.20–1.30(3H, m), 1.49(3H, d, 6.6Hz), 1.57–1.81(4H, m), 1.96–2.39(6H, m), 2.44–2.55 (1H, m), 2.73(1H, dd, J 11.8, 3.2Hz), 2.88(1H, t, J 10.9Hz), 2.98–3.09(1H, m), 3.71–3.83(1H, m), 4.10–4.18 (1H, m), 4.46–4.52(1H, m), 4.98(1H, q, 6.6Hz), 7.25–7.39 (7H, m), 7.69(1H, s). | 2R,3S, 4S,8R |
| 86 HCl salt | 6 | —H₂C—N(2-COOH piperidine) | 560 | (400 MHz, MeOH) δ 1.47(3H, d, J 6.6Hz), 1.65–1.91(5H, m), 2.12–2.26(2H, m), 2.70–3.28(8H, m), 3.56–3.61(1H, m), 3.79–3.85(1H, m), 3.86–3.95(1H, m), 4.13(1H, dt, J 13.4, 2.04Hz), 4.45–4.49(1H, m), 4.97(1H, q, J 5.9Hz), 7.24–7.40(7H, m), 7.69(1H, s). | 2R,3S, 4S,8R, 9(2'R/S) |
| 87 HCl salt | 6 | —H₂C—N(2-COOH piperidine) | 560 | (400 MHz, MeOH), δ 1.49(3H, d, J 6.6Hz), 1.60–1.75(2H, m), 1.76–1.94(4H, m), 2.22(1H, bd, 13.4Hz), 2.40(1H, bd, 12.6Hz), 2.66–2.78(3H, m), 2.95–3.08(2H, m), 3.79–3.95(3H, m), 4.13(1H, td, J 13.1, 1.9Hz), 4.47(1H, d, 3.1Hz), 4.99(1H, q, J 6.6Hz), 7.25–7.40(7H, m), 7.69(1H, s). | 2R,3S, 4S,8R, 9(2'S/R) |
| 88 HCl salt | 6 | —H₂C—N(4-OH piperidine) | 532 | (360 MHz, CDCl₃) δ 1.39–1.70(6H, m), 1.76–1.99(4H, m), 2.02–2.21(3H, m), 2.45–2.70(3H, m), 2.78–2.89(1H, m), 3.56–3.67(1H, m), 3.75(1H, dm, J 10.0, 3.7, 1.2Hz), 4.01 (1H, dt, J 13.2, 2.2Hz), 4.42(1H, d, J 2.8Hz), 4.87(1H, q, J 6.6Hz), 7.13–7.32(7H, m), 7.59(1H, s). | 2R,3S, 4S,8R |
| 89 | 6 | —H₂C—N(4-CH₂OH piperidine) | 546 | (360 MHz, CDCl₃) δ 1.36–1.80(10H, m), 1.87–2.01(2H, m), 2.01–2.21(2H, m), 2.56(1H, dd, J 11.8, 3.0Hz), 2.60–2.73(2H, m), 2.95–3.08(1H, m), 3.47(2H, d, J 6.1Hz), 3.75 (1H, dd, J 10.9, 4.8Hz), 4.01(1H, t, 11.1Hz), 4.42(1H, d, 2.9Hz), 4.87(1H, q, J 6.5Hz), 7.15–7.31(7H, m), 7,59(1H, s). | 2R,3S, 4S,8R |

TABLE 4

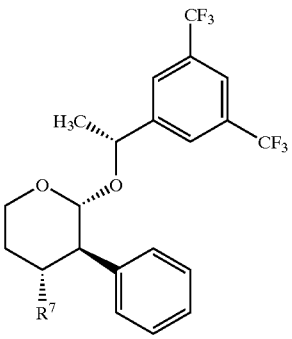

| Ex. No. | From mesylate | MS (ES+) M + H | R7 | 1H NMR | Stereochemistry |
|---|---|---|---|---|---|
| 90 Free base | 31 | 501 | tetrazol-2-yl-CH2— | (360MHz, CDCl3) δ 1.36(3H, d 6.6Hz), 1.52–1.68(2H, m), 2.39–2.53(2H, m), 3.52(1H, dt 11.9, 4.0Hz), 4.06–4.27(4H, m), 4.94(1H, q J 6.6Hz), 7.07–7.18(4H, m), 7.28–7.36(3H, m), 7.67(1H, s), 8.25(1H, s). | 2R, 3R, 4R, 8R |
| 91 Free base | 31 | 501 | tetrazol-1-yl-CH2— | (360MHz, CDCl3) δ 1.37(3H, d J 6.6Hz), 1.40–1.59(2H, m), 2.51–2.67(2H, m), 3.50(1H, dt, J 12.0, 2.5Hz), 4.09(1H, ddd, J 14.7, 1.9, 1.9Hz), 4.26(1H, d, J 7.7Hz), 4.31–4.42(2H, m), 4.94(1H, q, J 6.6Hz), 7.11–7.20(4H, m), 7.28–7.34(3H, m), 7.67(1H, s), 8.43(1H, s). | 2R, 3R, 4R, 8R |
| 92 Free base | 31 | 476 | —CH2—NMe2 | (400MHz, CDCl3) δ 1.26(1H, s), 1.35(3H, d J 6.6Hz) 1.40–1.49(1H, m) 1.23–1.30(1H, m), 1.41–1.98(2H, m), 2.03(6H, s) 2.34–2.40(1H, m), 3.49–3.58(1H, m), 4.11–4.16(1H, m) 4.18(1H, d J 8.4Hz) 4.94(1H, q J 6.4Hz), 6.98–7.04(2H, m), 7.16(2H, s), 7.23(3H, s) 7.65(1H, s). | 2R, 3R, 4R, 8R |
| 93 HCl salt | 31 | 518 | —H2C—morpholinyl | (400MHz, CDCl3) δ 1.26(3H, d J 6.5Hz), 1.42(1H, q J 9.2Hz), 2.24(1H, bd J 12.9Hz), 2.38–2.55(2H, m), 2.91–3.07(2H, m), 3.15(1H, d J 10.6Hz), 3.34–3.45(3H, m), 3.58(1H, t J 11.5Hz), 3.72–3.81(3H, m), 3.89(1H, t J 11.4), 4.04(1H, bd J 8.0Hz), 4.35(1H, d J 7.6Hz), 5.05(1H, q J 6.4Hz), 7.12–7.28(5H, m), 7.38(2H, s), 7.87(1H, s) | 2R, 3R, 4R, 8R |
| 94 Free base | 31 | 500 | 1,2,3-triazol-1-yl-CH2— | (400MHz, CDCl3) δ 1.36(3H, d J 6.5Hz), 1.44–1.65(2H, m), 2.36–2.62(2H, m), 3.48(1H, td J 11.8Hz and 2.8Hz), 3.98–4.28(4H, m), 4.94(1H, q J 6.4Hz), 7.08–7.37(8H, m), 7.62(1H, s), 7.66(1H, s). | 2R, 3R, 4R, 8R |
| 95 Free base | 31 | 500 | 1,2,3-triazol-2-yl-CH2— | (400MHz, CDCl3) δ 1.30–1.40(4H, m), 1.46–1.49(1H, m), 2.43–2.65(2H, m) 3.49(1H, t J 11.6Hz), 4.03–4.23(3H, m), 4.25(1H, d J 7.9Hz), 4.94(1H, q J 6.5Hz), 7.10–7.21(4H, m), 7.21–7.31(3H, m), 7.52(2H, s), 7.67(1H, s). | 2R, 3R, 4R, 8R |
| 96 Free base | 31 | 636 | (S)-2-(COOBn)pyrrolidin-1-yl-CH2— | (360MHz, CDCl3) δ 1.19–1.44(4H, m), 1.51–2.00(5H, m), 2.00–2.06(2H, m), 2.28–2.41(2H, m), 2.96–3.02(2H, m), 3.49(1H, dt, J 12.1, 2.0Hz), 4.05–4.12(2H, m), 4.15(1H, d, J 8.3Hz), 4.93(1H, q, J 6.6Hz), 5.08(2H, q, J 12.2Hz), 6.95–7.02(2H, m), 7.12–7.23(5H, m), 7.28–7.39(5H, m), 7.65(1H, s) | 2R, 3R, 4R, 8R, 2'S |

TABLE 4-continued

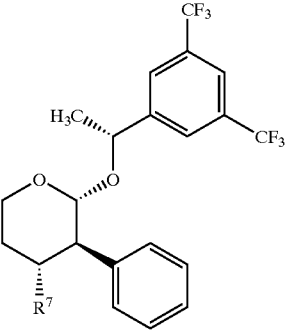

| Ex. No. | From mesylate | MS (ES⁺) M + H | R⁷ | ¹H NMR | Stereochemistry |
|---|---|---|---|---|---|
| 97 Free base | 31 | 546 | 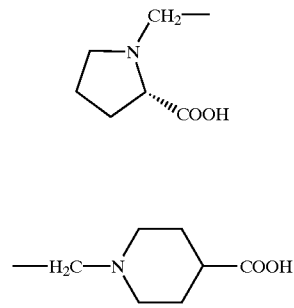 | (360MHz, CDCl₃) δ 1.35(3H, d J 6.6Hz), 1.45–1.60(1H, m), 1.73–1.84(1H, m), 1.86–2.28(5H, m), 2.34–2.42(2H, m), 2.43–2.53(1H, m), 2.46–3.06(1H, m), 3.32–3.39(1H, m), 3.57–3.66(1H, m), 3.78–3.86(1H, m), 4.11–4.19(1H, m), 4.25(1H, d, J 8.1Hz), 4.94(1H, q, J 6.5Hz), 7.00–7.06(2H, m), 7.16(2H, s), 7.26–7.28(3H, m), 7.67(1H, s). | 2R, 3R, 4R, 8R, 2'S |
| 50 | 31 | 560 | 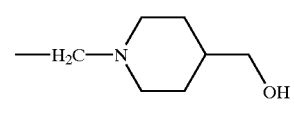 | (400MHz, CDCl₃) δ 1.32(3H, d J 6.5Hz), 1.45–1.57(1H, m), 1.67–2.01(5H, m), 2.21(1H, m), 2.30–2.47(3H, m) 2.63–2.82(2H, m), 3.03(1H, bd J 10.6Hz), 3.26(1H, bd J 10.9Hz), 3.66(1H, t J 12.0Hz), 4.12(1H, dd J 11.8Hz and 4.2Hz), 4.39(1H, d J 7.0Hz), 5.02(1H, q J 6.4Hz), 7.07(2H, d J 7.2Hz), 7.21–7.29(3H, m), 7.31(2H, s), 7.73(1H, s). | 2R, 3R, 4R, 8R |
| 98 Free base | 31 | 546 | 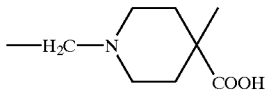 | (400MHz, CDCl₃) δ 1.09–1.50(7H, m), 1.50–1.64(3H, m), 1.88–2.10(5H, m), 2.38(1H, t, J 9.6Hz), 2.65(1H, d, J 10.6Hz), 2.76(1H, d, J 10.6Hz), 3.41(2H, d, J 6.1Hz), 3.52(1H, t, J 11.9Hz), 4.12(1H, dd, J 11.5, 3.4Hz), 4.18(1H, d, J 8.2Hz), 4.94(1H, q J 6.3Hz), 6.95–7.04(2H, m), 7.13–7.28(5H, m), 7.65(1H, s). | 2R, 3R, 4R, 8R |
| 48 | 31 | 574 | 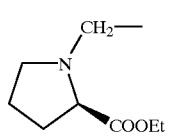 | (400MHz, CDCl₃) δ 0.95(3H, s), 1.06–1.47(7H, m), 1.82–2.78(10H, m), 3.41(1H, t J 11.6Hz), 3.92(1H, dm J 11.6Hz), 4.19(1H, d J 8.2Hz), 4.93(1H, q J 6.5Hz), 6.95–7.05(2H, m), 7.12–7.28(5H, m), 7.67(1H, s). | 2R, 3R, 4R, 8R |
| 99 | 31 | 574 | 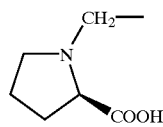 | (400MHz, CDCl₃) δ 1.16(3H, t J 6.4Hz), 1.34(3H, d J 5.9Hz), 1.36–1.48(1H, m), 1.64–2.10(7H, m), 2.21–2.46(3H, m), 2.88–3.02(2H, m), 3.48(1H, td J 11.0Hz 1.9Hz), 3.99–4.20(4H, m), 4.92(1H, q J 6.2Hz), 6.98–7.04(2H, m), 7.15(2H, s), 7.18–7.26(3H, m), 7.65(1H, s). | 2R, 3R, 4R, 8R, 2'R |
| 100 | 31 | 546 | | (360MHz, CDCl₃) δ 1.35(3H, d J 6.6Hz), 1.46–1.61(1H, m), 1.63–1.88(2H, m), 1.90–2.27(4H, m), 2.39(1H, dd J 11.5 8.1Hz), 2.48–2.73(3H, m), 3.22(1H, dd J 9.6Hz 2.5Hz), 3.47–3.62(2H, m), 4.12(2H, dm J 10.4Hz), 4.19(1H, d J 8.1Hz), 4.91(1H, q J 6.5Hz), 6.98–7.06(2H, m), 7.14(2H, s), 7.22–7.31(3H, m), 7.67(1H, s). | 2R, 3R, 4R, 8R, 2'R |

TABLE 4-continued

| Ex. No. | From mesylate | MS (ES+) M + H | R⁷ | ¹H NMR | Stereochemistry |
|---|---|---|---|---|---|
| 101 Free base | 31 | 588 | EtOOC-piperidine-CH₂- (2-substituted piperidine with CO₂Et) | (360MHz, CDCl₃) δ 1.11(3H, t J 7.1Hz), 1.34(3H, d J 6.6Hz), 1.31–1.52(4H, m), 1.59–1.29(2H, m), 1.92–2.05(3H, m), 2.23–2.39(3H, m), 2.62–2.73(1H, m), 3.05–3.12(1H, m), 3.49–3.58(1H, m), 3.90–4.20(4H, m), 4.91(1H, q J 6.6Hz), 6.96–7.02(2H, m), 7.14–7.21(5H, m), 7.65(1H, s). | 2R, 3R, 4R, 8R, 2'R/S isomer 1 |
| 102 Free base | 31 | 588 | EtOOC-piperidine-CH₂- | (360MHz, CDCl₃) δ 1.15–1.29(4H, m), 1.34(3H, d J 6.5Hz), 1.39–1.77(6H, m), 1.93–2.12(4H, m), 2.32(1H, dd J 10.4Hz 8.5Hz), 2.77–2.90(2H, m), 3.52(1H, td J 10.5Hz 1.9Hz), 4.05–4.18(4H, m), 4.93(1H, q J 6.6Hz), 6.96–7.05(2H, m), 7.14–7.23(5H, m), 7.65(1H, s). | 2R, 3R, 4R, 8R, 2'S/R isomer 2 |
| 103 | 31 | 555 | triazolopiperazine-CH₂- | (400MHz, CDCl₃) δ 1.36(3H, d, J 6.6Hz), 1.43–1.50(1H, m), 1.97–2.07(2H, m), 2.24–2.33(2H, m), 2.44(1H, dd, J 11.1, 8.3Hz), 2.65–2.71(1H, m), 2.79–2.85(1H, m), 3.42(1H, d, J 15.6Hz), 3.53(1H, td, J 12.2, 2.0Hz), 3.70(1H, d, J 15.5Hz), 4.02–4.09 (2H, m), 4.14(1H, dd, J 11.8, 3.3Hz), 4.21(1H, d, J 8.3Hz), 4.95(1H, q, J 6.5Hz), 7.02–7.04(2H, m), 7.16(2H, s, br), 7.23–7.26(3H, m), 7.66(1H, s), 7.81(1H, s); | 2R, 3R, 4R, 8R |
| 104 HCl salt | 31 | 532 | 2-(hydroxymethyl)pyrrolidine-N-CH₂- | (360MHz, DMSO) δ 1.26(3H, d, J 6.6Hz), 1.31–1.45(1H, m), 1.57–1.68(1H, m), 1.72–1.81(2H, m), 1.87–1.96(1H, m), 2.22–2.47(5H, m), 3.23–3.33(2H, m), 3.52–3.66(4H, m), 4.06(1H, dd, J 11.0, 2.8Hz), 4.36(1H, d, J 7.9Hz), 5.05(1H, q, J 6.7Hz), 5.41(1H, t, J 4.7Hz), 7.15–7.20(2H, m), 7.20–7.27(3H, m), 7.37(2H, s), 7.87(1H, s) | 2R, 3R, 4R, 8R, 2'S |
| 105 | 31 | 532 | 2-(hydroxymethyl)pyrrolidine-N-CH₂- | (360MHz, CDCl₃), δ 1.36(3H, d, J 6.6Hz), 1.42–1.72(4H, m), 1.97–2.26(5H, m), 2.31–2.48(2H, m), 2.51(1H, dd, J 13.0, 4.7Hz), 2.98–3.03(1H, m), 3.15(1H, dd, J 8.8, 2.0Hz), 3.27(1H, dd, J 10.8, 3.5Hz), 3.55(1H, dt, J 12.0, 2.2Hz), 4.10–4.16(1H, m), 4.18(1H, d, J 8.0Hz), 4.92(1H, q, J 6.6Hz), 7.02–7.08(2H, m), 7.17–7.28(5H, m), 7.65(1H, s). | 2R, 3R, 4R, 8R, 2'R |
| 106 HCl salt | 31 | 560 | 3-carboxypiperidine-N-CH₂- | (360MHz, MeOH), δ 1.33(4H, d J 6.6Hz), 1.52–1.63(1H, m), 1.71–1.89(3H, m), 1.98–2.13(2H, m), 2.42–2.48(1H, m), 2.51–2.62(3H, m), 2.83–3.05(3H, m), 3.69(2H, dt J 12.2, 1.9Hz), 4.13–4.18 (1H, m), 4.42(1H, d J 8.1Hz), 5.03(1H, q J 6.6Hz), 7.13–7.17(2H, m), 7.25–7.32(5H, m), 7.73(1H, s). | 2R, 3R, 4R, 8R, 3'R |

TABLE 4-continued

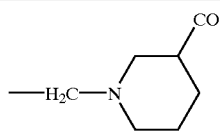

| Ex. No. | From mesylate | MS (ES⁺) M + H | R⁷ | ¹H NMR | Stereochemistry |
|---|---|---|---|---|---|
| 107 HCl salt | 31 | 560 | 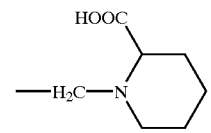 | (360MHz, MeOD) δ 1.35(3H, d J 6.6Hz), 1.57–1.69(1H, m), 1.69–1.79(1H, m), 1.97–2.64(9H, m), 2.65–2.79(1H, m), 2.80–2.90(1H, m), 3.29–3.65(3H, m), 4.10–4.19(1H, m), 4.26(1H, d J 7.6Hz), 4.94(1H, q J 6.7Hz), 7.01–7.08(2H, m), 7.17(2H, s), 7.24–7.30(2H, m), 7.32–7.35(1H, m), 7.67(1H, s). | 2R, 3R, 4R, 8R, 3'S |
| 108 Free base | 31 | 560 | 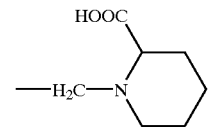 | (360MHz, CDCl₃) δ 1.15–1.81(8H, m), 2.05–2.46(3H, m), 2.65–2.81(2H, m), 2.88–3.07(1H, m), 3.22–3.32(1H, m), 3.52(1H, t J 11.7Hz), 4.10(1H, dm J 12.1Hz), 4.23(1H, d J 8.2Hz), 4.93(1H, q J 6.4Hz), 6.95–7.07(2H, m), 7.17(2H, s), 7.21–7.31(3H, m), 7.67(1H, s). | 2R, 3R, 4R, 8R, 2'R/S isomer 1 |
| 109 Free base | 31 | 560 | 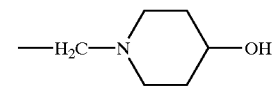 | (360MHz, CDCl₃) δ 1.18–1.78(9H, m), 1.89–2.06(2H, m), 2.18–2.40(4H, m), 2.72–3.62(4H, m), 4.14(1H, dm J 9.7Hz), 4.23(1H, d J 8.1Hz), 4.94(1H, q J 6.6Hz), 6.96–7.07(2H, m), 7.17(2H, s), 7.21–7.33(3H, m), 7.66(1H, s). | 2R, 3R, 4R, 8R, 2'S/R isomer 2 |
| 110 | 31 | 532 | 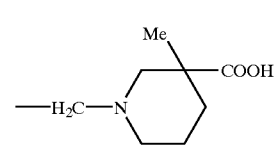 | (360MHz, CDCl₃) δ 1.31–1.57(6H, m), 1.67–1.79(3H, m), 1.84–2.08(5H, m), 2.34–2.48(2H, m), 2.55–2.64(1H, m), 3.48–3.59(2H, m), 4.11–4.21(2H, m), 4.93(1H, q J 6.6Hz), 6.96–7.04(2H, m), 7.16(2H, s), 7.19–7.23(3H, m), 7.65(1H, s). | 2R, 3R, 4R, 8R |
| 53 Free base | 31 | 574 | 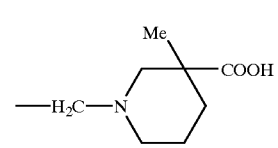 | (360MHz, CDCl₃) δ 1.09(3H, s), 1.35(3H, d J 6.6Hz), 1.45–1.75(5H, m), 1.90(2H, v broad d J 13.1Hz), 2.0(1H, d J 11.7Hz), 2.1–2.25(3H, m), 2.38(1H, dd J 11.2Hz and 9.2Hz), 2.75(1H, d J 11.8Hz), 2.90(1H, d J 9.2Hz), 3.55(1H, td J 12.1Hz and 2.2Hz), 4.16(1H dd J 12.0Hz and 3.1Hz), 4.95(1H q J 6.5Hz), 7.00(2H, m), 7.16(2H, s), 7.25(3H, m), 7.66(1H, s). | 2R, 3R, 4R, 8R, 3'R isomer 1 |
| 54 Free base | 31 | 574 | 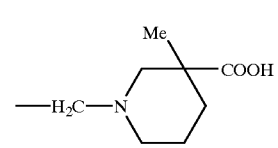 | (360MHz, CDCl₃) δ 1.08(3H, s), 1.35(3H, d J 5.9Hz), 1.54(1H, ddd J 11.1Hz and 3.6Hz), 1.60(2H, d J 11.7Hz), 1.88(2H, m), 2.0–2.2(4H, m), 2.32(2H, m), 2.87(m), 3.56(td J 11.0Hz and 1.6Hz), 4.12(2H, m), 4.21(1H, d J 7.5Hz), 4.94(1H, q J 5.9Hz), 7.01(2H, m), 7.16(2H s), 7.26(3H, m), 7.66(1H, s). | 2R, 3R, 4R, 8R, 3'S isomer 2 |
| 111 Free base | 31 | 560 | 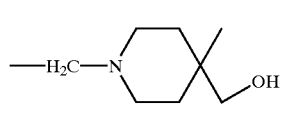 | (360MHz, CDCl₃) δ 0.83(3H, s), 1.14–1.53(8H, M), 1.86–2.48(9H, m), 3.29(2H, s), 3.52(1H, td J 11.9Hz 1.3Hz), 4.12(1H, dd J 11.8Hz 3.6Hz), 4.18(1H, d J 8.3Hz), 4.93(1H, q J 6.5Hz), 6.96–7.04(2H, m), 7.16(2H, s), 7.21–7.26(3H, m), 7.65(1H, s). | 2R, 3R, 4R, 8R |

TABLE 4-continued

| Ex. No. | From mesylate | MS (ES⁺) M + H | R⁷ | ¹H NMR | Stereochemistry |
|---|---|---|---|---|---|
| 112 | 41 | 597 | —H₂C—N(piperidinyl)-(4-methyl-1,2,4-triazol-3-yl) | | 2R, 3R, 4R, 8R |
| 113 | 41 | 554 | —H₂C—N(tetrahydroimidazo[1,5-a]pyrazinyl) | | 2R, 3R, 4R, 8R |
| 114 | 41 | 531 | —H₂C—N(4-methylpiperazinyl) | | 2R, 3R, 4R, 8R |
| 115 HCl salt | 31 | | —H₂C—N(morpholinyl) | (400MHz, DMSO) δ 1.26(3H, d J 6.5Hz), 1.42(1H, q J 9.2Hz), 2.24(1H, bd J 12.9Hz), 2.38–2.55(2H, m), 2.91–3.07(2H, m), 3.15(1H, d J 10.6Hz), 3.34–3.45(3H, m), 3.58(1H, t J 11.5Hz), 3.72–3.81(3H, m), 3.89(1H, t J 11.4), 4.04(1H, bd J 8.0Hz), 4.35(1H, d J 7.6Hz), 5.05(1H, q J 6.4Hz), 7.12–7.28(5H, m), 7.38(2H, s), 7.87(1H, s) | 2R, 3R, 4R, 8R |
| 116 | 31 | 560 | —H₂C—N(3-methyl-3-hydroxymethylpiperidinyl) | (360MHz, CDCl₃) δ 0.68(3H, s), 1.12(1H, td J 13.4Hz and 5.7Hz), 1.36(3H, d J 6.6Hz), 1.4–2.1(11H, m), 2.35(1H, dd J 10.8Hz and 8.5Hz), 2.54(1H, broad s), 2.76(1H, broad s), 3.55(3H, m), 4.12(1H, dd J 7.9Hz and 2.8Hz), 4.18(1H, d J 8.3Hz), 4.95(1H, q J 6.6Hz), 6.99(2H, m), 7.16(2H, s), 7.23(3H, m), 7.65(1H, s). | 2R, 3R, 4R, 8R, 3'R |
| 117 | 31 | 586 | —H₂C—N(2-oxa-1-oxo-spiro[4.5]decyl) | (400MHz, CDCl₃) δ 1.35(1H, d, J 6.6Hz), 1.38–1.48(2H, m), 1.62–1.73(1H, m), 1.80–2.06(10H, m), 2.37(1H, t, J 10.6Hz), 2.56(1H, d, br), 2.68(1H, d, br), 3.52(1H, td, J 11.8, 1.7Hz), 4.10–4.22(4H, m), 4.94(1H, q, J 6.6Hz), 7.00–7.02(2H, m), 7.16(2H, s), 7.21–7.23(3H, m), 7.65(1H, s) | 2R, 3R, 4R, 8R |
| 118 HCl salt | 38 | 574 | —H₂C—H₂C—N(2-carboxypiperidinyl) | (360MHz, MeOD) δ 1.32(3H, d J 6.6Hz), 1.41–2.03(11H, m), 2.19(1H, bd J 14.6Hz), 2.42(1H, bt J 10.5Hz), 2.63–2.82(2H, m), 3.10–3.22(1H, m), 3.62(1H, bt J 11.9Hz), 3.72(1H, bd J 11.4Hz), 4.09(1H, dm J 7.2Hz), 436(1H, dm J 6.9Hz), 5.01(1H, q J 6.2Hz), 7.08–7.14(2H, m), 7.23–7.30(3H, m), 7.32(2H, s), 7.72(1H, s). | 2R, 3R, 4R, 8R, 2'R and 2R, 3R, 4R, 8R, 2'S |

TABLE 4-continued

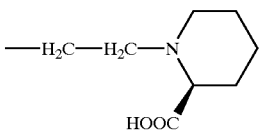

| Ex. No. | From mesylate | MS (ES+) M + H | R7 | 1H NMR | Stereochemistry |
|---|---|---|---|---|---|
| 119 HCl salt | 38 | 574 | —H2C—H2C—N(piperidine-2-COOH) | (360MHz, MeOD) δ 1.31(3H, dd J 4.1Hz 2.4Hz), 1.38–2.02(10H, m), 2.20(1H, dm J 4.1Hz), 2.42(1H, tm J 10.0Hz), 2.79(1H, tm J 12.1Hz), 2.92–3.06(2H, m), 3.40(1H, dm J 12.1Hz), 3.63(1H, tm J 12.5Hz), 3.76(1H, dm J 12.0Hz), 4.09(1H, dm J 12.5Hz), 4.37(1H, dd J 8.4Hz 2.6Hz), 5.01(1H, qm J 4.7Hz), 7.12(2H, dm J 6.6Hz), 7.18–7.28(3H, m), 7.32(2H, s), 7.73(1H, s). | 2R, 3R, 4R, 8R, 2'S and 2R, 3R, 4R, 8R, 2'R |
| 120 | 38 | 574 | —H2C—H2C—N(4-Me-4-CH2OH-piperidine) | (360MHz, CDCl3) δ 0.89(3H, s), 1.20–1.38(7H, m), 1.60–1.4(6H, m), 1.75–1.82(1H, m), 1.83–1.92(1H, m), 2.15–2.35(3H, m), 2.36–2.50(2H, m), 3.33(2H, s), 3.49–3.59(1H, m), 4.11(1H, dd, J 11.2, 3.9Hz), 4.18–4.21(1H, m), 4.93(1H, q, J 7.3Hz), 7.00–7.03(2H, m), 7.16(2H, s), 7.19–7.22(3H, m), 7.65(1H, s) | 2R, 3R, 4R, 8R |
| 121 | 38 | 588 | —H2C—H2C—N(4-Me-4-COOH-piperidine) | | 2R, 3R, 4R, 8R |
| 122 HCl salt | 38 | 516 | —H2C—H2C—N(pyrrolidine) | (360MHz, CDCl3) δ 1.35(3H, d, J 6.6Hz), 1.46–1.67(3H, m), 1.85–1.91(3H, m), 2.08–2.20(3H, m), 2.27–2.32(1H, m), 2.40(1H, dd, J 11.4, 8.3Hz), 2.47–2.53(1H, m), 2.69–2.75(2H, m), 3.30–3.40(1H, m), 3.64(2H, t, Br), 4.12(1H, dd, J 11.8, 3.1Hz), 4.27(1H, d, J 8.3Hz), 4.93(1H, q, J 6.6Hz), 7.07–7.10(2H, m), 7.15(2H, s), 7.25–7.28(3H, m), 7.65(1H, s) | 2R, 3R, 4R, 8R |
| 123 | 38 | | —H2C—H2C—N(pyrazole) | (360MHz, CDCl3) δ 1.34(3H, d, J 6.6Hz), 1.39–1.64(4H, m), 1.68–1.81(2H, m), 1.82–1.92(1H, m), 2.42(1H, td, J 9.8, 2.6Hz), 3.50(1H, td, J 11.8, 1.5Hz), 4.09–4.15(2H, m), 4.25–4.29(2H, m), 4.92(1H, q, J 6.6Hz), 6.91–6.93(2H, m), 7.14(2H, s), 7.18–7.21(2H, m), 7.50(2H, s), 7.64(1H, s); | 2R, 3R, 4R, 8R |
| 124 | 38 | | —H2C—H2C—N(1,2,4-triazole) | (400MHz, CDCl3) δ 1.35(3H, d, J 6.6Hz), 1.46–1.64(2H, m), 1.75(3H, t, Br), 2.43(1H, t, J 9.5Hz), 3.51(1H, t, J 11.8Hz), 3.93(2H, t, J 6.8Hz), 4.11–4.18(2H, m), 4.93(1H, q, 6.6Hz), 6.94(2H, d, J 3.9Hz), 7.15(2H, s), 7.23–7.26(3H, m), 7.65(1H, s), 7.76(1H, s), 7.84(1H, s) | 2R, 3R, 4R, 8R |

TABLE 4-continued

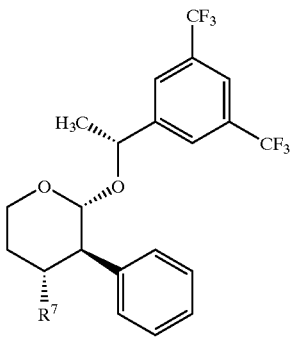

| Ex. No. | From mesylate | MS (ES+) M + H | R7 | 1H NMR | Stereochemistry |
|---|---|---|---|---|---|
| 125 | 38 | | —H2C—H2C—N(tetrazole) | (400MHz, CDCl3) δ 1.34(3H, d, J 6.5Hz), 1.45–1.62(1H, m), 1.66–1.83(3H, m), 1.88–1.96(1H, m), 2.44(1H, t, J 9.0Hz), 3.52(1H, t, J 11.9Hz), 4.11–4.16(2H, m), 4.43–4.47(2H, m), 4.92(1H, q, J 6.5Hz), 6.91–6.92(2H, m), 7.14(2H, s), 7.21–7.22(3H, m), 7.65(1H, s), 8.40(1H, s) | 2R, 3R, 4R, 8R |
| 126 | 38 | | —H2C—H2C—N(tetrazole) | (400MHz, CDCl3) δ 1.35(3H, d, J 6.6Hz), 1.49–1.59(1H, m), 1.64–1.73(2H, m), 1.75–1.83(2H, m), 2.44(1H, t, J 10.5Hz), 3.52(1H, td, J 13.4, 2.5Hz), 4.11–4.26 (4H, m), 4.92(1H, q, J 6.6Hz), 6.90–6.93 (2H, m), 7.15(2H, s), 7.21–7.26(3H, m), 7.66(1H, s), 8.22(1H, s); MS (ES+) m/z 257, 515(M-257, M+ 1H) | 2R, 3R, 4R, 8R |
| 127 HCl salt | 38 | 244, 502 | —H2C—H2C—N(azetidine) | (400MHz, CDCl3) δ 1.34(3H, d, J 6.6Hz), 1.36–1.51(3H, m), 1.83(1H, d, Br), 2.14–2.16(2H, m), 2.37(1H, t, J 11.4Hz), 2.62–2.76(3H, m), 3.19–3.29(1H, m), 3.39–3.49(1H, m), 3.66(1H, t, J 11.6Hz), 3.88–3.98(1H, m), 4.11(1H, dd, J 11.8, 4.3Hz), 4.27(2H, d, J 8.2Hz), 4.93(1H, q, J 6.6Hz), 7.09(2H, d, J 6.6Hz), 7.14(2H, s), 7.22–7.26(3H, m), 7.65(1H, s); | 2R, 3R, 4R, 8R |
| 130 | 38 | 311, 569 | —H2C—H2C—N(triazolopiperazine) | (360MHz, CDCl3) δ 1.15–1.24(1H, m), 1.35(3H, d, J 6.6Hz), 1.41–1.53(2H, m), 1.77(1H, d, br, J 13.3Hz), 1.88–1.97(1H, m), 2.34–2.49(3H, m), 2.59–2.72(2H, m), 3.47–3.58(3H, m), 4.01–4.06(2H, m), 4.11–4.15(1H, m), 4.19(1H, d, J 8.5Hz), 4.94(1H, q, J 6.6Hz), 7.00–7.03(2H, m), 7.16(2H, s), 7.23–7.26(3H, m), 7.65(1H, s), 7.82(1H, s) | 2R, 3R, 4R, 8R |
| 131 HCl salt | 38 | 574 | —H2C—H2C—N(piperidine)—COOH | (360MHz, MeOH) δ 1.33(3H, d, J 6.6Hz), 1.41–1.56(3H, m), 1.66–1.80(3H, m), 1.89–2.01(2H, m), 2.09–2.18(2H, m), 2.43(2H, dd, J 10.8, 7.7Hz), 2.48–2.59 (1H, m), 2.73–2.90(3H, m), 3.01–3.10 (1H, m), 3.30–3.44(1H, m), 3.63(1H, td, J 10.8, 1.7Hz), 4.11(1H, dd, J 12.0, 3.6Hz), 4.38(1H, d, J 8.4Hz), 5.01(1H, q, J 6.6Hz), 7.12–7.14(2H, m), 7.19–7.28(3H, m), 7.32(2H, s), 7.72(1H, s) | 2R, 3R, 4R, 8R |

TABLE 4-continued

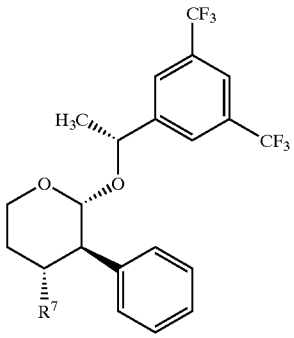

| Ex. No. | From mesylate | MS (ES+) M + H | R7 | 1H NMR | Stereochemistry |
|---|---|---|---|---|---|
| 132 2HCl salt | 38 | 611 | —H2C—H2C—N piperidine-4-yl linked to 1-methyl-1,2,4-triazol-5-yl (Me on N1) | (360MHz, MeOH-d4) δ 1.33(3H, d, J 6.6Hz), 1.47–1.60(3H, m) 1.77–1.83(1H, m), 1.97–2.15(3H, m), 2.20–2.30(2H, m), 2.45(1H, dd, J 8.4, 11.4Hz), 2.87–3.18 (4H, m), 3.40(1H, tt, J 3.5, 12.2Hz), 3.40–3.69(2H, m), 3.66(1H, ddd, J 2.0, 12.1Hz), 3.91(3H, s), 4.12(1H, dd, J 3.2, 11.6Hz), 4.39(1H, d, 8.4Hz), 5.02(1H, q, J 6.6Hz), 7.13–7.16(2H, m), 7.21–7.31(3H, m), 7.33(2H, s), 7.72(1H, s), 9.50(1H, s). | 2R, 3R, 4R, 8R |
| 133 | 42 | 568 | —H2C—H2C—N (5,6,7,8-tetrahydroimidazo[1,5-a]pyrazin-7-yl) | | 2R, 3R, 4R, 8R |
| 134 | 42 | 545 | —H2C—H2C—N N—Me (4-methylpiperazin-1-yl) | | 2R, 3R, 4R, 8R |
| 135 | 42 | 546 | —H2C—H2C—N—OH (4-hydroxypiperidin-1-yl) | | 2R, 3R, 4R, 8R |
| 136 | 42 | 532 | —H2C—H2C—N O (morpholin-4-yl) | | 2R, 3R, 4R, 8R |
| 137 | 38 | 560 | —H2C—H2C—N—CH2OH (4-(hydroxymethyl)piperidin-1-yl) | (400MHz, CDCl3) δ 1.35(3H, d, J 6.6Hz), 1.38–1.72(9H, m), 1.73–1.86(3H, m), 2.14–2.21(2H, m), 2.40(1H, dt, J 8.5, 2.9Hz), 2.63–2.74(2H, m), 3.44(2H, d, J 6.4Hz), 3.54(1H, dt, J 12.2, 2.0Hz), 4.11(1H, dd, J 11.8, 3.4Hz), 4.18(1H, d, J 8.4Hz), 4.93(1H, q, J 6.5Hz), 6.99–7.03(2H, m), 7.14–7.17(2H, m), 7.18–7.23(3H, m), 7.65(1H, s). | 2R, 3R, 4R, 8R |
| 138 | 38 | 546 | —H2C—H2C—N (3-hydroxypiperidin-1-yl) | (400MHz, MeOH) δ 1.33(3H, d, J 6.6Hz), 1.39–1.70(5H, m), 1.71–1.81(2H, m), 1.88–2.0(1H, m), 2.42(1H, dt, J 11.3, 2.6Hz), 2.67–2.90(2H, m), 2.95–3.28 (3H, m), 3.29–3.32(3H, m), 3.63(1H, dt, J 12.1, 2Hz), 4.08–4.14(1H, m), 4.37(1H, d, J 8.4Hz), 5.01(1H, q, 6.6Hz), 7.10–7.15 (2H, m), 7.19–7.28(3H, m), 7.32(2H, s), 7.72(1H, s) | 2R, 3R, 4R, 8R, 3'R |

TABLE 4-continued

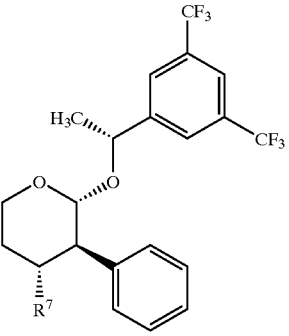

| Ex. No. | From mesylate | MS (ES+) M + H | R7 | 1H NMR | Stereochemistry |
|---|---|---|---|---|---|
| 139 | 38 | | 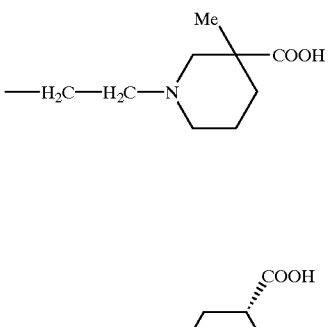 | (360MHz, CDCl3) δ 1.1(4H, s+m), 1.25(1H, m), 1.35(3H, d J 6.6Hz), 1.43(1H, dd J 12.3Hz and 4.13Hz), 1.49(2H, m), 1.73–1.9(5H, m), 2.03(1H d), 2.40(1H, dd J 11.2Hz and 8.5Hz), 2.48(2H dd J 8.1Hz and 6.4Hz), 2.96(1H d J 11.5Hz), 3.57(1H td J 12.1Hz and 1.91Hz), 4.13(1H1H dd J 11.7Hz and 4.25Hz), 4.23(1H d J 8.4Hz), 4.95(1H, q J 6.55Hz), 7.03(2H, m), 7.16(2H s), 7.25(3H m), 7.67(1H, s). | 2R, 3R, 4R, 8R, 3′R/S isomer 1 |
| 140 HCl salt | 38 | 574 | 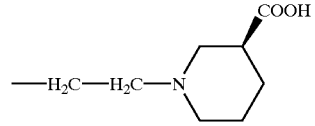 | (400MHz, MeOH) δ 1.33(3H, d J 6.6Hz), 1.42–1.58(3H, m), 1.60–1.80(3H, m), 1.90–2.01(2H, m), 2.02–2.19(1H, m), 2.44(1H, t, J 11.2Hz), 2.57–2.69(1H, m), 2.70–2.93(3H, m), 2.98–3.20(2H, m), 3.43–3.56(1H, m), 3.63(1H, dt, J 12.1, 1.8Hz), 4.11(1H, dd, 11.6, 3.4Hz), 4.38(1H, d, J 8.4Hz), 5.01(1H, q, J 6.6Hz), 7.10–7.15(1H, m), 7.19–7.29(3H, m), 7.31–7.32(2H, m), 7.72(1H, s), | 2R, 3R, 4R, 8R, 3′R |
| 141 HCl salt | 38 | | 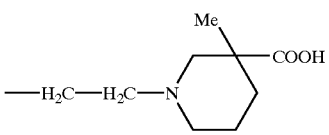 | (360MHz, MeOD) δ 1.32(3H, d J 6.6Hz), 1.38–2.15(10H, m), 2.39–2.46(1H, m), 2.65–3.13(5H, m), 3.39–3.49(1H, m), 3.64(1H, t J 10.8Hz), 4.11(1H, dd J 11.8 3.8Hz), 4.38(1H, d J 8.4Hz), 5.01(1H, q J 6.4Hz), 7.08–7.28(5H, m), 7.32(2H, s), 7.73(1H, s). | 2R, 3R, 4R, 8R, 3′S |
| 142 | 38 | | 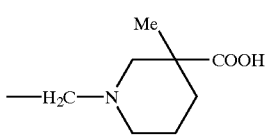 | (360MHz, CDCl3) δ 1.1(3H, s), 1.25(1H, m), 1.15(1H, m), 1.35(3H, d J 6.6Hz), 1.43–2.2(10H, m), 2.33(1H m), 2.39(1H, dd J 11.5Hz and 8.5Hz), 2.80(1H d J 10.8Hz), 3.51(1H td J 12.2Hz and 2.2Hz), 4.05(2H m), 4.19(1H d J 8.5Hz), 4.95(1H, q J 6.6Hz), 7.04(2H, m), 7.11(2H s), 7.21(3H m), 7.65(1H, s) | 2R, 3R, 4R, 8R, 3′R/S isomer 2 |
| 143* | | 592 | 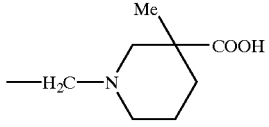 | | 2R, 3R, 4R, 8R, 9(3′S) |
| 144* | | 592 | 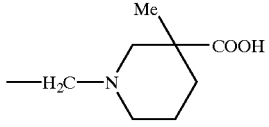 | (360MHz, CDCl3) δ 1.16–1.20(3H, s), 1.34(3H, d, J 6.6Hz), 1.37–1.48(1H, m), 1.55–1.84(3H, m), 2.08(2H, t, J 14.0Hz), 2.40–2.63(3H, m), 2.69(1H, d, J 13.1Hz), 2.78(1H, d, J 12.4Hz), 3.04(1H, dd, J 13.4, 9.5Hz), 3.46–3.55(1H, m), 3.68(1H, td, J 12.0, 1.9Hz), 4.15(1H, dd, J 11.9, 2.9Hz), 4.37(1H, d, J 7.7Hz), 5.04(1H, q, J 6.5Hz), 7.01(2H, t, J 8.7Hz), 7.16–7.20(2H, m), 7.34(2H, s), 7.76(1H, s) | 2R, 3R, 4R, 8R, 9(3′R) |

TABLE 4-continued

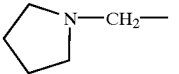

| Ex. No. | From mesylate | MS (ES+) M + H | R7 | 1H NMR | Stereochemistry |
|---|---|---|---|---|---|
| 145 HCl salt | 31 | 502 | ⟨N⟩—CH2— (pyrrolidinylmethyl) | (360MHz, CDCl3) δ 1.35(3H, d, J 6.6Hz), 1.50–1.75(1H, m), 1.76–1.92(2H, m), 2.10–2.30(4H, m), 2.35–2.42(1H, m), 2.49–2.63(2H, m), 2.80(1H, bd, J 13.9Hz), 2.91(1H, dt, J 10.3, 1.8Hz), 3.53–3.65 (2H, m), 3.75–3.85(1H, m), 4.17–4.26 (2H, m), 4.94(1H, q, J 6.6Hz), 7.00–7.06 (2H, m), 7.15(2H, s), 7.24–7.31(3H, m), 7.67(1H, s), 12.29(1H, s) | 2R, 3R, 4R, 8R |

*Examples 143 and 144 are the analogues of Examples 54 and 53, respectively, containing the 3'(4-fluorophenyl) group in place of the 3-phenyl group. The intermediates were prepared containing the 4-fluorophenyl by methods analogous to those described in the preparations leading to Examples 54 and 53.

EXAMPLE 147

(2R,3S,4R,8R)-2-(1-(1-(3,5-bis(Trifluoromethyl) phenyl)ethyl)oxy)-3-(4-fluoro)phenyl-4-vinyl-3,4,5, 6-tetrahydropyran; and (2R,3R,4S,8R)-2-(1-(1-(3,5-Bis(Trifluoromethyl)phenyl)ethyl)oxy)-3-(4-fluoro) phenyl-4-vinyl-3,4,5,6-tetrahydropyran The title compounds were prepared from the mixture of lactol isomers of trans 3-(4-fluoro)phenyl-4-vinyltetrahydropyran-2-ol (Description 20) and (R)-1-(3,5-bis(trifluoromethyl)phenyl)ethanol by a procedure analogous to Example 4. 2,3-trans-3,4-trans isomer 4 (2R,3R,4S, 8R): 1H NMR (400 MHz, CDCl3) δ 1.37 (3H, d, J 6.6 Hz), 1.68–1.74 (2H, m), 2.35–2.46 (1H, m), 2.51 (1H, dd, J 11.6, 8.3 Hz), 3.52–3.60 (1H, m), 4.11–4.18 (1H, m), 4.17 (1H, d, J 8.3 Hz), 4.74–4.82 (2H, m), 4.96 (1H, q, J 6.6 Hz), 5.41–5.49 (1H, m), 6.90–7.00 (4H, m), 7.19 (2H, s), 7.68 (1H, s).

EXAMPLE 148

(2R,3R,4R,SR)-2-(1-(1-(3,5-bis(Trifluoromethyl) phenyl)ethyl)oxy)-4-hydroxymethyl-3-(4-fluoro) phenyl-3,4,5,6-tetrahydropyran The title compound was prepared from isomer 4 (Example 147) by a procedure analogous to that described in Example 5.

1H NMR (360 MHz, CDCl3) δ 1.38 (3H, d, J 6.6 Hz), 1.50–1.72 (2H, m), 1.78–1.97 (2H, m), 2.56 (1H, dd, J 11.6, 8.4 Hz), 3.24 (1H, dd, J 10.8, 6.7 Hz), 3.38 (1H, dd, J 10.8, 3.5 Hz), 3.56 (1H, td, J 12.1, 2.4 Hz), 4.09–4.20 (2H, m), 4.96 (1H, q, J 6.6 Hz), 6.92–7.04 (4H, m), 7.19 (2H, s), 7.68 (1H, s).

EXAMPLE 149

(2R,3R,4R,8R)-2-(1-(1-(3,5-bis(Trifluoromethyl) phenyl)ethyl)oxy)-4-(methanesulfonyloxy)methyl-3-(4-fluoro)phenyl-3,4,5,6-tetrahydropyran The title compound was prepared from the product of Example 148 by a procedure analogous to that described in Example 6.

1H NMR (400 MHz, CDCl3) δ 1.37 (3H, d, J 6.6 Hz), 1.74 (1H, qd, J 14.9, 4.6 Hz), 1.81–1.90 (1H, m), 2.09–2.21 (1H, m), 2.60 (1H, dd, J 11.8, 8.3 Hz), 2.86 (3H, s), 3.56 (1H, td, J 12.0, 2.4 Hz), 3.79 (1H, dd, J 9.9, 6.8 Hz), 3.91–3.96 (1H, m), 4.15–4.19 (2H, m), 4.96 (1H, q, J 6.6 Hz), 6.95–7.05 (4H, m), 7.18 (2H, s), 7.69 (1H, s).

EXAMPLE 150A (2R,3R,4R,8R)-2-[1-(3,5-bis(Trifluoromethyl) phenyl)ethoxy]-4-ethynyl-3-phenyl-3,4,5,6-tetrahydropyran The aldehyde product of Example 45 (0.5 g, 1.12 mmol) was dissolved in methanol and the solution was cooled to 0° C. Potassium carbonate (0.309 g, 2.24 mmol) and dimethyl (1-diazo-2-oxopropyl)phosphonate (0.302 g, 1.68 mmol) were added and the reaction was warmed to room temperature and stirred under an atmosphere of nitrogen for 16 hours. The reaction was diluted with water and the product was extracted into hexane. The combined organic extracts were washed with brine, dried (magnesium sulfate) and evaporated to afford the title compound as a yellow oil.

1H NMR (400 MHz, CDCl3) δ 1.36 (3H, d, J 6.6 Hz), 1.88 (1H, d, J 1.9 Hz), 1.89–1.98 (2H, m), 2.69–2.73 (2H, m), 3.51 (1H, td, J 11.6, 3.4 Hz), 4.11 (1H, dm, J 12.04 Hz), 4.19 (1H, d, J 8.0 Hz), 4.95 (1H, q, J 6.6 Hz), 7.06–7.09 (2H, m), 7.20 (2H, s), 7.24–7.28 (3H, m), 7.67 (1H, s).

EXAMPLE 150B (2R,3R,4R,8R)-(3-(2-[1-(3,5-bis(Trifluoromethyl) phenyl)ethoxy]-4-(3-dimethylaminoprop-1-ynyl)-3-phenyl-3,4,5,6-tetrahydropyran The acetylene product of Example 150A (0.543 g, 1.23 mmol) was dissolved in dioxane and paraformaldehyde (55mg, 1.85 mmol), dimethylamine (1.23 ml of a 2M solution in tetrahydrofuran) and copper (I) chloride (6mg, 0.061 mmol) were added. The reaction mixture was heated to 80° C. under an atmosphere of nitrogen for 3 hours. The reaction mixture was evaporated to dryness and purified on alumina, eluting with 10% ethyl acetate in hexane, increasing to 50% ethyl acetate in hexane. The resultant title compound was afforded as an off white solid.

$^1$H NMR (360 MHz, CDCl$_3$) δ 1.36 (3H, d, J 6.6 Hz), 1.90–1.93 (2H, m), 1.97 (6H, s), 2.70–2.72 (2H, m), 3.01–3.02 (2H, m), 3.51 (1H, td, J 14.4, 3.4 Hz), 4.09 (1H, dm, J 14.4 Hz), 4.19 (1H, d, J 8.0 Hz), 4.95 (1H, q, J 6.6 Hz), 7.06–7.08 (2H, m), 7.20–7.26 (5H, m), 7.67 (1H, s); MS (ES$^+$) m/z 242 (M−257), 500 (M+1).

EXAMPLE 151A (2R,3R,4R,8R)-2-[1-(3,5-bis(Trifluoromethyl) phenyl)ethoxy]-4-(3-hydroxyprop-1-ynyl)-3-phenyl-3,4,5,6-tetrahydropyran The acetylene product of Example 150A (0.331 g, 0.75 mmol) was dissolved in tetrahydrofuran and cooled to a temperature of −78° C. n-Butyl lithium (0.47 ml of a 1.6M solution in hexanes) was added dropwise and the reaction was stirred at −78° C. for 20 minutes. Paraformaldehyde (44 mg, 1.5 mmol) was added to the mixture and the reaction was stirred for a further 30 minutes. Further paraformaldehyde (44 mg) was added and the reaction stirred at −78° C. for 10 minutes. The reaction was diluted with water and the product extracted into ethyl acetate. The combined organic extracts were washed with brine, dried (magnesium sulfate) and concentrated in vacuo to afford a yellow oil. This was purified on silica, eluting with 20% ethyl acetate in hexane to afford the title compound.

$^1$H NMR (400 MHz, CDCl$_3$) δ 1.36 (3H, d, J 6.6 Hz), 1.81–1.96 (2H, m), 2.65–2.78 (2H, m), 3.51 (1H, td, J 11.6, 3.0 Hz), 4.03 (2H, d, J 1.5 Hz), 4.07–4.15 (2H, m), 4.20 (1H, d, J 8.0 Hz), 4.95 (1H, q, J 6.6 Hz), 7.03–7.08 (2H, m), 7.21 (2H, s), 7.23–7.26 (3H, m), 7.67 (1H, s).

EXAMPLE 151B (2R,3R,4R,8R)-2-[1-(3,5-bis(Trifluoromethyl) phenyl)ethoxy]-4-(3-methansulfonyloxyprop-1-ynyl)-3-phenyl-3,4,5,6-tetrahydropyran The title compound was prepared from the alcohol product of Example 151A by a procedure analogous to that described in Example 6.

$^1$H NMR (360 MHz, CDCl$_3$) δ 1.36 (3H, d, J 6.6 Hz), 1.90–1.94 (2H, m) 2.50 (3H, s), 2.69–2.87 (2H, m), 3.52 (1H, td, br), 4.07–4.14 (1H, dm, br), 4.16 (1H, d, J 8.1 Hz), 4.67 (2H, d, J 2.0 Hz), 4.94 (1H, q, J 6.6 Hz), 7.05–7.08 (2H, m), 7.16 (2H, s), 7.24–7.26 (3H, m), 7.67 (1H, s).

EXAMPLE 151C (2R,3R,4R,8R)-2-[1-(3,5-bis(Trifluoromethyl) phenyl)ethoxy]-4-(3-azidoprop-1-ynyl)-3-phenyl-3,4,5,6-tetrahydropyran The mesylate product of Example 151B (0.265 g, 0.48 mmol) was stirred under nitrogen in dimethylformamide and sodium azide (0.094 g, 1.45 mmol) was added. The reaction mixture was stirred at room temperature for 16 hours then diluted with water and the product extracted into ethyl acetate. The ethyl acetate extracts were combined, washed with water, brine, dried (magnesium sulfate) and concentrated in vacuo to afford the title compound as a colourless oil.

$^1$H NMR (400 MHz, CDCl$_3$) δ 1.36 (3H, d, J 6.6 Hz), 1.85–2.01 (2H, m), 2.69–2.81 (2H, m), 3.52 (1H, td, J 11.5, 3.0 Hz), 3.69 (2H, d, J 1.6 Hz), 4.11 (1H, dm, br), 4.21 (1H, d, J 7.9 Hz), 4.95 (1H, q, J 6.6 Hz), 7.05–7.09 (2H, m), 7.21 (2H, s), 7.23–7.26 (3H, m), 7.67 (1H, s).

EXAMPLE 151D (2R,3R,4R,8R)-(5-{2-[1-(3,5-bis(Trifluoromethyl) phenyl)ethoxy]-3-phenyl-3,4,5,6-tetrahydropyran-4-yl}-4-dimethylamino-2H-[1,2,3]triazole The azide product of Example 151C (0.102 g) was dissolved in dioxane (1 ml) and excess dimethylamine was added. The reaction vessel was sealed and the reaction mixture was stirred for 16 hours at 80° C. The reaction mixture was cooled, and concentrated in vacuo to afford an orange residue. This was purified on silica, eluting with 5% methanol, 0.5% ammonia in dichloromethane, increasing to 7% methanol, 0.5% ammonia in methanol to afford the title compound as an off white solid.

$^1$H NMR (360 MHz, CDCl$_3$) δ 1.38 (3H, d, J 6.6 Hz), 1.78 (1H, dm, J 13.8 Hz), 2.03 (6H, s), 2.13–2.28 (1H, m), 2.94–3.18 (3H, m), 3.21–3.30 (1H, m), 3.67 (1H, td, J 10.8, 2.2 Hz), 4.20 (1H, dd, br), 4.41 (1H, d, J 8.4 Hz), 5.02 (1H, q, J 6.6 Hz), 6.89–6.92 (2H, m), 7.06–7.09 (3H, m), 7.24 (2H, s), 7.69 (1H, s); MS m/z (ES$^+$) 285 M−257), 543 (M+H).

EXAMPLE 152

(2R,3R,4R,8R)-5-{2-[1-(3,5-bis(Trifluoromethyl) phenyl)ethoxy]-3-phenyl-3,4,5,6-tetrahydropyran-4-yl}-1H-imidazole i) A solution of tosylmethyl isocyanide (0.07 g, 0.36 mmol) in dimethoxyethane (0.5 ml) was added to a stirred suspension of potassium t-butoxide (0.056 g, 0.5 mmol) in dimethoxyethane under an atmosphere of nitrogen at −30° C. A solution of the aldehyde product of Example 45 (0.160 g, 0.36 mmol) in dimethoxyethane was added dropwise to the reaction mixture at −30° C. and the reaction was stirred for 1 hour. Ice water was added to the mixture followed by a saturated solution of ammonium chloride and the product was extracted into dichloromethane. The combined organic extracts were washed with brine, dried (magnesium sulfate) and concentrated in vacuo to afford a brown solid.

ii) Phosphorus oxychloride (0.047 ml, 0.5 mmol) was added to a solution of the formamide, described in step (i), in dimethoxyethane (0.25 ml) at −30° C. Triethylamine (0.087 ml, 0.84 mmol) was added as a solution in dimethoxyethane (0.5 ml) and the reaction mixture was warmed to −10° C. and stirred under an atmosphere of nitrogen for 1 hour. A saturated solution of sodium bicarbonate was added to the mixture and the product was extracted into ethyl acetate. The combined organic extracts were washed with brine, dried (magnesium sulfate) and concentrated in vacuo to afford a brown oil.

iii) The compound of step (ii) was dissolved in a 2M solution of ammonia in methanol (5 ml) and stirred at room temperature under an atmosphere of nitrogen for 66 hours. The reaction mixture was evaporated to dryness to afford the title compound as a yellow solid. MS m/z (ES$^+$) 227 (M−257), 485 (M+H).

EXAMPLE 153

(2R,3S,4S,8R)-(3-{2-[1-(3,5-bis(Trifluoromethyl) phenyl)ethoxyl]-4-(3-dimethylaminoprop-1-ynyl)-3-phenyl-3,4,5,6-tetrahydropyran i) (2R,3S,4S,8R)-2-[1-(3,5-bis(Trifluoromethyl)phenyl) ethoxy]-4-ethynyl-3-phenyltetrahydropyran The title compound was prepared by a method analogous to that described in Example 150A from the aldehyde described in Example 43.

$^1$H NMR (400 MHz, CDCl$_3$) δ 1.43 (3H, d, J 6.6 Hz), 1.87 (1H, d, J 2.3 Hz), 1.98 (1H, dddd, J 4.8, 12.7, 12.7, 12.7), 2.09–2.13 (1H, m), 2.94 (1H, dd, J 3.8, 12.0 Hz), 3.39–3.47 (1H, m), 3.71–3.77 (1H, m), 3.97 (1H, dt, J 2.6, 12.8 Hz), 4.51 (1H, d, J 3.0 Hz), 4.84 (1H, q, J 6.6 Hz), 7.17 (2H, s), 7.21–7.33 (5H, m), 7.61 (1H, s).

(ii) (2R,3S,4S,8R)-(3-{2-[1-(3,5-bis(Trifluoromethyl) phenyl)ethoxy]-4-(3-dimethylaminoprop-1-ynyl)-3-phenyltetrahydropyran The title compound was prepared from the product of step (i) by a method analogous to that described in Example 160B.

$^1$H NMR (400 MHz, CDCl$_3$) δ 1.43 (3H, d, J 6.6 Hz), 1.94 (6H, s), 1.92–2.00 (1H, m), 2.05–2.12 (1H, m), 2.91 (1H, dd, J 12.0, 3.0 Hz), 3.02 (2H, d, J 1.9 Hz), 3.42–3.50 (1H, m), 3.70–3.74 (1H, m), 3.94–4.02 (1H, m), 4.52 (1H, d, J 3.0 Hz), 4.84 (1H, q, J 6.6 Hz), 7.20 (2H, s), 7.22–7.27 (5H, m), 7.61 (1H, s). MS (ES$^+$) m/z 500 (M+H, 100%).

EXAMPLE 154

(2R,3S,4S,8R)-(3-{2-[1-(3,5-bis(Trifluoromethyl) phenyl)ethoxy]-4-(4-dimethylaminobut-2-ynyl)-3-phenyl-3,4,5,6-tetrahydropyran i) (2R,3S,4S,8R)-2-[1-(3,5-bis(Trifluoromethyl)phenyl) ethoxy]-4-(prop-2-nyl)-3-phenyltetrahydropyran The title compound was prepared by a method analogous to that described in Example 150A from the aldehyde described in Example 44.

$^1$H NMR (360 MHz, CDCl$_3$) δ 1.46 (3H, d, J 6.6 Hz), 1.74 (1H, dddd, J 5.1, 13.0, 13.0, 13.0), 1.85 (1H, dddd, J, 2.5, 8.0, 8.0, 8.0 Hz), 1.95 (1H, t, J 2.5 Hz), 1.99–2.03 (1H, m), 2.18 (1H, dt, J 2.8, 16.8 Hz), 2.58–2.67 (1H, m), 2.74 (1H, dd, J 3.1, 12.0 Hz), 3.79 (1H, dd, J 4.9, 11.1 Hz), 4.06 (1H, dt, J 2.4, 13.2 Hz), 4.46 (1H, d, J 3.1 Hz), 4.88 (1H, q, J 6.6 Hz), 7.22 (2H, s), 7.24–7.33 (5H, m), 7.60 (1H, s).

ii) (2R,3S,4S,8R)-(3-{2-[1-(3,5-bis(Trifluoromethyl) phenyl)ethoxy]-4-(4-dimethylaminobut-2-ynyl)-3-phenyltetrahydropyran The title compound was prepared from the product of Example 154 (i) by a method analogous to that described in Example 150B.

$^1$H NMR (400 MHz, CDCl$_3$) δ 1.45 (3H, d, J 6.6 Hz), 1.74 (1H, dddd, J 5.0, 13.0, 13.0, 13.0 Hz), 1.90 (1H, ddt), 1.98–2.06 (1H, m), 2.20 (1H, dd, J 2.9, 14.0 Hz), 2.28 (6H, s), 2.55–2.67 (1H, m), 2.73 (1H, dd, J 3.1, 12.0 Hz), 3.20 (2H, br s), 3.76–3.81 (1H, m), 4.05 (1H, dt), 4.46 (1H, d, J 3.1 Hz), 4.88 (1H, q, J 6.6 Hz), 7.21 (2H, s), 7.23–7.29 (5H, m), 7.59 (1H, s). MS (ES$^+$) m/z 514 (MH$^+$, 100%)

EXAMPLE 155

(2R,3R,4R,8R)-2-[1-(3,5-bis(Trifluoromethyl) phenyl)ethoxy]-3-phenyl-3,4,5,6-tetrahydropyran-4-carboxylic Acid The aldehyde product of Example 45 (1.5 g) was dissolved in a 1:1 mixture of CH$_2$Cl$_2$/H$_2$O and cooled to 0° C. before the portionwise addition of the sulfamic acid (1.27 g). Sodium chlorite (0.88 g) was added and the reaction was allowed to warm to room temperature and stirred for 1 hour. The solution was dispersed between CH$_2$Cl$_2$ and H$_2$O and the aqueous layer extracted with CH$_2$Cl$_2$ (3×), the combined organics were washed in brine and dried over MgSO$_4$. After filtration the solvent was removed in vacuo to afford a yellow foam which was purified by chromatography on silica eluting with 1–5% MeOH in CH$_2$Cl$_2$ (with 0.2% NH$_3$) gave the title compound as a white foam (0.5 g).

$^1$H NMR (400 MHz, CDCl$_3$) δ 1.34(3H, d, J 6.6 Hz), 1.85–1.98(2H, m), 2.77–2.85(1H, m), 3.01(1H, dd, J 11.2, 8.0 Hz), 3.57(1H, tm, J 11.9 Hz), 4.15(1H,dm, J 11.9 Hz), 4.23(1H, J 8.1 Hz), 4.93(1H, q, J 6.6 Hz), 7.03–7.11(2H, m), 7.15–7.23(5H, m), 7.67(1H, s).

EXAMPLE 156

(2R,3R,4R,8R)-2-[1-(3,5-bis(Trifluoromethyl) phenyl)ethoxy]-3-phenyl-3,4,5,6-tetrahydropyran-4-isocyanate The acid product described in Example 155 (2.6 g), diphenylphosphorylazide (1.4 ml), triethylamine (2.03 ml) and toluene (75 ml) were heated at 90° C. for 3 hours behind a blast shield. The reaction was dispersed between ethyl acetate and saturate potassium carbonate solution. The aqueous layer was extracted with ethyl acetate (3×) and the combined organic phases were washed with brine and dried over magnesium sulphate. After filtration the solvent was removed in vacuo to afford a brown oil which was purified by flash chromatography on silica gel eluting with 0–5–10–20–30% ethyl acetate in hexane to afford the title compound as a white crystalline solid (0.78 g yield 30%)

$^1$H NMR (400 MHz, CDCl$_3$) δ 1.38(3H, d, J 7.3 Hz), 1.79–1.92(1H, m), 1.99–2.08(1H, m), 2.75(1H, dd, J 11.8, 9.0 Hz), 3.49(1H, td, J 13.4, 2.6 Hz), 3.65–3.78(1H, m), 4.07–4.15(1H, m), 4.24(1H, d, J 9.0 Hz), 4.95(1H, q, J 7.3 Hz), 7.05–7.13(2H, m), 7.18–7.38(5H, m), 7.68(1H, s).

EXAMPLE 157

(2R,3R,4R,8R)-4-Amino-2-[1-(3,5-bis (Trifluoromethyl)phenyl)ethoxy]-3-phenyl-3,4,5,6-tetrahydropyran The isocyanate product of Example 156 (0.4 g) was dissolved in tetrahydrofuran (5 ml) and 2N hydrochloric acid (0.44 ml) and water (0.5 ml) and heated at 100° C. for 90 mins. The tetrahydrofuran was removed in vacuo and the residue dispersed between ethyl acetate and saturated potassium carbonate solution. The aqueous layer was extracted with ethyl acetate (3×), the combined organic phases were washed with brine, dried over MgSO$_4$, filtered and solvent removed in vacuo to afford a clear oil. The residue was purified by flash chromatography on silica eluting with 1–5% MeOH in CH$_2$Cl$_2$ (containing 0.2% ammonia) to afford the title compound (0.08 g yield 22%)

$^1$H NMR (360 MHz, CDCl$_3$) δ 1.36(3H, d, J 6.7 Hz), 1.55–1.68(1H, m), 1.87(1H, bd, J 13.1 Hz), 2.43(1H, dd, J 10.4, 8.5 Hz), 3.03(1H, td, J 10.8, 4.3 Hz), 3.54(1H, td, J 12.2, 2.2 Hz), 4.12(1H, ddd, J 12.0, 4.6, 1.6 Hz), 4.22(1H, d, J 8.5 Hz), 4.95(1H, q, J 6.6 Hz), 7.03–7.12(2H, m), 7.17–7.32(5H, m), 7.67(1H, s).

EXAMPLE 158

(2R,3R,4R,8R)-2-[1-(3,5-bis(Trifluoromethyl) phenyl)ethoxy]4-(morpholin-4-yl)-3-phenyl-3,4,5,6-tetrahydropyran The amine product of Example 157 (0.075 g), potassium carbonate (0.096 g), 2-bromoethyl ether (0.043 ml), sodium iodide (0.013 g) and ethanol (15 ml) were heated together under an atmosphere of nitrogen for 48 hours. The solvent was removed in vacuo and the residue dispersed between water and ethyl acetate.

The aqueous layer was extracted with ethyl acetate(3x), the combined organic phases were washed with brine, dried over MgSO$_4$, filtered and the solvent removed in vacuo. Purification by flash silica chromatography eluting with 0–3%MeOH in CH$_2$Cl$_2$ (containing 0.2% ammonia) to afford the title compound as a clear oil (45 mg yield 52%).

The hydrochloride salt was formed using ethereal HCl and the salt was recrystallised from isohexane/ethyl acetate. MS (ES$^+$) m/z 504 (M+H, 100%) $^1$H NMR (360 MHz, CDCl$_3$) δ 1.35(3H, d, J 6.6 Hz), 1.71–1.85(2H, m), 2.22–2.35(2H, m), 2.51–2.62(2H, m), 2.75–2.91(2H, m), 3.31–3.52(5H, m), 4.11–4.24(2H, m), 4.92(1H, q, J 6.5 Hz), 6.97–7.08(2H, m), 7.15–7.31(5H, m), 7.66(1H, s).

EXAMPLE 159

(2R,3R,4R,8R)-2-[1-(3,5-bis(Trifluoromethyl)phenyl)ethoxy]-4-(piperidin-1-yl)-3-phenyl-3,4,5,6-tetrahydropyran The amine product of Example 157 (0.08 g), potassium carbonate (0.1 g), sodium iodide (0.014 g), 1,5-dibromopentane (0.028 ml) and dimethylformamide (3 ml) were stirred together under an atmosphere of nitrogen at 100° C. for 48 hours. The solvent was removed in vacuo and the residue dispersed between water and ethyl acetate. The aqueous layer was extracted with ethyl acetate(3x), the combined organic phases were washed with brine, dried over MgSO$_4$, filtered and the solvent removed in vacuo. Purification of the residue was by flash chromatography on silica gel, eluting with 0–3%MeOH in CH$_2$Cl$_2$ (containing 0.2% ammonia) to give an oil (50 mg yield 50%). The product was further purified on flash silica eluting with isohexane containing increasing concentrations (25–100%) of ethyl acetate to give the title compound as a white solid (25 mg) which was recrystallised from boiling isohexane.

MS (ES$^+$) m/z 502 (M+H, 100%) $^1$H NMR (400 MHz, CDCl$_3$) δ 1.15–1.31(5H, m), 1.35(3H, d, J 6.6 Hz), 1.57–1.82(3H, m), 2.12–2.22(2H, m), 2.44–2.57(2H, m), 2.75–2.85(2H, m), 3.43(1H, td, J 11.8, 3.6 Hz), 4.12(1H, dt, J 11.8, 30 Hz)4.18(1H, d, J 7.9 Hz), 4.91(1H, q, J 6.6 Hz), 6.96–7.04(2H, m), 7.12–7.22(5H, m), 7.65(1H, s).

EXAMPLE 160

(2R,3R,4S,8R)-2-(1-(1-(3,5-bis(Trifluoromethyl)phenyl)ethyl)oxy)-3-(3-bromo)phenyl-4-vinyl-3,4,5,6-tetrahydropyran The title compound was prepared from the mixture of lactol isomers of trans 3-(3-bromo)phenyl-4-vinyltetrahydropyran-2-ol (from 3-bromophenylboronic acid using procedures analogous to Descriptions 18,19 and 20) and (R)-1-(3,5-bis(trifluoromethyl)phenyl)ethanol by a procedure analogous to Example 4. 2,3-trans-3,4-trans isomer 4 (2R,3R,4S,8R);

$^1$H NMR (CDCl$_3$, 400 MHz) δ 1.39 (3H, d, J 6.6), 1.60–1.80 (2H, m), 2.35–2.52 (2H, m), 3.53–3.63 (1H, m), 4.10–4.18 (1H, m), 4.20 (1H, d, J 8.0), 4.79 (1H, d, J 17), 4.82 (1H, d, J 10), 4.94 (1H, q, J 6.6), 5.45 (1H, ddd, J 17, 10, 6.8), 6.92 (1H, d, J 7.8), 7.08 (1H, t, J 7.8), 7.17 (1H, s), 7.22 (2H, s), 7.32 (1H, br. d, J 7.8), 7.68 (1H, br.s)

EXAMPLE 161

(2R,3R,4S,8R)-2-(1-(1-(3,5-bis(Trifluoromethyl)phenyl)ethyl)oxy)-3-(3-bromo)phenyl-4-(methanesulfonyloxymethyl)-3,4,5,6-tetrahydropyran The title compound was prepared from the product of Example 160 (2,3-trans-3,4-trans isomer) by procedures analogous to those described in Examples 5 and 6.

EXAMPLE 162

(2R,3R,4S,8R)-2-(1-(1-(3,5-bis(Trifluoromethyl)phenyl)ethyl)oxy)-3-(3-bromo)phenyl-4-((3R)-3-carboxy-3-methylpiperidin-1-yl)methyl-3,4,5,6-tetrahydropyran The title compound was prepared from the product of Example 161 and (3R)-ethyl 3-methylpiperidine-3-carboxylate (Description 32) by procedures analogous to those described in Example 52 and 53.

$^1$H NMR (400 MHz, CDCl$_3$) δ 1.11(3H, s), 1.37(3H, d, J 6.8 Hz), 1.43–1.78(5H, m), 1.87–1.93(2H, m), 1.99–2.25 (4H, m), 2.35(1H, dt, J 8.3 and 3 Hz), 2.76(1H, d, J 11.7 Hz), 2.85–2.96(1H, m), 3.55(1H, dt, J 12.2 and 2.2 Hz), 4.08–4.20(2H, m), 4.94(1H, q, J 6.6 Hz), 6.92(1H, d, J 7.8 Hz), 7.12(1H, t, J 7.8 Hz), 7.15–7.23(3H, m), 7.38(1H, d, J 7.9 Hz), 7.69(1H, s).

EXAMPLE 163

(2R,3R,4S,8R)-2-(1-(1-(3,5-bis(Trifluoromethyl)phenyl)ethyl)oxy)-3-(3-$^3$H)phenyl-4-((3R)-3-carboxy-3-methylpiperidin-1-yl)methyl-3,4,5,6-tetrahydropyran The product of Example 160 was treated with tritium gas in the presence of palladium and the product purified on HPLC to give the title compound MS m/z 576 (M+H).

EXAMPLE 164

(2R,3R,4S,8R)-2-(1-(1-(3,5-bis(Trifluoromethyl)phenyl)ethyl)oxy)-3-(3-bromo)phenyl-4-(4-carboxy-4-methylpiperidin-1-yl)methyl-3,4,5,6-tetrahydropyran The title compound was prepared from the product of Example 161 and ethyl 4-methylpiperidine-4-carboxylate by procedures analogous to those described in Example 52 and 53.

$^1$H NMR (360 MHz, CDCl$_3$) δ 1.15(3H, s), 1.38(3H, d, J 6.6 Hz), 1.66(v. broad s), 1.90–2.01(5H, m), 2.33(2H, dd J 11.2 Hz and 8.8 Hz), 2.50(1H, m), 3.51(1H t J 11.6 Hz), 4.12(1H, dd, J 11.8 Hz and 3.7 Hz), 4.16(1H d J 8.2 Hz), 4.91(1H, q J 6.7 Hz), 6.9(1H, d J 8.2 Hz), 7.09(1H, t J 7.7 Hz), 7.17(1H,s), 7.20(2H, s), 7.34(1H, d J 8.1 Hz), 7.65(1H, s). MS m/z 651,653(M+H Br$^{79}$ and Br$^{81}$).

EXAMPLE 165

(2R,3R,4S,8R)-2-(1-(1-(3,5-bis(Trifluoromethyl)phenyl)ethyl)oxy)-3-(3-$^3$H)phenyl-4-(4-carboxy-4-methylpiperidin-1-yl)methyl-3,4,5,6-tetrahydropyran The product of Example 164 was treated with tritium gas in the presence of palladium and the product purified on HPLC to give the title compound MS m/z 576 (M+H).

EXAMPLE 166

(2R,3R,4S,8R)-2-(1-(1-(3,5-bis(Trifluoromethyl)phenyl)ethyl)oxy)-3-(3-bromo)phenyl-4-(4-carboxypiperidin-1-yl)methyl-3,4,5,6-tetrahydropyran The title compound was prepared from the product of Example 161 and ethyl piperidine-4-carboxylate by procedures analogous to those described in Example 52 and 53.

$^1$H NMR (360 MHz, CDCl$_3$) δ1.38(3H, d J 6.6 Hz), 1.66(3H, m), 1.82(2H, m), 1.94–2.22(6H, m), 2.33(1H, dd J 10.9 Hz and 8.4 Hz), 2.71(1H, dm, J 10.2 Hz), 2.81(1H, dm), 3.50(1H, td J 10.7 Hz and 1.3 Hz), 4.10(1H, dd J 11.9 Hz and 3.9 Hz), 4.15(1H, d J 8.3 Hz), 4.91(1H, q J 6.6 Hz), 6.91(1H, d J 7.6 Hz), 7.09(1H, t J 7.8 Hz), 7.18(1H,s), 7.19(2H,s), 7.35(1H, d J 8.03 Hz), 7.68(1H, s). MS (ES$^+$) m/z 637,639 (M+H Br$^{79}$ and Br$^{81}$).

EXAMPLE 167

(2R,3R,4S,8R)-2-(1-(1-(3,5-bis(Trifluoromethyl)phenyl)ethyl)oxy)-3-(3-$^3$H)phenyl-4-(4-carboxypiperidin-1-yl)-3,4,5,6-tetrahydropyran The product of Example 166 was treated with tritium gas in the presence of palladium and the product purified on HPLC to give the title compound MS m/z 562 (M+H).

EXAMPLE 168

(2R,3R,4R,8R)-2-(1-(1-(3,5-bis(Trifluoromethyl)phenyl)ethyl)oxy)-4-(imidazol-2-yl)-3-phenyl-3,4,5,6-tetrahydropyran The aldehyde product of Example 45 (0.2 g) and glyoxal (0.104 ml of a 40% aqueous solution) were dissolved in ethanol and added to a saturated solution of ammonia in ethanol. The mixture was stirred at room temperature for 4 hours then the solvents were removed under vacuum to afford a yellow solid. This was purified on alumina, eluting with 10% ethyl acetate in hexane, increasing to 75% ethyl acetate in hexane, to afford the title compound as a white solid (70 mg).

$^1$H NMR (400 MHz, CDCl$_3$) δ 1.38 (3H, d, J 6.6 Hz), 2.09–2.17 (11H, m), 2.21–2.34 (1H, m), 2.90 (1H, dd, J 11.6, 8.2 Hz), 3.18 (1H, td, J 11.5, 4.0 Hz), 3.66 (1H, td, J 12.0, 2.0 Hz), 4.23 (1H, d, J 11.5 Hz), 4.36 (1H, d J 8.2 Hz), 5.0 (1H, q, J 6.5 Hz), 6.74 (2H, s br), 7.00–7.06 (2H, m), 7.22 (2H, s), 7.24–7.26 (3H, m), 7.68 (1H, s); MS (ES$^+$) m/z 227 (M–257).

EXAMPLE 169

(2R,3R,4R,8R)-2-(1-(1-(3,5-bis(Trifluoromethyl)phenyl)ethyl)oxy)-4-(1-methylimidazol-2-yl)-3-phenyl-3,4,5,6-tetrahydropyran The imidazole described in Example 168 (0.15 g, 0.31 mmol) was dissolved in acetone (1 ml) and powdered potassium hydroxide (0.089 g, 1.56 mmol) was added. The yellow mixture was stirred at room temperature under an atmosphere of nitrogen for 10 minutes. Methyl iodide (0.31 ml of a 1M solution in acetone) was added and the mixture was stirred at room temperature for 20 minutes. The reaction mixture was extracted with ethyl acetate and the pooled organic extracts were washed with brine, dried (magnesium sulfate), and concentrated in vacuo to afford a yellow oil.

This was purified on silica, eluting with ethyl acetate, increasing to 2% methanol in ethyl acetate. This afforded the title compound as a white solid (98 mg).

$^1$H NMR (360 MHz, CDCl$_3$) δ 1.35 (3H, d, J 6.6 Hz), 1.73 (1H, dm, J 13.5 Hz), 2.12 (1H, qd, J 25.8, 4.8 Hz), 3.04 (1H, dd, J 11.6, 8.7 Hz), 3.12 (3H, s), 3.30–3.38 (1H, m), 3.76 (1H, td, J 12.3, 2.2 Hz), 4.15 (1H, dd, J 11.9, 4.7 Hz), 4.64 (1H, d, J 8.7 Hz), 5.10 (1H, q, J 6.5 Hz), 6.60 (1H, d, J 1.3 Hz)), 6.77 (1H, d, J 1.3 Hz), 6.92–6.95 (2H, m), 7.04–7.08 (3H,m), 7.41 (2H, s), 7.75 (1H, s); MS (ES$^+$) m/z 241 (M–257), 499 (M+1).

EXAMPLE 170

(2R,3R,4R,8R)-2-(1-(1-(3,5-bis(Trifluoromethyl)phenyl)ethyl)oxy)-4-(imidazol-2-yl)methyl-3-phenyl-3,4,5,6-tetrahydropyran i) (2R,3R,4S,8R)-2-(1-(1-(3,5-bis(Trifluoromethyl)phenyl)ethyl)oxy)-4-(formylmethyl)-3-phenyltetrahydropyran The title compound was prepared from the product of Example 37 by a procedure analogous to that described in Example 43.

$^1$H NMR (360 MHz, CDCl$_3$) δ 1.37(3H, d J 6.6 Hz), 1.43–1.53(1H, m), 1.83(1H, dm J 13.4 Hz), 2.20(2H, m), 2.38(1H, m), 2.48(1H, dd J 11.6 Hz and 8.14 Hz), 3.58(1H, td J 12.1 Hz and 2.3 Hz), 4.09(1H, m), 4.26(1H, d J 8.1 Hz), 4.95(1H,q J 6.6 Hz),7.02(2H, m), 7.17(2H, s), 7.22–7.26 (3H, m), 7.66(1H, s), 9.49(1H, s).

ii) (2R,3R,4R,8R)-2-(1-(1-(3,5-bis(Trifluoromethyl)phenyl)ethyl)oxy)-4-(imidazol-2-yl)methyl-3-phenyl-3,4,5,6-tetrahydropyran The title compound was prepared from the aldehyde product of Example 170 (i) by a procedure analogous to that described in Example 168.

$^1$H NMR (360 MHz, CDCl$_3$) δ 1.35 (3H, d, J 6.6 Hz), 1–50–1.63 (1H, m), 1.72 (1H, dm, J 13.3 Hz), 2.18–2.38 (2H, m), 2.42–2.47 (1H, m), 2.57 (1H, dd, J 14.4, 3.2 Hz), 3.51 (1H, td, J 12.1, 2.3 Hz), 4.07 (1H, dm, J 11.7 Hz), 4.21 (1H, d, J 8.3 Hz), 4.92 (1H, q, J 6.6 Hz), 6.86 (2H, s), 7.06–7.08 (2H, m), 7.21 (2H, s), 7.23–7.26 (3H, m), 7.65 (1H, s); MS (ES$^+$) m/z 241 (M–257), 499 (M+1).

EXAMPLE 171

(2R,3R,4R,8R)-2-(1-(1-(3,5-bis(Trifluoromethyl)phenyl)ethyl)oxy)-4-(5-methylimidazol-2-yl)-3-phenyl-3,4,5,6-tetrahydropyran The title compound was prepared from the aldehyde product of Example 45 by a procedure analogous to that described in Example 168, using pyruvic aldehyde instead of glyoxal.

$^1$H NMR (360 MHz, CD$_3$OD) δ 1.35 (3h, d, J 6.6 Hz), 1.78 (1H, dm, J 13.3 Hz), 1.97–2.04 (4H, m), 3.02 (1H, dd, J 12.0, 8.4 Hz), 3.20 (1H, td, J 12.0, 4.1 Hz), 3.30 (1H, td, J 3.2, 1.7 Hz), 4.09–4.16 (1H, m), 4.46 (1H, d, J 8.4 Hz), 5.05 (1H, q, J 6.6 Hz), 6.36 (1H, s), 6.99–7.01 (2H, m), 7.06–7.10 (3H, m), 7.35 (2H, s), 7.73 (1H, s); MS (ES$^+$) m/z 241 (M–257), 499 (M+1).

EXAMPLE 172

(2R,3R,4R,8R)-2-(1-(1-(3,5-bis(Trifluoromethyl)phenyl)ethyl)oxy)-4-(5-methylimidazol-2-yl)methyl-3-phenyl-3,4,5,6-tetrahydropyran The title compound was prepared from the aldehyde product of Example 170 (i) by a procedure analogous to that described in Example 171.

$^1$H NMR (360 MHz, CDCl$_3$) δ 1.35 (3H, d, J 6.6 Hz), 1.56 (1H, qd, J 11.8, 4.2 Hz), 1.71–1.75 (1H, m), 2.13 (3H, s), 2.20–2.31 (2H, m), 2.40–2.54 (2H, m), 3.51 (1H, td, J 12.1, 2.2 Hz), 4.05–4.15 (1H, m), 4.20 (1H, d, J 8.3 Hz), 4.93 (1H, q, J 6.5 Hz), 6.51 (2H, s), 7.05–7.07 (2H, m), 7.16 (2H, s), 7.23–7.27 (3H, m), 7.66 (1H, s); MS (ES$^+$) m/z 255 (M−257), 513 (M+1).

EXAMPLE 173

(2R,3R,4R,8R)-2-(1-(1-(3,5-bis(Trifluoromethyl) phenyl)ethyl)oxy)-4-(1-methylimidazol-2-yl)methyl-3-phenyl-3,4,5,6-tetrahydropyran The title compound was prepared from the compound described in Example 170 (ii) by a procedure analogous to that described in Example 169.

$^1$H NMR (360 MHz, CDCl$_3$) δ 1.36 (3H, d, J 6.6 Hz), 1.48–1.72 (1H, m), 1.83 (1H, d, J 13.9 Hz), 2.25–2.34 (2H, m), 2.41–2.56 (2H, m), 3.26 (3H, s), 3.54 (1H, td, J 12.0, 1.8 Hz), 4.08 (1H, dm, J 12.0 Hz), 4.25 (1H, d, J 8.3 Hz), 4.94 (1H, q, J 6.6 Hz), 6.67 (1H, s), 6.86 (1H, s), 7.09–7.11 (2H, m), 7.18 (2H, s), 7.23–7.26 (3H, m), 7.66 (1H, s); MS (ES$^+$) m/z 255 (M−257), 513 (M+1).

EXAMPLE 174

(2R,3R,4R,8S)-2-(1-(1-(3,5-bis(Trifluoromethyl) phenyl)-2-hydroxyethyl)oxy)-3-phenyl-4-[((3'R)-3-carboxy-3-methylpiperidin-1-yl)methyl]-3,4,5,6-tetrahydropyran i) (2R,3R,4R,8S)-2-(2-Benzyloxy-1-(1-(3,5-bis (trifluoromethyl)phenyl)ethyl)oxy)-3-phenyl-4-[((3'R)-3-ethoxycarbonyl-3-methylpiperidin-1-yl)methyl]-3,4,5,6-tetrahydropyran The title compound was prepared from the product of Description 30 and the product of Description 32 using a procedure analogous to that described in Example 52.

ii) (2R,3R,4R,8S)-2-(1-(1-(3,5-bis(trifluoromethyl)phenyl)-2-hydroxyethyl)oxy)-3-phenyl-4-[((3'R)-3-ethoxycarbonyl-3-methylpiperidin-1-yl)methyl]-3,4,5,6-tetrahydropyran The title compound was prepared from the product of Example 174 (i) by catalytic hydrogenation (palladium hydroxide in methanol with addition of 1 equivalent of hydrogen chloride) at 40psi.

$^1$H NMR (CDCl$_3$, 360 MHz): δ 1.07 (3H, s), 1.26 (3H, t, J 7.1 Hz), 1.38–1.62 (4H, m), 1.70–1.80 (1H, m), 1.88–2.04 (4H, m), 2.35–2.48 (2H, m), 2.64–2.73 (1H, m), 3.21 (1H, dd, J 9.4, 2.8 Hz), 3.47–3.66 (3H, m), 4.09–4.20 (4H, m), 4.36 (1H, d, J 8.5 Hz), 4.78 (1H, dd, J 8.1, 2.9 Hz), 7.05–7.07 (2H, m), 7.14–7.26 (5H, m), 7.64 (1H, s). MS (ES$^+$) m/z 618 (M+1, 100%), 344 (M−273, 65%)

iii) (2R,3R,4R,8S)-2-(2-Hydroxy-1-(1-(3,5-bis (trifluoromethyl)phenyl)ethyl)oxy)-3-phenyl-4-[((3'R)-3-carboxy-3-methylpiperidin-1-yl)methyl]-3,4,5,6-tetrahydropyran The title compound was saponified with sodium hydroxide in an analogous manner to that described in Example 53.

$^1$H NMR (CDCl$_3$, 400 MHz): δ 1.10 (3H, s), 1.51–1.77 (5H, m), 1.88–1.97 (2H, m), 2.03 (1H, d, J 11.7 Hz), 2.14–2.27 (3H, m), 2.43–2.48 (1H, m), 2.77 (1H, d, J 11.7 Hz), 2.92 (1H, br d, J 8.0 Hz), 3.29–3.70 (3H, m), 4.25 (1H, dd, J 12.0, 3.5 Hz), 4.40 (1H, d, J 8.4 Hz), 7.06 (2H, dd, J 7.8, 2.0 Hz), 7.20–7.27 (3H, m), 7.66 (1H, s). MS (ES$^+$) m/z 590 (M+1, 100%), 316 (M−273, 45%)

EXAMPLE 175

(2R,3R,4R,8R)-2-(1-(1-(3,5-bis(Trifluoromethyl) phenyl)ethyl)oxy)-4-(5-chloromethyl-1,2,4-triazol-3-yl)-3-phenyl-3,4,5,6-tetrahydropyran The compound of Description 34 (300 mg) was dissolved in methanol and sodium acetate (230 mg) was added. Bromine (0.03 ml) in methanol was added dropwise and the reaction was monitored by tlc and mass spectroscopy. The reaction was complete after addition of the bromine; the mixture was concentrated in vacuo and the residue was dispersed between ethyl acetate and aq. sodium thiosulfate. The organic phase was washed with water, brine, dried (MgSO$_4$) and concentrated in vacuo. The residue was purified by chromatography on silica using 10–30% ethyl acetate in hexane. This afforded the title compound as a colourless solid, 100 mg.

$^1$H NMR (400 MHz, CDCl$_3$) δ 1.38 (3H, d, J 6.6 Hz), 2.09–2.20 (2H, m), 3.01 (1H, dd, J 11.4, 8.0 Hz), 3.29 (1H, dt, J 11.3, 4.7 Hz), 3.67 (1H, dt, J 11.8, 3.0 Hz), 4.19–4.24 (1H, m), 4.37 (1H, d, J 8.0 Hz), 4.53 (2H, s), 5.01 (1H, q, J 6.6 Hz), 7.04–7.07 (2H, m), 7.21 (2H, s), 7.22–7.26 (3H, m), 7.68 (1H, s). MS (ES$^+$) m/z 534 (M+H, 10%), 276 (M+H−257, 100%).

EXAMPLE 176

(2R,3R,4R,8R)-2-(1-(1-(3,5-bis(Trifluoromethyl) phenyl)ethyl)oxy)-4-(5-dimethylaminomethyl-1,2,4-triazol-3-yl)-3-phenyl-3,4,5,6-tetrahydropyran The compound of Example 175 (90 mg) was dissolved in methanol (0.5 ml) and methanolic dimethylamine (1 ml) was added; the solution was stirred for 10 hours. The solution was concentrated in vacuo. The residue was purified by chromatography on silica using 5–10% methanol in dichloromethane (containing 0.2% methanolic ammonia). This afforded the title compound as a colourless solid, 50 mg.

$^1$H NMR (400 MHz, MeOH-d$_4$) δ 1.36 (3H, d, J 6.6 Hz), 1.85–1.92 (1H, m), 2.02–2.15 (1H, m), 2.72 (6H, m), 3.06 (1H, dd, J 11.9, 8.5 Hz), 3.47 (1H, dt, J 7.72, 4.7 Hz), 3.80 (1H, dt, J 11.5, 2.3 Hz), 4.16–4.22 (1H, m), 4.24 (2H, s), 4.45 (1H, d, J 8.5 Hz), 5.08 (1H, q, J 6.6 Hz), 7.01–7.03 (2H, m), 7.09–7.12 (3H, m), 7.35 (2H, s), 7.73 (1H, s). MS (ES$^+$) m/z 543 (M+H, 80%), 285 (M+H−257, 100%)

The Examples shown below in Tables 5–8 were prepared by alkylation of the appropriate mesylate with a variety of amines. For the Examples in Tables 7 and 8, the intermediates contained a benzyloxy group which was deprotected by standard hydrogenolysis conditions, as described in Example 174.

TABLE 5

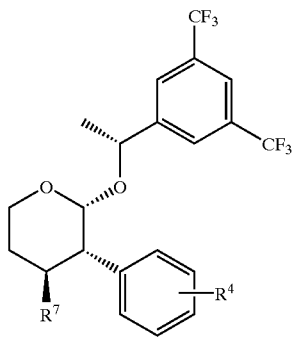

| Ex. No. | From mesylate | R⁷ | R⁴ | MS (ES⁺) (M + H) | ¹H NMR | Stereochemistry |
|---|---|---|---|---|---|---|
| 177 | Ex. 6 | (N-piperidine spiro γ-butyrolactone, CH₂) | H | 586 | (400 MHz, CDCl₃) δ 1.46 (3H, d, J 6.6 Hz), 1.48–1.78 (5H, m), 1.90 (1H, t, J 9.7 Hz), 2.05–2.21 (4H, m), 2.38 (1H, d, J 10.9 Hz), 2.48–2.55 (1H, m), 2.59–2.71 (2H, m), 2.93 (1H, d, J 11.2 Hz), 3.74 (1H, dd, J 11.1, 4.8 Hz), 4.01–4.12 (2H, m), 4.27–4.32 (2H, m), 4.41 (1H, d, J 2.9 Hz), 4.95 (1H, q, J 6.6 Hz), 7.21–7.29 (3H, m), 7.35 (2H, s), 7.67 (1H, s). | 2R, 3S, 4S, 8R, 9(3R/S) epimer 1 |
| 178 | Ex. 6 | (N-piperidine spiro γ-butyrolactone, CH₂) | H | 586 | (360 MHz, CDCl₃) δ 1.45 (3H, d, J 6.6 Hz), 1.50–1.65 (5H, m), 1.90–2.02 (3H, m), 2.10–2.17 (2H, m), 2.30–2.37 (1H, m), 2.55–2.67 (4H, m), 3.73–3.77 (1H, m), 3.99 (1H, td, J 12.1, 2.3 Hz), 4.12 (1H, q, J 5.71 Hz), 4.28 (2H, t, J 7.4 Hz), 4.41 (1H, d, J 2.3 Hz), 4.86 (1H, q, J 6.6 Hz), 7.15–7.16 (4H, m), 7.24–7.28 (3H, m), 7.60 (1H, s). | 2R, 3S, 4S, 8R, 9(3S/R) epimer 2 |

TABLE 6

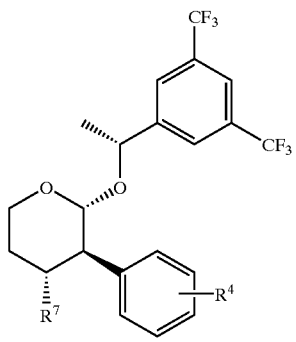

| Ex. No. | From mesylate | R⁷ | R⁴ | MS (ES⁺) (M + H) | ¹H NMR | Stereochemistry |
|---|---|---|---|---|---|---|
| 179 | Ex. 31 | (N-piperidine spiro γ-butyrolactone, CH₂) | H | 586 | (400 MHz, CDCl₃) δ 1.35 (3H, d, J 6.6 Hz), 1.40–1.68 (6H, m), 1.93–2.10 (4H, m), 2.16 (1H, d, J 11.0 Hz), 2.31–2.46 (3H, m), 2.66 (1H, d, J 10.8 Hz), 3.52 (1H, td, J 12.0, 1.8 Hz), 4.10–4.28 (5H, m), 4.94 (1H, q, J 6.6 Hz), 6.97–7.00 (2H, m), 7.17 (2H, s), 7.21–7.23 (3H, m), 7.66 (1H, s); MS (ES⁺) m/z 328 (M−257), (M + 1). | 2R, 3R, 4R, 8R, 9(3S/R) epimer 2 |

TABLE 6-continued

| Ex. No. | From mesylate | R⁷ | R⁴ | MS (ES⁺) (M + H) | ¹H NMR | Stereochemistry |
|---|---|---|---|---|---|---|
| 180 | Ex. 31 | (CH₂-piperidine spiro γ-butyrolactone, N-linked) | H | 586 | (360 MHz, CDCl₃) δ 1.35 (3H, d, J 6.5 Hz), 1.43–1.55 (3H, m), 1.85–2.10 (8H, m), 2.21–2.28 (1H, m), 2.37–2.44 (2H, m), 2.55 (1H, d, J 11.3 Hz), 3.52 (1H, t, J 12.1 Hz), 4.09–4.27 (5H, m), 4.93 (1H, q, J 6.7 Hz), 6.97–6.99 (2H, m), 7.16 (2H, s), 7.21–7.22 (3H, m), 7.66 (1H, s). | 2R, 3R, 4R, 8R, 9(3S/R) epimer 2 |
| 181 | Ex. 149 | (CH₂-piperidine spiro γ-butyrolactone, N-linked) | F | 604 | (400 MHz, CDCl₃) δ 1.36 (3H, d, J 6.6 Hz), 1.43 (3H d, J 13.4 Hz), 1.64–1.73 (1H, m), 1.81–2.08 (8H, m), 2.38 (1H, t, J 9.4 Hz), 2.51–2.59 (1H, m), 2.63–2.71 (1H, m), 3.51 (1H, td, J 11.9, 1.7 Hz), 4.10–4.15 (3H, m), 4.21 (2H, t, J 7.0 Hz), 4.95 (1H, q, J 6.6 Hz), 6.91–7.00 (4H, m), 7.17 (2H, s), 7.67 (1H, s). | 2R, 3R, 4R, 8R |
| 182 TFA salt | Ex. 31 | CH₂-piperidine-3-yl-(4-Me-1,2,4-triazol-3-yl) | H | 597 | (360 MHz, CDCl₃) δ 1.35 (3H, d, J 6.6 Hz), 1.57–1.78 (3H, m), 1.87 (1H, d, J 13.7 Hz), 2.05 (1H, d, J 14.2 Hz), 2.36–2.48 (5H, m), 2.68–2.80 (1H, m), 2.84–2.92 (1H, m), 3.40–3.47 (2H, m), 3.52–3.58 (1H, m), 3.68 (3H, s), 3.95–4.05 (1H, m), 4.14 (1H, d, br), 4.24 (1H, d, J 7.3 Hz), 4.92 (1H, q, J 6.5 Hz), 6.99–7.02 (2H, m), 7.15 (2H, s), 7.26–7.27 (3H, m), 7.85 (1H, s), 8.05 (1H, s) | 2R, 3R, 4R, 8R, 9(3R/S) epimer 1 |
| 183 TFA salt | Ex. 31 | CH₂-piperidine-3-yl-(4-Me-1,2,4-triazol-3-yl) | H | 597 | | 2R, 3R, 4R, 8R, 9(3R/S) epimer 2 |
| 184 | Ex. 31 | CH₂-piperidine-4-yl-(tetrazol-1-yl) | H | 584 | | 2R, 3R, 4R, 8R |

TABLE 7

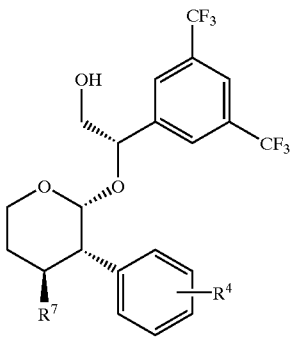

| Ex. No. | From mesylate | R⁷ | R⁴ | MS (ES⁺) (M + H) | ¹H NMR | Stereochemistry |
|---|---|---|---|---|---|---|
| 185 HCl salt | Desc. 28 | CH₂NMe₂ | H | 492 | (360 MHz, MeOH-d₄) δ 1.65 (1H, dddd, J 4.9, 12.9, 12.9, 12.9 Hz), 2.02–2.06 (1H, m), 2.71–2.78 (2H, m), 2.85 (6H, s), 2.92 (1H, br t, J 12.8 Hz), 3.13–3.25 (1H, m), 3.65–3.74 (2H, m), 3.76–3.81 (1H, m), 4.27 (1H, dt, J 2.0, 12.7 Hz), 4.50 (1H, d, J 2.8 Hz), 4.93 (1H, dd, J 4.4, 6.6 Hz), 7.29–7.38 (6H, m), 7.72 (1H, s). | 2R, 3S, 4S, 8S |
| 186 HCl salt | Desc. 28 | CH₂-azetidinyl | H | 504 | (400 MHz, MeOH-d₄) δ 1.61 (1H, dddd, J 5.0. 12.9, 12.9, 12.9 Hz), 1.90–1.94 (1H, m), 2.74 (1H, dd, J 3.2, 11.5 Hz), 2.83–2.94 (3H, m), 3.64–3.78 (3H, m), 4.01–4.12 (4H, m), 4.22 (1H, dt, J 2.4, 12.0 Hz), 4.48 (1H, d, J 4.5, 6.7 Hz), 7.30–7.38 (6H, m), 7.72 (1H, s). | 2R, 3S, 4S, 8S |
| 187 HCl salt | Desc. 28 | CH₂NHMe | H | 478 | (360 MHz, CDCl₃) δ 1.70 (1H, dddd, J 5.0, 13.1, 13.1, 13.1 Hz), 2.58–2.66 (5H, m), 2.74 (1H, dd, J 2.8, 12.1 Hz), 2.82–2.85 (1H, m), 3.57–3.79 (3H, m), 4.30 (1H, t, J 11.1 Hz), 4.55 (1H, d, J 2.8 Hz), 4.93 (1H, dd, J 2.8, 8.6 Hz), 7.19 (2H, s), 7.32–7.40 (5H, m), 7.65 (1H, s). | 2R, 3S, 4S, 8S |
| 188 | Desc. 29 | CH₂CH₂NMe₂ | H | 506 | (360 MHz, CDCl₃) δ 0.94–1.05 (1H, m), 1.41–1.58 (2H, m), 1.65–1.88 (2H, m), 1.96 (1H, d, J 13.2 Hz), 2.16 (6H, s), 2.39–2.51 (1H, m), 2.60–2.69 (2H, m), 3.65–3.74 (2H, m), 3.78 (1H, dd, J 11.3, 4.9 Hz), 4.16 (1H, t, br J 11.05 Hz), 4.55 (1H, s, br), 4.85 (1H, dd, J 6.7 Hz), 7.22–7.31 (7H, m), 7.65 (1H, s) | 2R, 3S, 4S, 8S |
| 189 | Desc. 28 | CH₂-piperazinyl | H | 533 | (400 MHz, CDCl₃) δ 1.44–1.55 (1H, m), 1.88–1.94 (1H, m), 2.11–2.18 (4H, m), 2.40–2.50 (2H, m), 2.58–2.67 (2H, m), 2.75–2.90 (4H, m), 3.70 (2H, d, J 5.4 Hz), 3.81 (1H, dd, J 3.7, 10.7 Hz), 4.07 (1H, dt, J 2.2, 13.3 Hz). 4.55 (1H, d, J 2.2 Hz), 4.82 (1H, d, J 5.4 Hz), 7.16–7.18 (2H, m), 7.21 (2H, s), 7.25–7.30 (3H, m), 7.66 (1H, s). | 2R, 3S, 4S, 8S |
| 190 | Desc. 28 | CH₂-morpholinyl | H | 534 | | 2R, 3S, 4S, 8S |
| 191 | Desc. 28 | CH₂-spirolactone | H | 603 | | 2R, 3S, 4S, 8S |

TABLE 7-continued

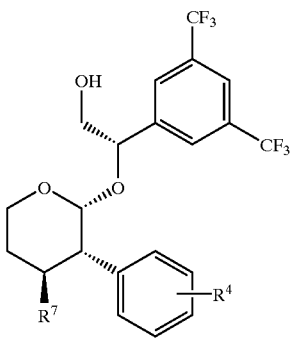

| Ex. No. | From mesylate | R⁷ | R⁴ | MS (ES⁺) (M + H) | ¹H NMR | Stereochemistry |
|---|---|---|---|---|---|---|
| 192 | Desc. 28 | ![CH2-N-piperidine-spiro-lactone] CH₂-(N-piperidine spiro γ-butyrolactone) | H | 602 | (400 MHz, CDCl₃) δ 1.47–1.62 (4H, m), 1.67–1.77 (1H, m), 1.80–1.92 (2H, m), 2.09–2.25 (5H, m), 2.46–2.53 (1H, m), 2.59–2.69 (2H, m), 2.88–2.94 (1H, m), 3.68–3.73 (2H, m), 2.78–2.84 (1H, m), 4.03–4.47 (1H, m), 4.21–4.32 (2H, m), 4.56 (1H, d, J 2.6 Hz), 4.83 (1H, t, J 5.6 Hz), 7.15.7.17 (2H, m), 7.21 (2H, s), 7.26–7.29 (3H, m), 7.67 (1H, s) | 2R, 3S, 4S, 8S, 9(R/S) epimer 1 |
| 193 | Desc. 28 | CH₂-(N-piperidine spiro γ-butyrolactone) | H | 602 | (400 MHz, CDCl₃) δ 1.45–1.68 (5H, m), 1.92–2.09 (4H, m), 2.09–2.19 (2H, m), 2.23–2.37 (1H, m), 2.53–2.68 (4H, m), 3.68–3.74 (2H, m), 3.80 (1H, dd, J 11.4, 3.8 Hz), 4.04 (1H, t, J 12.1 Hz), 4.28 (2H, t, J 7.2 Hz), 4.54 (1H, d, J 2.9 Hz), 4.83 (1H, t, J 5.4 Hz), 7.15–7.17 (2H, m), 7.20 (2H, s), 7.22–7.31 (3H, m), 7.66 (1H, s) | 2R, 3S, 4S, 8S, 9(3S/R) epimer 2 |
| 194 | Desc. 28 | CH₂-(N-piperidine-4-CO₂Et) | H | 588 | (360 MHz, CDCl₃) δ 1.19–1.30 (3H, m), 1.38–1.51 (3H, m), 1.52–2.23 (1H, m), 2.52–2.70 (3H, m), 2.89–2.96 (1H, m), 3.75 (1H, dd, J 11.2, 3.9 Hz), 4.01 (1H, dt, J 13.2, 2.2 Hz), 4.12 (2H, dq, J 7.1 Hz, 2.3 Hz), 4.42(1H, d, J 2.9 Hz), 4.87 (1H, q, J 6.6 Hz), 7.19(4H, bs), 7.23–7.30(3H, m), 7.59(1H, s). | 2R, 3S, 4S, 8S |
| 195 | — | CH₂-(N-piperidine-3-Me-3-COOH) | H | 509 | (400 MHz, CDCl₃) δ 1.20 (3H, s), 1.52–1.68 (3H, m), 1.80 (1H, d, J 11.6 Hz), 1.87–1.98 (2H, m), 2.10–2.21 (3H, m), 2.31 (1H, dd, J 13.0, 2.4 Hz), 2.70–2.80 (1H, m), 2.86 (1H, d, J 10.1 Hz), 3.13 (1H, d, J 11.5 Hz), 3.70–3.82 (3H, m), 4.13 (1H, td, J 12.2, 2.2 Hz), 4.55 (1H, d, J 3.2 Hz), 4.86 (1H, t, J 4.6 Hz), 7.19–7.20 (4H, m), 7.31–7.34 (3H, m), 7.66 (1H, s) | 2R, 3S, 4S, 8S, 9(3'R) |
| 196 | Desc. 28 | CH₂-(1,2,4-triazol-1-yl) | H | 516 | (400 MHz, CDCl₃) δ 1.62–1.69 (2H, m), 2.14 (1H, t), 2.52 (1H, dd), 3.03–3.15 (1H, m), 3.69–3.82 (4H, m), 4.03–4.16 (2H, m), 4.58 (1H, dd, J 2.4 Hz), 4.85 (1H, t), 7.20 (2H, s), 7.23–7.39 (5H, m), 7.67 (1H, s), 7.77 (1H, s), 7.94 (1H, s). | 2R, 3S, 4S, 8S |

TABLE 8

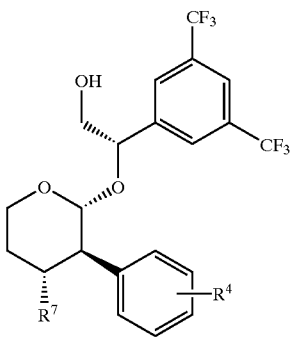

| Ex. No. | From mesylate | R⁷ | R⁴ | MS (ES⁺) (M + H) | ¹H NMR | Stereochemistry |
|---|---|---|---|---|---|---|
| 197 | Desc. 30 | N-CH₂, 3-methyl-3-(CO-OEt)-piperidine | H | 618 | (CDCl₃, 360MHz): δ1.07(3H, s), 1.26(3H, t, J 7.1Hz), 1.38–1.62(4H, m), 1.70–1.80(1H, m), 1.88–2.04(4H, m), 2.35–2.48 (2H, m), 2.64–2.73(1H, m), 3.21(1H, dd. J 9.4, 2.8Hz), 3.47–3.66(3H, m), 4.09–4.20(4H, m), 4.36(1H, d, J 8.5Hz), 4.78 (1H, dd, J 8.1, 2.9Hz), 7.05–7.07(2H, m), 7.14–7.26(5H, m), 7.64(1H, s). | 2R, 3R, 4R, 8S, 9(3'R) |
| 198 | — | N-CH₂, 3-methyl-3-(COOH)-piperidine | H | 590 | (CDCl₃, 400MHz) δ1.10(3H, s), 1.51–1.77(5H, m), 1.88–1.97 (2H, m), 2.03(1H, d, J 11.7Hz), 2.14–2.27(3H, m), 2.43–2.48 (1H, m), 2.77(1H, d, J 11.7Hz), 2.92(1H, br d, J 8.0Hz), 3.29–3.70(3H, m), 4.25(1H, dd, J 12.0, 3.5Hz), 4.40(1H, d, J 8.4Hz), 7.06(2H, dd, J 7.8, 2.0Hz), 7.20–7.27(3H, m), 7.66 (1H, s). | 2R, 3R, 4R, 8S, 9(3'R) |
| 199 | Desc. 30 | CH₂-2-oxa-8-azaspiro[4.5]decan-1-one | H | 602 | (CDCl₃, 400MHz): δ1.62–1.71(1H, m), 1.85(2H, br t, J 14.4 Hz), 2.20(2H, t, J 7.0Hz), 2.42–2.54(1H, m), 2.62–2.66(1H, m), 2.71(1H, dd, J 14.3, 4.0Hz), 2.78–2.92(5H, m), 3.12–3.36 (3H, m), 3.52(1H, td, J 8.1, 3.2Hz), 3.60(1H, td, J 8.1, 3.2 Hz), 3.72(1H, t, J 11.5Hz), 4.20–4.33(3H, m), 4.45(1H, d, J 7.5Hz), 4.82(1H, dd, J 3.0, 8.0Hz), 7.08(2H, dd, J 7.6, 2.3 Hz), 7.19((2H, s), 7.23–7.31(3H, m) 7.67(1H, s). | 2R, 3R, 4R, 8S |
| 200 | Desc. 30 | CH₂-2-oxa-7-azaspiro[4.5]decan-1-one | H | 602 | | 2R, 3R, 4R, 8S, 9(3R/S) epimer 1 |
| 201 | Desc. 30 | CH₂-2-oxa-7-azaspiro[4.5]decan-1-one | H | 602 | | 2R, 3R, 4R, 8S, 9(3S/R) epimer 2 |

TABLE 8-continued

| Ex. No. | From mesylate | R⁷ | R⁴ | MS (ES⁺) (M + H) | ¹H NMR | Stereochemistry |
|---|---|---|---|---|---|---|
| 202 | Desc. 31 | CH₂CH₂NMe₂ | H | 506 | (400MHz, CDCl₃) δ1.06–1.17(1H, m), 1.36–1.52(2H, m), 1.55–1.60(1H, s, br), 1.83(1H, dd, J 13.3, 1.7Hz), 1.90–2.00 (1H, m), 2.04–2.10(1H, m), 2.18–2.27(1H, m), 2.47(1H, dd, J 11.5, 8.6Hz), 3.47–3.52(1H, m), 3.59(1H, dd, J 11.8, 3.0Hz), 3.67(1H, td, J 12.1, 2.0Hz), 4.18(1H, dd, J 11.8, 3.3Hz), 4.40 (1H, d, J 8.5Hz), 4.78(1H, dd, J 8.3, 2.9Hz), 7.08(2H, d, J 6.7Hz), 7.16–7.22(5H, m), 7.64(1H, s). | 2R, 3R, 4R, 8S |
| 203 | Desc. 30 | CH₂-(1,2,4-triazol-1-yl) | H | 516 | (360MHz, CDCl₃) δ1.59(1H, m), 2.50(1H, m), 2.57(1H, dd, J 9.2, 3.2Hz), 3.52–3.65(3H, m), 3.84(1H, dd, J 13.9, 8.1Hz) 3.98(1H, dd, J 13.9, 3.8Hz), 4.17(1H, dm, J 11.8Hz), 4.41 (1H, d, J 18.0Hz), 4.81(1H, dd, J 8.1, 3.2Hz), 7.14–7.16(2H, m), 7.24(2H, s), 7.24–7.31(4H, m), 7.66(1H, s), 7.81(1H, s), 7.90(1H, s). | 2R, 3R, 4R, 8S |
| 204 | Desc. 30 | CH₂-pyrrolidin-1-yl | H | 518 | (360MHz, CDCl₃) δ1.45–1.61(5H, m), 1.90–2.50(9H, m), 3.14–3.22(1H, m), 3.46–3.70(3H, m), 4.21(1H, dd, J 11.7, 4.1Hz), 4.39(1H, d, J 8.5Hz), 4.79(1H, dd, J 8.2, 3.0Hz), 7.07 (2H, d, J 8.0Hz), 7.13–7.25(5H, m), 7.65(1H, s). | 2R, 3R, 4R, 8S |
| 205 | Desc. 30 | CH₂-(4-CO₂Et-piperidin-1-yl) | H | 694 | (360MHz, CDCl₃) δ1.21(3H, t J 7.1Hz), 1.43(1H, m), 1.6–1.8 (3H, m), 1.9–2.05(5H, m), 2.13(1H, m), 2.42(1H, t J 9.9Hz), 2.80(1H, d J 11.1Hz), 2.69(1H, m), 2.41(1H, dd J 10.2, 6.3Hz), 3.52(1H, td, J 11.9, 1.51Hz), 3.69(1H, dd, J 10.1, 5.4Hz), 4.07(2H, q J 7.1Hz), 4.15(1H, dd J 11.7Hz and 3.7Hz), 4.25((1H, d J 8.3Hz), 4.44(1H, d_AB J 12.1Hz), 4.48(1H, d_AB J 12.1Hz), 5.0(1H, t J 5.7Hz), 7.01(2H, m), 7.13(2, dm J 7.7Hz), 7.21–7.29(8H, m), 7.67(1H,s). | 2R, 3R, 4R, 8S |
| 206 | Desc. 31 | CH₂CH₂-(4-CO₂Et-piperidin-1-yl) | H | 618 | (360MHz, CDCl₃) δ1.22(3H, t, J 7.0Hz), 1.3–3.6(very broad signals), 3.72(3H, q, J 7.0Hz), 4.13(2H, m), 4.18(1H, m), 4.46(1H, d, J 7.7Hz), 4.82(1H, dd), 7.15(2H, d, J 4.7Hz), 7.23(5H, m), 7.65(1H, s). | 2R, 3R, 4R, 8S |

What is claimed is:
1. A compound of the formula (I):

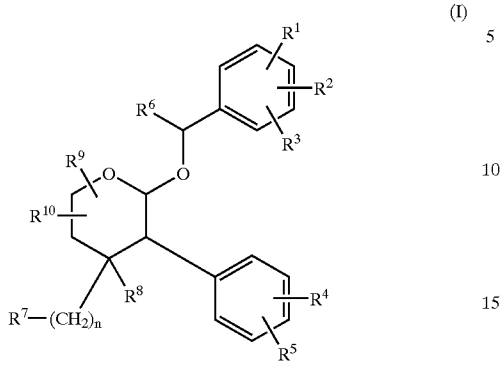

wherein
R$^1$ is hydrogen, halogen, C$_{1-6}$alkyl, C$_{1-6}$alkoxy, fluoroC$_{1-6}$ alkyl, fluoroC$_{1-6}$alkoxy, C$_{3-7}$cycloalkyl, C$_{3-7}$cycloalkylC$_{1-4}$alkyl, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, wherein R$^a$ and R$^b$ each independently represent hydrogen or C$_{1-4}$alkyl;

R$^2$ is hydrogen, halogen, C$_{1-6}$alkyl, fluoroC$_{1-6}$alkyl or C$_{1-6}$alkoxy substituted by C$_{1-4}$alkoxy;

R$^3$ is hydrogen, halogen or fluoroC$_{1-6}$alkyl;

R$^4$ is hydrogen, halogen, C$_{1-6}$alkyl, C$_{1-6}$alkoxy, fluoroC$_{1-6}$alkyl, fluoroC$_{1-6}$alkoxy, hydroxy, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, wherein R$^a$ and R$^b$ are as previously defined;

R$^5$ is hydrogen, halogen, C$_{1-6}$alkyl, fluoroC$_{1-6}$alkyl or C$_{1-6}$alkoxy substituted by C$_{1-4}$alkoxy;

R$^6$ represents hydrogen or a C$_{1-4}$alkyl group optionally substituted by a hydroxy group;

R$^7$ represents halogen, hydroxy, C$_{2-4}$alkenyl, C$_{2-4}$alkynyl, N$_3$, —NR$^{11}$R$^{12}$, —NR$^a$COR$^b$, —OSO$_2$R$^a$, —(CH$_2$)$_p$NR$^a$(CH$_2$)$_q$COOR$^b$, COR$^a$, COOR$^a$, —N=C=O, or a five membered or six membered nitrogen-containing heteroaromatic ring optionally containing 1, 2 or 3 additional heteroatoms selected from N, O and S which heteroaromatic ring is optionally substituted at any substitutable position by a substituent selected from =O, =S, halogen, hydroxy, —SH, COR$^a$, CO$_2$R$^a$, —ZNR$^{11}$R$^{12}$, C$_{1-4}$alkyl, hydroxyC$_{1-4}$alkyl, fluoroC$_{1-4}$alkyl, chloroC$_{1-4}$alkyl, C$_{1-4}$alkoxy, fluoroC$_{1-4}$alkoxy or C$_{1-4}$alkoxy substituted by a C$_{1-4}$alkoxy or hydroxyl group, and wherein said C$_{2-4}$alkenyl and C$_{2-4}$alkynyl groups are optionally substituted by a substituent selected from halogen, hydroxy, N$_3$, —NR$^{11}$R$^{12}$, —NR$^a$COR$^b$, —OSO$_2$R$^a$, —(CH$_2$)$_p$NR$^a$(CH$_2$)$_q$COOR$^b$, COR$^a$ or COOR$^a$;

R$^8$ represents hydrogen, C$_{1-6}$alkyl, fluoroC$_{1-6}$alkyl, hydroxy, C$_{1-6}$alkoxy or hydroxyC$_{1-6}$alkyl;

R$^9$ and R$^{10}$ each independently represent hydrogen, halogen, C$_{1-6}$alkyl, CH$_2$OR$^c$, oxo, CO$_2$R$^a$ or CONR$^a$R$^b$ where R$^a$ and R$^b$ are as previously defined and R$^c$ represents hydrogen, C$_{1-6}$alkyl or phenyl;

R$^{11}$ is hydrogen, C$_{1-4}$alkyl, C$_{3-7}$cycloalkyl, C$_{3-7}$cycloalkylC$_{1-4}$alkyl, C$_{2-4}$alkyl substituted by a C$_{1-4}$alkoxy or hydroxyl group, or R$^{11}$ is a five membered or six membered nitrogen-containing heteroaromatic ring as previously defined;

R$^{12}$ is hydrogen or C$_{1-4}$alkyl, C$_{3-7}$cycloalkyl, C$_{3-7}$cycloalkylC$_{1-4}$alkyl, or C$_{2-4}$alkyl substituted by a C$_{1-4}$alkoxy or hydroxyl group;

or R$^{11}$, R$^{12}$ and the nitrogen atom to which they are attached form a heteroaliphatic ring of 4 to 7 ring atoms, optionally substituted by one or two groups selected from hydroxy, COR$^e$, CO$_2$R$^e$, C$_{1-4}$alkyl optionally substituted by a C$_{1-4}$alkoxy or hydroxyl group, or C$_{1-4}$alkoxy optionally substituted by a C$_{1-4}$alkoxy or hydroxyl group, or a five membered or six membered nitrogen-containing heteroaromatic ring as previously defined, or said heteroaliphatic ring is substituted by a spiro-fused lactone ring, and said heteroaliphatic ring optionally containing a double bond, which heteroaliphatic ring may optionally contain an oxygen or sulphur ring atom, a group S(O) or S(O)$_2$ or a second nitrogen atom which will be part of a NH or NR$^d$ moiety, where R$^d$ is C$_{1-4}$alkyl optionally substituted by hydroxy or C$_{1-4}$alkoxy, and where R$^e$ is hydrogen, C$_{1-4}$alkyl or benzyl;

or R$^{11}$, R$^{12}$ and the nitrogen atom to which they are attached form a non-aromatic azabicyclic ring system of 6 to 12 ring atoms;

or R$^{11}$, R$^{12}$ and the nitrogen atom to which they are attached form a heteroaliphatic ring of 4 to 7 ring atoms to which is fused a benzene ring or a five membered or six membered nitrogen-containing heteroaromatic ring optionally containing 1, 2 or 3 additional heteroatoms selected from N, O and S;

Z represents a bond, C$_{1-6}$alkylene or C$_{3-6}$cycloalkylene;

n is zero, 1 or 2;

p is 1 or 2; and q is 1 or 2;

or a pharmaceutically acceptable salt thereof.

2. A compound of the formula (I) wherein R$^1$, R$^2$, R$^3$, R$^4$, R$^5$, R$^6$, R$^8$, R$^9$, R$^{10}$, R$^{11}$, R$^{12}$, R$^a$, R$^b$, Z, n and q are as defined in claim 1; and R$^7$ represents halogen, hydroxy, C$_{2-4}$alkenyl, N$_3$, —NR$^{11}$R$^{12}$, —NR$^a$COR$^b$, —OSO$_2$R$^a$, —(CH$_2$)$_p$NR$^a$(CH$_2$)$_q$COOR$^b$, COR$^a$, COOR$^a$, or a five membered or six membered nitrogen-containing heteroaromatic ring optionally containing 1, 2 or 3 additional heteroatoms selected from N, O and S which heteroaromatic ring is optionally substituted at any substitutable position by a substituent selected from =O, =S, halogen, hydroxy, —SH, COR$^a$, CO$_2$R$^a$, —ZNR$^{11}$R$^{12}$, C$_{1-4}$alkyl, hydroxyC$_{1-4}$alkyl, fluoroC$_{1-4}$alkyl, C$_{1-4}$alkoxy, fluoroC$_{1-4}$alkoxy or C$_{1-4}$alkoxy substituted by a C$_{1-4}$alkoxy or hydroxyl group; or a pharmaceutically acceptable salt thereof.

3. A compound of the formula (I) wherein R$^1$, R$^2$, R$^3$, R$^4$, R$^5$, R$^6$, R$^8$, R$^9$, R$^{10}$, R$^a$, R$^b$, Z and n are as defined in claim 1; and R$^7$ represents halogen, hydroxy, C$_{2-4}$alkenyl, N$_3$, —NR$^{11}$R$^{12}$, —NR$^a$COR$^b$, —OSO$_2$R$^a$, —(CH$_2$)$_p$NR$^a$(CH$_2$)$_q$COOR$^b$ or a five membered or six membered nitrogen-containing heteroaromatic ring optionally containing 1, 2 or 3 additional heteroatoms selected from N, O and S which heteroaromatic ring is optionally substituted at any substitutable position by a substituent selected from =O, =S, halogen, hydroxy, —SH, COR$^a$, CO$_2$R$^a$, —ZNR$^{11}$R$^{12}$, C$_{1-4}$alkyl, hydroxyC$_{1-4}$alkyl, fluoroC$_{1-4}$alkyl, C$_{1-4}$alkoxy, fluoroC$_{1-4}$alkoxy or C$_{1-4}$alkoxy substituted by a C$_{1-4}$alkoxy or hydroxyl group;

$R^{11}$ is hydrogen or $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;

$R^{12}$ is hydrogen or $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;

or $R^{11}$, $R^{12}$ and the nitrogen atom to which they are attached form a heteroaliphatic ring of 4 to 7 ring atoms, optionally substituted by one or two groups selected from hydroxy, $COR^a$, $CO_2R^a$ or $C_{1-4}$alkoxy optionally substituted by a $C_{1-4}$alkoxy or hydroxyl group, and said ring optionally containing a double bond, which ring may optionally contain an oxygen or sulphur ring atom, a group $S(O)$ or $S(O)_2$ or a second nitrogen atom which will be part of a NH or $NR^d$ moiety where $R^d$ is $C_{1-4}$alkyl optionally substituted by hydroxy or $C_{1-4}$alkoxy;

or $R^{11}$, $R^{12}$ and the nitrogen atom to which they are attached form a non-aromatic azabicyclic ring system of 6 to 12 ring atoms;

or a pharmaceutically acceptable salt thereof.

4. A compound as claimed in claim 1 wherein $R^1$ is hydrogen, $C_{1-4}$alkyl, $C_{1-4}$alkoxy, halogen or $CF_3$.

5. A compound as claimed in claim 1 wherein $R^2$ is hydrogen, $C_{1-4}$alkyl, $C_{1-4}$alkoxy, halogen or $CF_3$.

6. A compound as claimed in claim 1 wherein $R^3$ is hydrogen, fluorine, chlorine or $CF_3$.

7. A compound as claimed in claim 1 wherein $R^4$ is hydrogen.

8. A compound as claimed in claim 1 wherein $R^5$ is hydrogen, fluorine, chlorine or $CF_3$.

9. A compound as claimed in claim 1 wherein $R^6$ is $C_{1-4}$alkyl optionally substituted by hydroxy.

10. A compound as claimed in claim 1 wherein $R^7$ represents —$NR^{11}R^{12}$ wherein $R^{11}$ is a $C_{1-4}$alkyl group or a $C_{2-4}$alkyl group substituted by a hydroxyl or $C_{1-2}$alkoxy group, $R^{12}$ is a $C_{1-4}$alkyl group or a $C_{2-4}$alkyl group substituted by a hydroxyl or $C_{1-2}$alkoxy group, or $R^{11}$ and $R^{12}$ are linked so that, together with the nitrogen atom to which they are attached, they form a heteroaliphatic ring of 4 to 7 ring atoms optionally substituted by one or two groups, wherein the first substituent, where present, is selected from hydroxy, $CO_2R^e$ (where $R^e$ is hydrogen, methyl, ethyl or benzyl), or $C_{1-2}$alkyl substituted by hydroxy, and the second substituent, where present, is a methyl group.

11. A compound as claimed in claim 1 wherein $R^8$ is hydrogen or methyl.

12. A compound as claimed in claim 1 wherein n is 1 or 2.

13. A compound as claimed in claim 1 wherein $R^9$ and $R^{10}$ are both hydrogen atoms.

14. A compound of the formula (Ia):

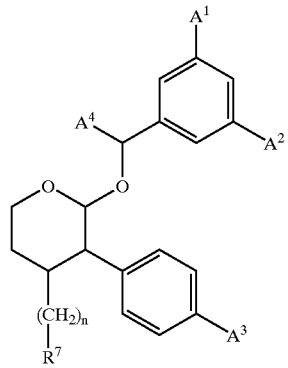

(Ia)

wherein
$A^1$ is fluorine or $CF_3$;
$A^2$ is fluorine or $CF_3$;
$A^3$ is fluorine or hydrogen;
$A^4$ is methyl or hydroxymethyl; and
$R^7$ and n are as defined in claim 1;
or a pharmaceutically acceptable salt thereof.

15. A compound as claimed in claim 1 selected from:

(2R,3S,4R,8R)-2-(1-(1-(3,5-bis(trifluoromethyl)phenyl)ethyl)oxy)-3-phenyl-4-vinyltetrahydropyran;

(2R,3R,4S,8R)-2-(1-(1-(3,5-bis(trifluoromethyl)phenyl)ethyl)oxy)-3-phenyl-4-vinyltetrahydropyran;

(2R,3S,4S,8R)-2-(1-(1-(3,5-bis(trifluoromethyl)phenyl)ethyl)oxy)-4-hydroxymethyl-3-phenyltetrahydropyran;

(2R,3S,4S,8R)-2-(1-(1-(3,5-bis(trifluoromethyl)phenyl)ethyl)oxy)-4-(methanesulfonyloxy)methyl-3-phenyltetrahydropyran;

(2RS,3SR,4SR,8RS)-4-azidomethyl-2-(1-(1-(3,5-bis(trifluoromethyl)phenyl)ethyl)-oxy)-3-phenyltetrahydropyran;

(2RS,3SR,4SR,8RS)-4-aminomethyl-2-(1-(1-(3,5-bis(trifluoromethyl)phenyl)-ethyl)oxy)-3-phenyltetrahydropyran;

(2RS,3SR,4SR,5RS)-2-(1-(1-(3,5-bis(trifluoromethyl)phenyl)ethyl)oxy)-4-(dimethylamino)methyl-3-phenyltetrahydropyran;

(2RS,3SR,4SR,8RS)-2-(1-(1-(3,5-bis(trifluoromethyl)phenyl)ethyl)oxy)-4-(pyrrolidin-1-yl)methyl-3-phenyltetrahydropyran;

(2RS,3SR,4SR,8RS)-2-(1-(1-(3,5-bis(trifluoromethyl)phenyl)ethyl)oxy)-4-(1,2,4-triazol-1-yl)methyl-3-phenyltetrahydropyran;

(2R,3S,4S,8R)-2-(1-(1-(3,5-bis(trifluoromethyl)phenyl)ethyl)oxy)-4-(2-hydroxyethyl)-3-phenyltetrahydropyran;

(2R,3S,4R,8R)-2-(1-(1-(3,5-bis(trifluoromethyl)phenyl)ethyl)oxy)-4-(2-methanesulfonyloxy)ethyl-3-phenyltetrahydropyran;

(2R,3R,4R,8R)-2-(1-(1-(3,5-bis(trifluoromethyl)phenyl)ethyl)oxy)-4-hydroxymethyl-3-phenyltetrahydropyran;

(2R,3R,4R,8R)-2-(1-(1-(3,5-bis(trifluoromethyl)phenyl)ethyl)oxy)-4-(methanesulfonyloxy)methyl-3-phenyltetrahydropyran;

(2R,3R,4R,8R)-2-(1-(1-(3,5-bis(trifluoromethyl)phenyl)ethyl)oxy)-4-(2-hydroxyethyl)-3-phenyltetrahydropyran;

(2R,3R,4S,8R)-2-(1-(1-(3,5-bis(trifluoromethyl)phenyl)ethyl)oxy)-4-(2-methanesulfonyloxy)ethyl-3-phenyltetrahydropyran;

(2R,3S,4R,8R)-2-(1-(1-(3,5-bis(trifluoromethyl)phenyl)ethyl)oxy)-4-(2-iodoethyl)-phenyltetrahydropyran;

(2R,3R,4R,8R)-2-(1-(1-(3,5-bis(trifluoromethyl)phenyl)ethyl)oxy)-4-(iodomethyl)-3-phenyltetrahydropyran;

(2R,3R,4S,8R)-2-(1-(1-(3,5-bis(trifluoromethyl)phenyl)ethyl)oxy)-4-(2-iodoethyl)-3-phenyltetrahydropyran;

(2R,3S,4S,8R)-2-(1-(1-(3,5-bis(trifluoromethyl)phenyl)ethyl)oxy)-4-formyl-3-phenyltetrahydropyran;

(2R,3S,4R,8R)-2-(1-(1-(3,5-bis(trifluoromethyl)phenyl)ethyl)oxy)-4-(2-formylmethyl)-3-phenyltetrahydropyran;

(2R,3R,4R,8R)-2-(1-(1-(3,5-bis(trifluoromethyl)phenyl)ethyl)oxy)-4-formyl-3-phenyltetrahydropyran;

(2R,3S,4R,8R)-2-(1-(1-(3,5-bis(trifluoromethyl)phenyl)ethyl)oxy)-4-carboxymethyl-3-phenyltetrahydropyran;

(2R,3R,4R,8R)-2-(1-(1-(3,5-bis(trifluoromethyl)phenyl)ethyl)oxy)-4-carboxy-3-phenyltetrahydropyran;

(2R,3R,4R,8R)-2-(1-(1-(3,5-bis(trifluoromethyl)phenyl)ethyl)oxy)-3-phenyl-4-(1,2,4-triazol-3-yl)methyltetrahydropyran;

(2R,3S,4S,8R)-2-(1-(1-(3,5-bis(trifluoromethyl)phenyl)ethyl)oxy)-3-phenyl-4-(1,2,4-triazol-3-yl)methyltetrahydropyran;

(2R,3R,4R,8R)-2-(1-(1-(3,5-bis(trifluoromethyl)phenyl)ethyl)oxy)-3-phenyl-4-(5-methoxycarbonyl-1,2,3-trazol-1-yl)ethyltetrahydropyran; and (2R,3R,4R,8R)-2-(1-(1-(3,5-bis(trifluoromethyl)phenyl)ethyl)oxy)-4-(4-methoxycarbonyl-1,2,3-triazol-1-yl)ethyl-3-phenyltetrahydropyran;

or a pharmaceutically acceptable salt thereof.

16. A compound as claimed in claim 1 selected from:

(2R,3R,4R,8R)-2-(1-(1-(3,5-bis(trifluoromethyl)phenyl)ethyl)oxy)-4-(4-methyl-4-carboxypiperidin-1-yl)methyl-3-phenyltetrahydropyran;

(2R,3R,4R,8R)-2-(1-(1-(3,5-bis(trifluoromethyl)phenyl)ethyl)oxy)-4-(4-ethoxycarbonylpiperidin-1-yl)methyl-3-phenyltetrahydropyran;

(2R,3R,4R,8R)-2-(1-(1-(3,5-bis(trifluoromethyl)phenyl)ethyl)oxy)-4-(4-carboxypiperidin-1-yl)methyl-3-phenyltetrahydropyran;

(2R,3R,4R,8R,9(3'R))-2-(1-(1-(3,5-bis(trifluoromethyl)phenyl)ethyl)oxy)-4-(3-ethoxycarbonyl-3-methylpiperidin-1-yl)methyl-3-phenyltetrahydropyran;

(2R,3R,4R,8R,9(3'S))-2-(1-(1-(3,5-bis(trifluoromethyl)phenyl)ethyl)oxy)-4-(3-ethoxycarbonyl-3-methylpiperidin-1-yl)methyl-3-phenyltetrahydropyran;

(2R,3R,4R,8R,9(3'R))-2-(1-(1-(3,5-bis(trifluoromethyl)phenyl)ethyl)oxy)-4-(3-carboxy-3-methylpiperidin-1-yl)methyl-3-phenyltetrahydropyran;

(2R,3R,4R,8R,9(3'S))-2-(1-(1-(3,5-bis(trifluoromethyl)phenyl)ethyl)oxy)-4-(3-carboxy-3-methylpiperidin-1-yl)methyl-3-phenyltetrahydropyran; and (2R,3R,4R,8R,9(3'R))-2-(1-(1-(3,5-bis(trifluoromethyl)phenyl)ethyl)oxy)-4-(3-carboxy-3-methylpiperidin-1-yl)methyl-3-(4-fluorophenyl)tetrahydropyran;

or a pharmaceutically acceptable salt thereof.

17. A compound as claimed in claim 1 selected from:

(2R,3R,4R,8R,9(3'S))-2-(1-(1-(3,5-bis(trifluoromethyl)phenyl)ethyl)oxy)-4-(3carboxy-3-methylpiperidin-1-yl)methyl-3-(4-fluorophenyl)tetrahydropyran;

(2R,3S,4R,8R)-2-(1-(1-(3,5-bis(trifluoromethyl)phenyl)ethyl)oxy)-3-(4-fluoro)phenyl-4-vinyl-3,4,5,6-tetrahydropyran;

(2R,3R,4S,8R)-2-(1-(1-(3,5-bis(trifluoromethyl)phenyl)ethyl)oxy)-3-(4-fluoro)phenyl-4-vinyl-3,4,5,6-tetrahydropyran;

(2R,3R,4R,8R)-2-(1-(1-(3,5-bis(trifluoromethyl)phenyl)ethyl)oxy)-4-hydroxymethyl-3-(4-fluoro)phenyl-3,4,5,6-tetrahydropyran;

(2R,3R,4R,8R)-2-(1-(1-(3,5-bis(trifluoromethyl)phenyl)ethyl)oxy)-4-(methanesulfonyloxy)methyl-3-(4-fluoro)phenyl-3,4,5,6-tetrahydropyran;

(2R,3R,4R,8R)-(3-{2-[1-(3,5-bis(trifluoromethyl)phenyl)ethoxy]-4-(3-dimethylaminoprop-1-ynyl)-3-phenyl-3,4,5,6-tetrahydropyran;

(2R,3R,4R,8R)-(5-{2-[1-(3,5-bis(trifluoromethyl)phenyl)ethoxy]-3-phenyl-3,4,5,6-tetrahydropyran-4-yl}-4-dimethylamino-2H-[1,2,3]triazole;

(2R,3R,4R,8R)-5-{2-[1-(3,5-bis(trifluoromethyl)phenyl)ethoxy]-3-phenyl-3,4,5,6-tetrahydropyran-4-yl}-1H-imidazole;

(2R,3S,4S,8R)-(3-{2-[1-(3,5-bis(trifluoromethyl)phenyl)ethoxy]-4-(3-dimethylaminoprop-1-ynyl)-3-phenyl-3,4,5,6-tetrahydropyran;

(2R,3S,4S,8R)-(3-{2-[1-(3,5-bis(trifluoromethyl)phenyl)ethoxy]-4-(4-dimethylaminobut-2-ynyl)-3-phenyl-3,4,5,6-tetrahydropyran;

(2R,3R,4R,8R)-2-[1-(3,5-bis(trifluoromethyl)phenyl)ethoxy]-3-phenyl-3,4,5,6-tetrahydropyran-4-carboxylic acid;

(2R,3R,4R,8R)-2-[1-(3,5-bis(trifluoromethyl)phenyl)ethoxy]-3-phenyl-3,4,5,6-tetrahydropyran-4-isocyanate;

(2R,3R,4R,8R)-4-amino-2-[1-(3,5-bis(trifluoromethyl)phenyl)ethoxy]-3-phenyl-3,4,5,6-tetrahydropyran;

(2R,3R,4R,8R)-2-[1-(3,5-bis(trifluoromethyl)phenyl)ethoxy]-4-(morpholin-4-yl)-3-phenyl-3,4,5,6-tetrahydropyran;

(2R,3R,4R,8R)-2-[1-(3,5-bis(trifluoromethyl)phenyl)ethoxy]-4-(piperidin-1-yl)-3-phenyl-3,4,5,6-tetrahydropyran;

(2R,3R,4S,8R)-2-(1-(1-(3,5-bis(trifluoromethyl)phenyl)ethyl)oxy)-3-(3-bromo)phenyl-4-vinyl-3,4,5,6-tetrahydropyran;

(2R,3R,4S,8R)-2-(1-(1-(3,5-bis(trifluoromethyl)phenyl)ethyl)oxy)-3-(3-bromo)phenyl-4-(methanesulfonyloxymethyl)-3,4,5,6-tetrahydropyran;

(2R,3R,4S,8R)-2-(1-(1-(3,5-bis(trifluoromethyl)phenyl)ethyl)oxy)-3-(3-bromo)phenyl-4-((3R)-3-carboxy-3-methylpiperidin-1-yl)methyl-3,4,5,6-tetrahydropyran;

(2R,3R,4S,8R)-2-(1-(1-(3,5-bis(trifluoromethyl)phenyl)ethyl)oxy)-3-(3-bromo)phenyl-4-(4-carboxy-4-methylpiperidin-1-yl)methyl-3,4,5,6-tetrahydropyran;

(2R,3R,4S,8R)-2-(1-(1-(3,5-bis(trifluoromethyl)phenyl)ethyl)oxy)-3-(3-bromo)phenyl-4-(4-carboxypiperidin-1-yl)methyl-3,4,5,6-tetrahydropyran;

(2R,3R,4R,8R)-2-(1-(1-(3,5-bis(trifluoromethyl)phenyl)ethyl)oxy)-4-(imidazol-2-yl)-3-phenyl-3,4,5,6-tetrahydropyran;

(2R,3R,4R,8R)-2-(1-(1-(3,5-bis(trifluoromethyl)phenyl)ethyl)oxy)-4-(1-methylimidazol-2-yl)-3-phenyl-3,4,5,6-tetrahydropyran;

(2R,3R,4R,8R)-2-(1-(1-(3,5-bis(trifluoromethyl)phenyl)ethyl)oxy)-4-(imidazol-2-yl)methyl-3-phenyl-3,4,5,6-tetrahydropyran;

(2R,3R,4R,8R)-2-(1-(1-(3,5-bis(trifluoromethyl)phenyl)ethyl)oxy)-4-(5-methylimidazol-2-yl)-3-phenyl-3,4,5,6-tetrahydropyran;

(2R,3R,4R,8R)-2-(1-(1-(3,5-bis(trifluoromethyl)phenyl)ethyl)oxy)-4-(5-methylimidazol-2-yl)methyl-3-phenyl-3,4,5,6-tetrahydropyran;

(2R,3R,4R,8R)-2-(1-(1-(3,5-bis(trifluoromethyl)phenyl)ethyl)oxy)-4-(1-methylimidazol-2-yl)methyl-3-phenyl-3,4,5,6-tetrahydropyran;

(2R,3R,4R,8S)-2-(1-(1-(3,5-bis(trifluoromethyl)phenyl)-2-hydroxyethyl)oxy)-3-phenyl-4-[((3'R)-3-carboxy-3-methylpiperidin-1-yl)methyl]-3,4,5,6-tetrahydropyran;

(2R,3R,4R,8R)-2-(1-(1-(3,5-bis(trifluoromethyl)phenyl)ethyl)oxy)-4-(5-chloromethyl-1,2,4-triazol-3-yl)-3-phenyl-3,4,5,6-tetrahydropyran;

(2R,3R,4R,8R)-2-(1-(1-(3,5-bis(trifluoromethyl)phenyl)ethyl)oxy)-4-(5-dimethylaminomethyl-1,2,4-triazol-3-yl)-3-phenyl-3,4,5,6-tetrahydropyran;

or a pharmaceutically acceptable salt thereof.

18. A compound as claimed in claim 1 wherein the stereochemistry of the 2-, 3-, 4-and 8-positions is as shown in formulae (Ib) and (Ic):

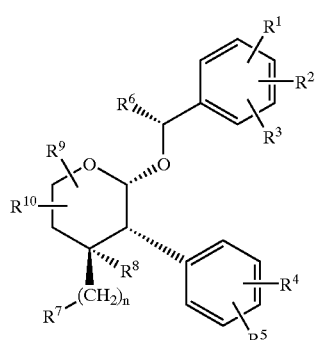

(Ib)

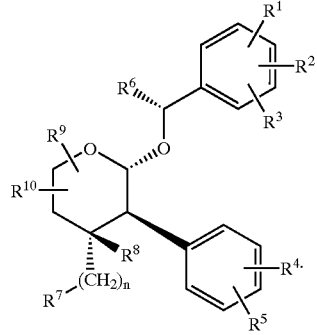

(Ic)

19. A pharmaceutical composition comprising a compound as claimed in claim 1, together with at least one pharmaceutically acceptable carrier or excipient.

20. A method for the treatment or prevention of physiological disorders associated with an excess of tachykinins, which method comprises administration to a patient in need thereof of a tachykinin reducing amount of a compound according to claim 1.

21. A method according to claim 20 for the treatment or prevention of pain or inflammation, migraine, emesis, postherpetic neuralgia, depression or anxiety.

22. A process for the preparation of a compound as claimed in claim 1 which comprises:

(A), where n is 1, reaction of a compound of formula (II)

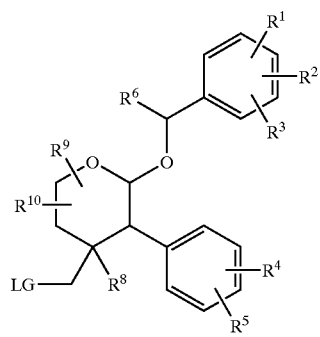

(II)

wherein LG is a suitable leaving group; with an appropriate amine of the formula $HNR^{11}R^{12}$, or a heteroaromatic compound suitable for the addition of a five or six-membered nitrogen containing heteroaromatic ring as defined in relation to claim 1, or an azide; or (B), where $R^7$ is hydroxy and n is 1 or 2, interconversion of a corresponding compound of formula (I) in which n is zero and $R^7$ is vinyl, hereinafter referred to as formula (III)

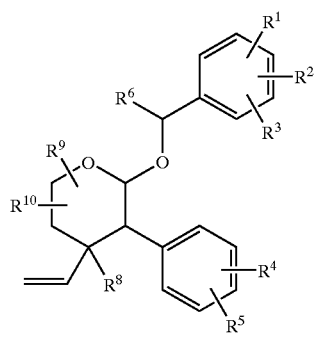

(III)

by reaction with ozone, followed by a reaction with a reducing agent, or by reaction with a reducing agent followed by hydrogen peroxide in the presence of a base; or (C) reaction of a compound of formula (IV) with a compound of formula (V)

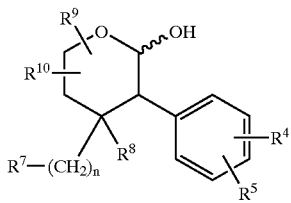

(IV)

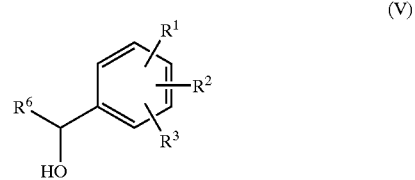

(V)

in the presence of a resin catalyst; or (D), where $R^6$ is either methyl or hydroxymethyl, reaction of a compound of formula (VI)

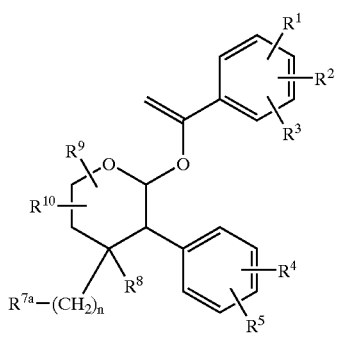

(VI)

wherein $R^{7a}$ is as defined for $R^7$ in relation to claim 1 or a precursor therefor; under either:

(a) (where $R^6$ is methyl) catalytic hydrogenation conditions; or (b) (where $R^6$ is hydroxymethyl) reducing conditions followed by treatment with hydrogen peroxide and a base;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

\* \* \* \* \*